(12) United States Patent
Wada

(10) Patent No.: US 10,139,741 B2
(45) Date of Patent: Nov. 27, 2018

(54) CHARGE TRANSPORT SUBSTANCE, ELECTROPHOTOGRAPHIC PHOTORECEPTOR, ELECTROPHOTOGRAPHIC PHOTORECEPTOR CARTRIDGE, AND IMAGE-FORMING APPARATUS

(71) Applicant: MITSUBISHI CHEMICAL CORPORATION, Chiyoda-ku (JP)

(72) Inventor: Mitsuo Wada, Kanagawa (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 73 days.

(21) Appl. No.: 14/017,796

(22) Filed: Sep. 4, 2013

(65) Prior Publication Data

US 2014/0065532 A1 Mar. 6, 2014

Related U.S. Application Data

(63) Continuation of application No. PCT/JP2012/055472, filed on Mar. 2, 2012.

(30) Foreign Application Priority Data

Mar. 4, 2011 (JP) ................................ 2011-047684
Mar. 4, 2011 (JP) ................................ 2011-047685

(51) Int. Cl.
*G03G 5/047* (2006.01)
*C07C 211/54* (2006.01)
*G03G 5/06* (2006.01)

(52) U.S. Cl.
CPC ............ *G03G 5/047* (2013.01); *C07C 211/54* (2013.01); *G03G 5/0614* (2013.01); *G03G 5/0672* (2013.01); *G03G 5/0696* (2013.01)

(58) Field of Classification Search
CPC .... G03G 5/0614; G03G 5/047; G03G 5/0564; G03G 5/0672; G03G 5/0668
(Continued)

(56) References Cited

U.S. PATENT DOCUMENTS 5,272,031 A   12/1993  Hanatani et al.
5,804,344 A   9/1998   Mitsumori
(Continued)

FOREIGN PATENT DOCUMENTS

CN   1748182 A   3/2006
CN   1846175 A   10/2006
(Continued)

OTHER PUBLICATIONS

Machine English language translation of JP 2010139645, Jun. 24, 2010.*

(Continued)

*Primary Examiner* — Hoa V Le
(74) *Attorney, Agent, or Firm* — Oblon, McClelland, Maier & Neustadt, L.L.P.

(57) ABSTRACT

The present invention is to provide a charge transport substance having high resistance to stress within electrophotographic processes, an electrophotographic photoreceptor which has excellent high-speed responsiveness, shows a sufficient residual potential, and has high resistance to stress within electrophotographic processes, an electrophotographic cartridge, and an image-forming apparatus. The invention provides a charge transport substance having a specific structure. The invention further provides an electrophotographic photoreceptor including a photosensitive layer which contains the charge transport substance having a specific structure, an electrophotographic cartridge, and an image-forming apparatus, equipped with this electrophotographic photoreceptor.

11 Claims, 8 Drawing Sheets

(58) Field of Classification Search
USPC .................. 430/58.75, 58.85; 564/434
See application file for complete search history.

(56) References Cited

U.S. PATENT DOCUMENTS

| | | | |
|---|---|---|---|
| 6,030,734 | A | 2/2000 | Mitsumori |
| 6,514,651 | B1 * | 2/2003 | Hayata .............. 430/56 |
| 7,217,483 | B2 | 5/2007 | Nozomi et al. |
| 2005/0069796 | A1 | 3/2005 | Iwasaki et al. |
| 2006/0073400 | A1 | 4/2006 | Kumano |
| 2007/0054209 | A1 | 3/2007 | Azuma et al. |
| 2007/0148571 | A1 * | 6/2007 | Iwasaki et al. ........... 430/58.75 |
| 2009/0081570 | A1 | 3/2009 | Kumano |
| 2010/0221040 | A1 | 9/2010 | Mitsumori |

FOREIGN PATENT DOCUMENTS

| | | |
|---|---|---|
| CN | 1985218 A | 6/2007 |
| CN | 101273305 A | 9/2008 |
| CN | 101317134 A | 12/2008 |
| EP | 0 506 492 A2 | 9/1992 |
| EP | 0 506 492 A3 | 9/1992 |
| JP | 02-154269 | 6/1990 |
| JP | 07-036203 | 2/1995 |
| JP | 9-244278 | 9/1997 |
| JP | 2002-080432 | 3/2002 |
| JP | 2004-101882 | 4/2004 |
| JP | 2006-008670 | 1/2006 |
| JP | 2008-083105 | 4/2008 |
| JP | 2010139645 | * 6/2010 .............. G03G 5/06 |
| WO | 2007/063989 | 6/2007 |

OTHER PUBLICATIONS

International Search Report dated May 22, 2012 in PCT/JP2012/055472 filed Mar. 2, 2012.
Lu, Jianping et al., Synthesis and Characterization of a Blue Light Emitting Polymer Containing Both Hole and Electron Transporting Units, Chemistry of Materials, 1999, 11(9), 2501-2507.
Extended European Search Report dated Jul. 25, 2014 in the corresponding European Application No. 12755397.2.
European Search Report dated May 8, 2015, in European Patent Application No. 15152831.2.
Office Action dated May 26, 2015, in Japanese Patent Application No. 2012-044497 (w/ English translation).
Office Action dated May 26, 2015, in Japanese Patent Application No. 2012-044498 (w/ English translation).
Office Action dated Jul. 15, 2015, in Chinese Patent Application No. 201280011451.4 filed Mar. 2, 2012 (with English Translation).
Office Action dated May 16, 2017, in Korean Patent Application No. 10-2013-7022937 (w/ English translation).
Office Action dated Jan. 6, 2016, in Chinese Patent Application No. 201280011451.4 filed Mar. 2, 2012 (w/ English translation).
Office Action dated Oct. 18, 2017 in Korean Patent Application No. 10-2013-7022937 (w/ English translation).
Office Action dated Dec. 4, 2017 in Korean Patent Application No. 10-2017-7033446 (w/ computer-generated English translation).

* cited by examiner

CHARGE TRANSPORT SUBSTANCE, ELECTROPHOTOGRAPHIC PHOTORECEPTOR, ELECTROPHOTOGRAPHIC PHOTORECEPTOR CARTRIDGE, AND IMAGE-FORMING APPARATUS

CROSS-REFERENCE TO RELATED APPLICATIONS

The present application is a continuation application of International Application No. PCT/JP2012/055472, filed Mar. 2, 2012, which claims priority to Japanese Patent Application No. 2011-047684, which was filed on Mar. 4, 2011, and to Japanese Patent Application No. 2011-047685, which was filed on Mar. 4, 2011. The contents of these applications are incorporated herein by reference in their entirety.

TECHNICAL FIELD

The present invention relates to an electrophotographic photoreceptor having excellent electrical properties, an electrophotographic photoreceptor cartridge produced using the electrophotographic photoreceptor, and an image-forming apparatus.

BACKGROUND ART

Electrophotography has come to be extensively applied in recent years not only in the field of copiers but also in the field of various printers and printing machines because of the excellent instantaneousness thereof, the ability thereof to give high-quality images, etc. As the photoreceptors, which are the nucleus of electrophotography, photoreceptors employing inorganic photoconductive materials such as selenium, arsenic-selenium alloys, and zinc oxide have been used hitherto. Recently, however, photoreceptors (organic photoreceptors) employing organic photoconductive materials which have advantages including causing no pollution, ease of film formation and production, and a high degree of freedom of material selection and combination are being mainly used.

Known as the layer configurations of organic photoreceptors are a so-called single-layer type photoreceptor in which a charge generation substance has been dispersed in a binder resin and a multilayer type photoreceptor in which a charge generation layer and a charge transport layer have been superposed. Photoreceptors of the multilayer type are frequently used because stable photoreceptors having high sensitivity are obtained by employing an optimal combination of a highly efficient charge generation substance and a charge transport substance and separately incorporating these substances into respective layers, and because there is a wide choice of materials to facilitate the regulation of properties.

In recent years, both copiers and printers are shifting from monochrome to full-color images. Methods for forming such a full-color image mainly include the tandem process and the four-cycle process, and methods of transfer to printing media include a direct transfer process, transfer drum process, intermediate-transfer process, multiple-development en bloc transfer process, and the like. Of these processes, the technique of color image formation by the tandem process, i.e., the process in which images of respective colors are formed in respective image-forming units and transferred successively, is an excellent process for image formation because there are a variety of recording materials usable therein, high full-color quality is attained, and full-color images can be obtained at high speed. Of these, the ability to give full-color images at high speed is an advantage not seen in the other processes.

As a result of the trends toward speed increase and full-color image formation in electrophotographic processes described above, durability in terms of repeated use has become essential to the properties required of the electrophotographic photoreceptor besides higher sensitivity and higher response speed. For providing an electrophotographic photoreceptor which satisfy these properties, it has become necessary to develop a high-performance charge transport substance which has a high mobility and shows a sufficient residual potential after exposure. Investigations on charge transport substances which have a tetraphenylbenzidine framework substituted with a styryl group or the like and in which the π-electron system has been thereby expanded are being made enthusiastically in order to overcome those problems, and many reports have been made thereon. (See, for example, patent documents 1 to 4).

The photosensitive layer of an electrophotographic photoreceptor which employs organic materials is obtained by dissolving a charge transport substance, a binder resin, etc. in a coating-fluid solvent and applying and drying the coating fluid obtained. The property required of the charge transport substance when this electrophotographic photoreceptor is produced is solubility in the coating-fluid solvent to be used for producing the coating fluid. In case where the charge transport substance has low solubility in the coating-fluid solvent, it may be impossible to dissolve a desired amount of the charge transport substance in the coating-fluid solvent or a coating fluid produced by dissolving the charge transport substance is thereafter apt to suffer a deterioration, e.g., precipitation. In addition, there are cases where after application for photosensitive-layer formation, crystals separate out in the coating film and where the poor solubility results in a decrease in the efficiency of production of the coating fluid and production of photoreceptors.

In general, compounds in which the π-electron system has been expanded within the molecule tend to have higher interaction between molecules and lower solubility as the molecular size increases. Tetraphenylbenzidine frameworks have a large molecular size and tend to have low solubility, and when such tetraphenylbenzidine framework is substituted with a styryl group or the like to expand the π-electron system within the molecule, the molecule size is further increased, resulting in lower solubility in coating-fluid solvents. Because of this, contrivances for ensuring solubility, such as newly introducing a substituent and handling a substance as a mixture of geometrical isomers, are being made in the reports mentioned above.

However, those techniques, when used alone, have had a problem that the spread of π-electrons in the molecule of the charge transport substance is reduced due to the influence of the substituent introduced in order to improve solubility and a problem that since a desired structure has been intentionally isomerized to obtain a mixture of geometrical isomers in order to ensure solubility, the composition as a whole has an ionization potential which is higher than a desired value, resulting in an increase in residual potential after exposure.

Meanwhile, since electrophotographic photoreceptors are repeatedly used in an electrophotographic process, i.e., the cycle including charging, exposure, development, transfer, cleaning, and erase, the photoreceptors undergo various kinds of stress during the use and deteriorate. Examples of chemical deteriorations, among such deteriorations, include the damage caused to the photosensitive layer by the ozone, which has high oxidizing properties, and NOx which are generated, for example, from the corona discharge device that is commonly used as a charging device. There are cases where this damage results in a decrease in charging property. These troubles are largely attributable to the chemical deterioration of the charge transport substance contained in a large amount in the photosensitive layer.

As a result of increases in speed in electrophotographic processes, an increase in sensitivity and high-speed responsiveness have become essential. In addition to these requirements, a prolongation of the life of photoreceptors is desired from the standpoint of reducing the burden of maintenance of printers, copiers, and the like. Resistance to various kinds of stress in electrophotographic processes is also becoming highly important.

PRIOR-ART DOCUMENTS

Patent Documents

Patent Document 1: JP-A-7-36203
Patent Document 2: JP-A-2002-80432
Patent Document 3: JP-A-2006-8670
Patent Document 4: JP-A-2008-83105

SUMMARY OF THE INVENTION

Problems that the Invention is to Solve

Although the reports mentioned above show charge transport substances which satisfy the properties concerning high sensitivity, high mobility, and low residual potential, the photosensitive layer is damaged by the ozone, which has high oxidizing properties, and NOx that are generated from the charging device. Consequently, the electrophotographic photoreceptor decreases in charging property and, hence, is poor in resistance to electrophotographic processes. There is presently no charge transport substance which satisfies the requirements for the current trends toward speed increase and full-color image formation in electrophotographic processes.

The invention has been achieved in view of the background-art techniques described above. Subjects for the invention are to provide a charge transport substance that shows a high mobility and a sufficient residual potential after exposure, which are necessary for a higher speed of response, and that is highly resistant to stress imposed in electrophotographic processes, and to provide an electrophotographic photoreceptor which contains the charge transport substance, has excellent high-speed responsiveness, shows a sufficient residual potential, and is highly resistant to stress imposed in electrophotographic processes, an electrophotographic cartridge, and an image-forming apparatus.

Means for Solving the Problems

The present inventors diligently made investigations and, as a result, have found that a charge transport substance having a specific structure has a high mobility, shows a sufficient residual potential after exposure, and is highly resistant to stress imposed in electrophotographic processes. The invention has been thus completed.

Namely, essential points of the invention reside in the following [1] to [7].

[1] A charge transport substance represented by the following formula (1):

[Chem. 1]

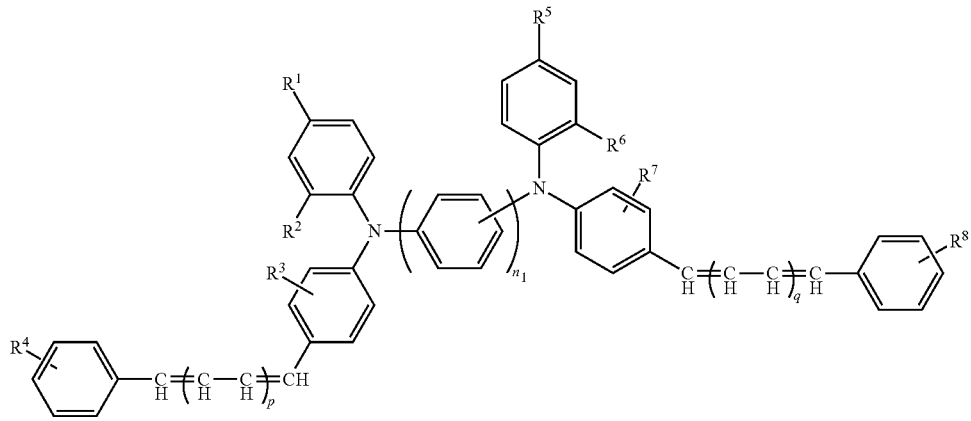

Formula (1)

wherein $R^1$, $R^2$, $R^5$, and $R^6$ each independently represent an alkyl group, $R^3$, $R^4$, $R^7$, and $R^8$ each independently represent a hydrogen atom, an alkyl group, an aryl group, or an alkoxy group, $n_1$ represents an integer of 1-5, and p and q each independently represent an integer of 0-2.

[2] An electrophotographic photoreceptor which comprises a conductive support and at least a photosensitive layer formed over the support, wherein the photosensitive layer contains a charge transport substance represented by the following formula (1):

[Chem. 2]

Formula (1)

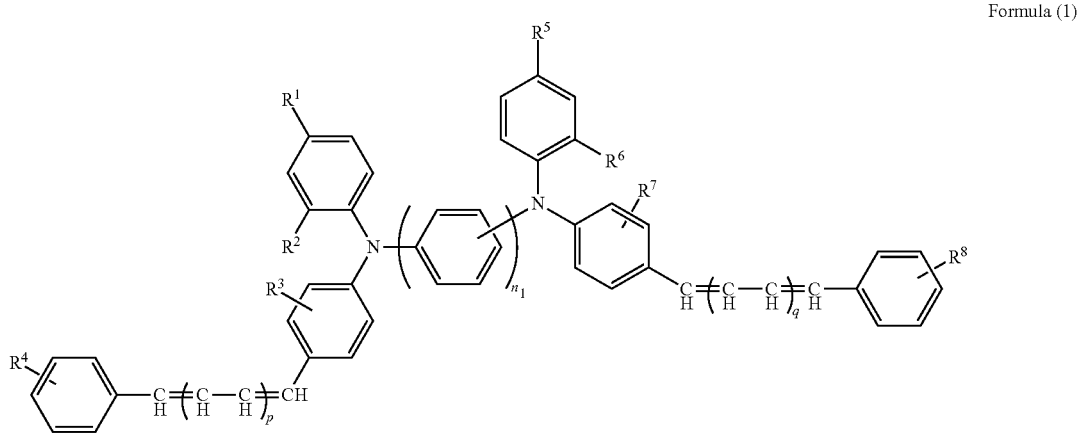

wherein $R^1$, $R^2$, $R^5$, and $R^6$ each independently represent an alkyl group, $R^3$, $R^4$, $R^7$, and $R^8$ each independently represent a hydrogen atom, an alkyl group, an aryl group, or an alkoxy group, $n_1$ represents an integer of 1-5, and p and q each independently represent an integer of 0-2.

[3] An electrophotographic photoreceptor which comprises a conductive support and at least a photosensitive layer formed over the support, wherein the photosensitive layer contains a compound represented by the following formula (2):

[Chem. 3]

Formula (2)

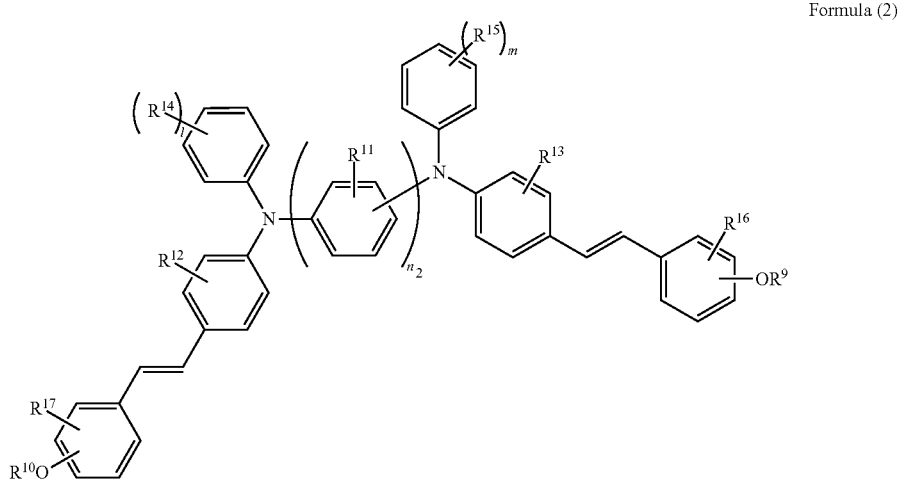

wherein $R^9$ and $R^{19}$ each independently represent an alkyl group, and $R^{11}$ to $R^{17}$ each independently represent a hydrogen atom, an alkyl group, an aryl group, or an alkoxy group, and $n_2$ represents an integer of 1-5, and l and m each independently represent an integer of 1-5.

[4] The electrophotographic photoreceptor according to the item [3] above, wherein the compounds represented by formula (2) are a positional-isomer mixture obtained by mixing compounds of different structures each represented by the formula (2).

[5] The electrophotographic photoreceptor according to any one of the items [2] to [4] above, wherein the photosensitive layer contains oxytitanium phthalocyanine having a crystal form which, when examined by X-ray powder diffractometry using a CuKα characteristic X-ray line, gives a spectrum which shows diffraction peaks at Bragg angles (2θ±0.2°) of at least 24.1° and 27.2°.

[6] An electrophotographic photoreceptor cartridge which comprises: the electrophotographic photoreceptor according to any one of the items [2] to [5] above; and at least one device selected from the group consisting of a charging device which charges the electrophotographic photoreceptor, an exposure device which exposes the charged electrophotographic photoreceptor to light to form an electrostatic latent image, and a developing device which develops the electrostatic latent image formed on the electrophotographic photoreceptor.

[7] An image-forming apparatus which comprises: the electrophotographic photoreceptor according to any one of the items [2] to [5] above; a charging device which charges the electrophotographic photoreceptor; an exposure device which exposes the charged electrophotographic photoreceptor to light to form an electrostatic latent image; and a developing device which develops the electrostatic latent image formed on the electrophotographic photoreceptor.

Effects of the Invention

The charge transport substance of the invention has a high mobility and shows a sufficient residual potential after exposure. Consequently, the electrophotographic photoreceptor employing the charge transport substance of the invention not only can have excellent high-speed responsiveness and residual potential but also can attain high resistance to stress imposed in electrophotographic processes.

MODES FOR CARRYING OUT THE INVENTION

Figure 1:
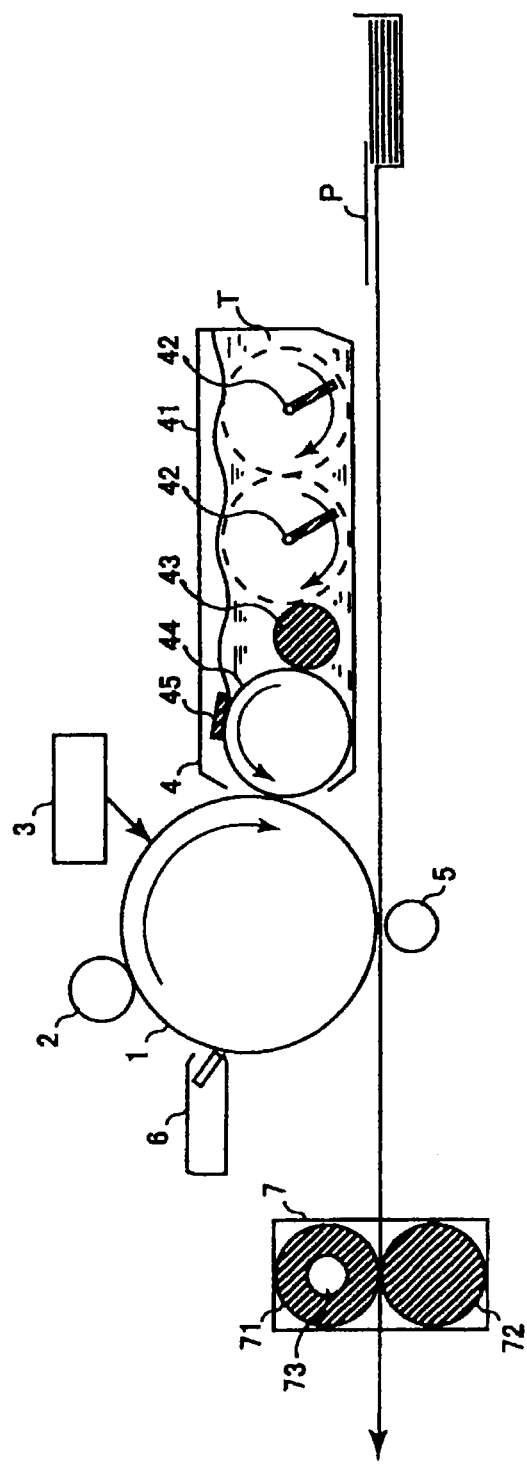
FIG. 1 is a diagrammatic view which illustrates the configuration of important parts of one embodiment of the image-forming apparatus of the invention.

Modes for carrying out the invention are explained below in detail. However, the following explanations on constituent elements are for representative embodiments of the invention, and the embodiments can be suitably modified unless the modifications depart from the spirit of the invention. In this description, all percents and parts given in terms of mass are the same as the percents and parts given in weight.

<<Charge Transport Substance>>

<Structure of Charge Transport Substance According to First Aspect>

The charge transport substance according to the first aspect of the invention may be any compound represented by the following formula (1).

[Chem. 4]

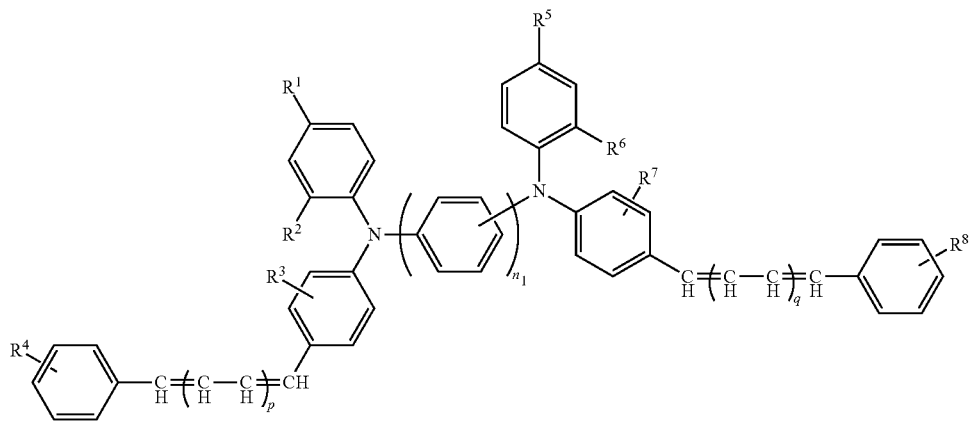

Formula (1)

(In formula (1), $R^1$, $R^2$, $R^5$, and $R^6$ each independently represent an alkyl group, $R^3$, $R^4$, $R^7$, and $R^8$ each independently represent a hydrogen atom, an alkyl group, an aryl group, or an alkoxy group, $n_1$ represents an integer of 1-5, and p and q each independently represent an integer of 0-2.)

In formula (1), $R^1$, $R^2$, $R^5$, and $R^6$ each independently represent an alkyl group. Specifically, examples thereof include linear alkyl groups such as methyl, ethyl, n-propyl, and n-butyl, branched alkyl groups such as isopropyl and ethylhexyl, and cycloalkyl groups such as cyclohexyl. Preferred of these alkyl groups are alkyl groups having 1-8 carbon atoms, from the standpoint of the suitability of starting materials for general-purpose use. From the standpoint of handleability during production, alkyl groups having 1-4 carbon atoms are more preferred. From the standpoint of the photo-decay characteristics of the electrophotographic photoreceptor, the alkyl groups having 1-2 carbon atoms are even more preferred. Methyl is especially preferred from the standpoint of the charge-transporting ability of the charge transport substance.

In formula (1), $R^3$ and $R^7$ each independently represent a hydrogen atom, an alkyl group, an aryl group, or an alkoxy group. Specifically, examples of the alkyl group include linear alkyl groups such as methyl, ethyl, n-propyl, and n-butyl, branched alkyl groups such as isopropyl and ethylhexyl, and cycloalkyl groups such as cyclohexyl. Examples of the aryl group include phenyl and naphthyl groups which may have a substituent. Examples of the alkoxy group include linear alkoxy groups such as methoxy, ethoxy, n-propoxy, and n-butoxy, branched alkoxy groups such as isopropoxy and ethylhexyloxy, and cyclohexyloxy. Preferred of these are hydrogen atom, alkyl groups having 1-8 carbon atoms, and alkoxy groups having 1-8 carbon atoms, from the standpoint of the suitability of starting materials for general-purpose use. More preferred from the standpoint of handleability during production are hydrogen atom, alkyl groups having 1-6 carbon atoms, and alkoxy groups having 1-6 carbon atoms. Even more preferred from the standpoint of the photo-decay characteristics of the electrophotographic photoreceptor are hydrogen atom and the alkyl groups having 1-2 carbon atoms. Hydrogen atom is especially preferred from the standpoint of the charge-transporting ability of the charge transport substance.

In formula (1), $R^4$ and $R^8$ each independently represent a hydrogen atom, an alkyl group, an aryl group, or an alkoxy group. Specifically, examples of the alkyl group include linear alkyl groups such as methyl, ethyl, n-propyl, and n-butyl, branched alkyl groups such as isopropyl and ethylhexyl, and cycloalkyl groups such as cyclohexyl. Examples of the aryl group include phenyl and naphthyl groups which may have a substituent. Examples of the alkoxy group include linear alkoxy groups such as methoxy, ethoxy, n-propoxy, and n-butoxy, branched alkoxy groups such as isopropoxy and ethylhexyloxy, and cyclohexyloxy. Preferred of these are hydrogen atom, alkyl groups having 1-8 carbon atoms, and alkoxy groups having 1-8 carbon atoms, from the standpoint of the suitability of starting materials for general-purpose use. More preferred from the standpoint of the photo-decay characteristics of the electrophotographic photoreceptor are alkyl groups having 1-4 carbon atoms and alkoxy groups having 1-4 carbon atoms. Even more preferred from the standpoint of the ozone resistance of the electrophotographic photoreceptor are hydrogen atom and alkyl groups having 1-4 carbon atoms. Especially preferred from the standpoint of the charge-transporting ability of the charge transport substance are hydrogen atom and the alkyl groups having 1-2 carbon atoms.

In formula (1), $n_1$ represents an integer of 1-5. From the standpoint of improving the solubility in coating-fluid solvents, $n_1$ is preferably 4 or less. From the standpoint of the charge-transporting ability of the charge transport substance, $n_1$ is more preferably 3 or less. From the standpoint of the photo-decay characteristics of the electrophotographic photoreceptor, $n_1$ is even more preferably 2 or less. Meanwhile, from the standpoint of inhibiting the electrophotographic photoreceptor from decreasing in charging property, $n_1$ is preferably 2 or larger.

In formula (1), p and q each independently represent an integer of 0-2. From the standpoint of improving the solubility of the charge transport substance in coating-fluid solvents, it is preferred that p and q each independently be 0-1.

In formula (1), the arylene moiety to which the diphenylamino groups have been bonded represents an unsubstituted phenylene group when $n_1=1$, an unsubstituted biphenylene group when $n_1=2$, an unsubstituted terphenylene group when $n_1=3$, an unsubstituted quaterphenylene group when $n_1=4$, and an unsubstituted quinquephenylene group when $n_1=5$. The positions at which the two diphenylamino groups have been bonded to the arylene group are not limited unless the effects of the invention are considerably lessened. However, when $n_1=1$, it is preferred, from the standpoint of the charging properties of the electrophotographic photoreceptor, that the two diphenylamino groups should be bonded to the phenylene group at meta positions to each other. When $n_1=2$, it is preferred, from the standpoint of the charge-transporting ability of the charge transport substance, that the two diphenylamino groups should be bonded at the 4- and 4'-positions of the biphenylene group. When $n_1=3$, the terphenylene group is preferably a p-terphenylene group from the standpoint of the suitability of starting materials for general-purpose use, and it is preferred, from the standpoint of the charge-transporting ability of the charge transport substance, that the diphenylamine groups should be bonded to the p-terphenylene group at the 4- and 4"-positions. When $n_1=4$, the quaterphenylene group is preferably a p-quaterphenylene group from the standpoint of the suitability of starting materials for general-purpose use, and it is preferred, from the standpoint of the charge-transporting ability of the charge transport substance, that the diphenylamine groups should be bonded to the p-quaterphenylene group at the 4- and 4'''-positions. When $n_1=5$, the quinquephenylene group is preferably a p-quinquephenylene group from the standpoint of the suitability of starting materials for general-purpose use, and it is preferred, from the standpoint of the charge-transporting ability of the charge transport substance, that the diphenylamine groups should be bonded to the p-quinquephenylene group at the 4- and 4''''-positions.

Examples of the structures of charge transport substances suitable for the first aspect of the invention are shown below. The following structures are examples for a more detailed understanding of the invention, and the structure of the charge transport substance should not be construed as being limited to the following structures unless these structures depart from the spirit of the invention.

[Chem. 5]

CT1-1

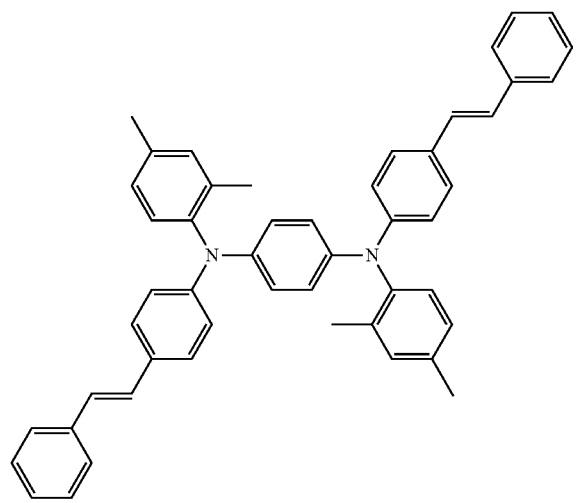

-continued
CT1-2
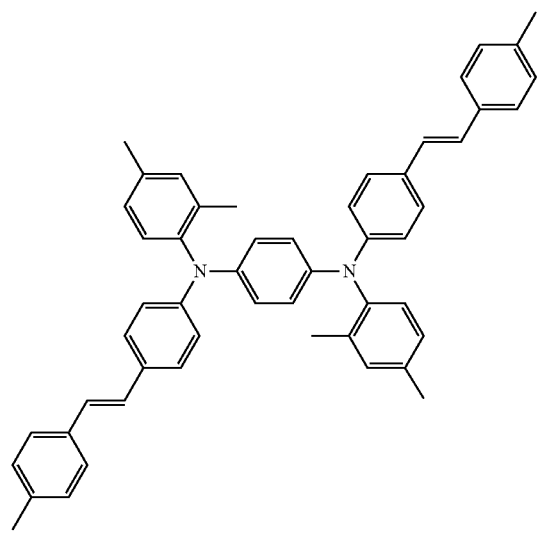
CT1-3
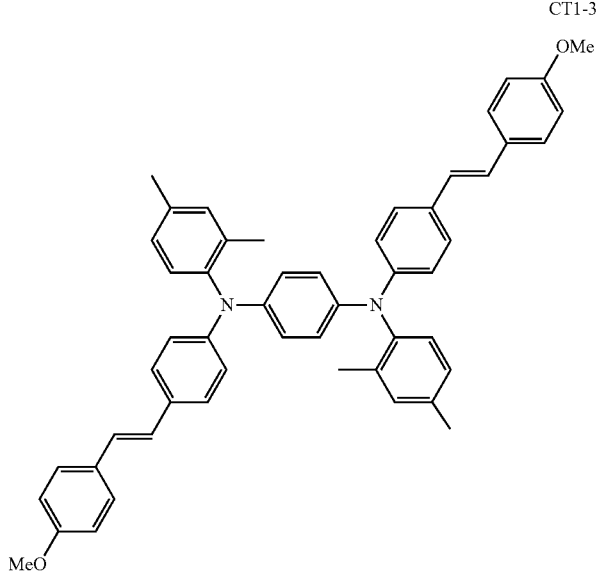
CT1-4
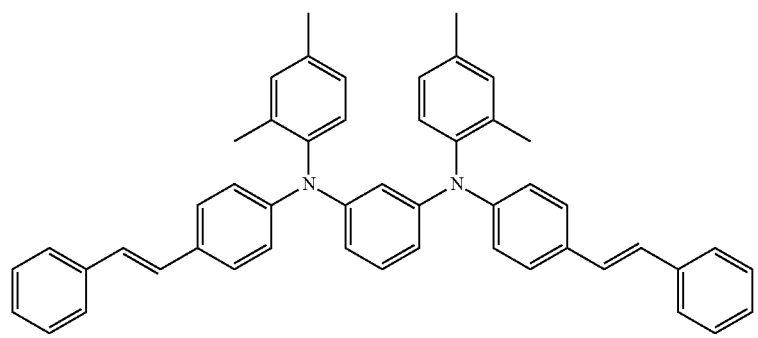
CT1-5
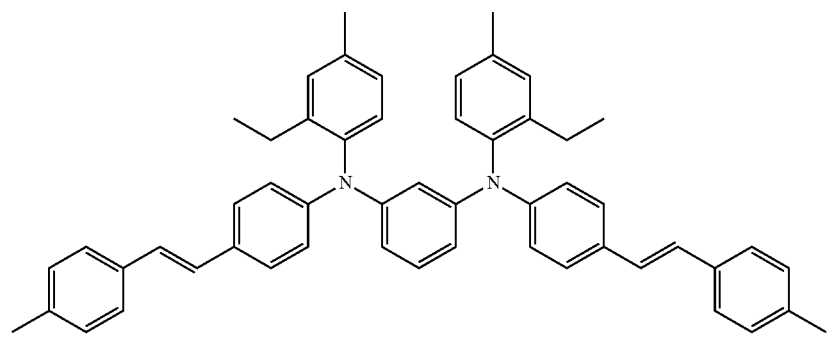
CT1-6
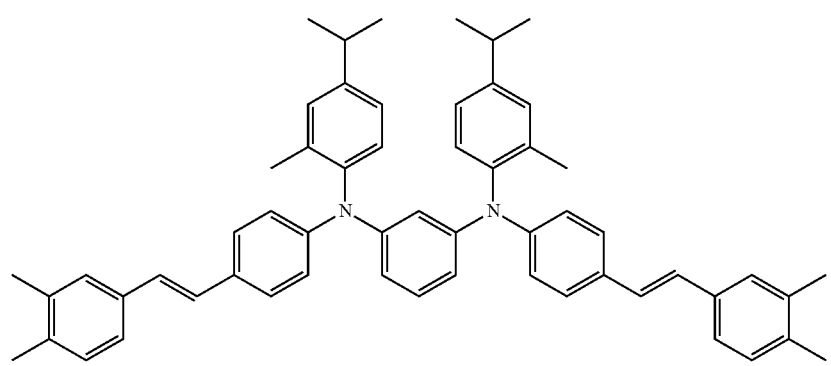

CT1-7
CT1-8
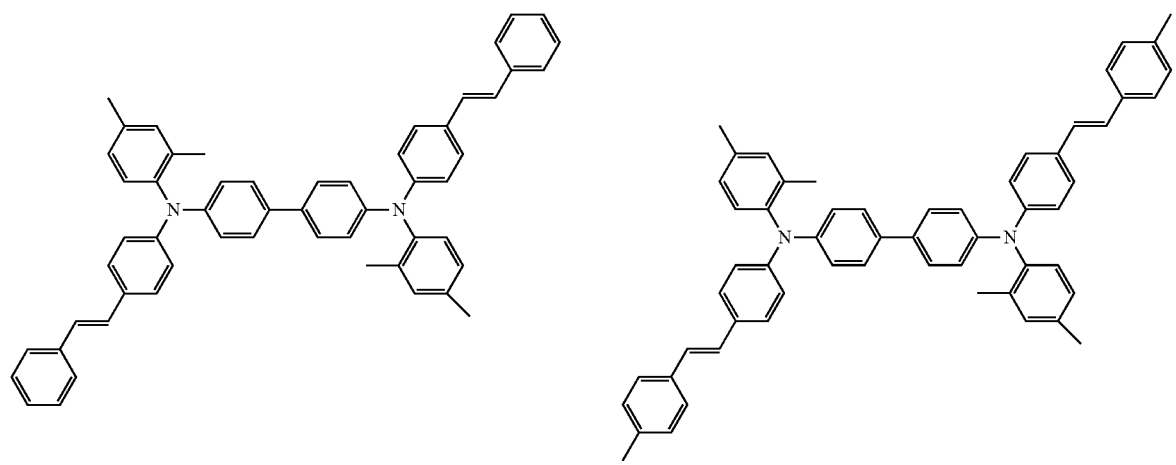
[Chem. 6]
CT1-9
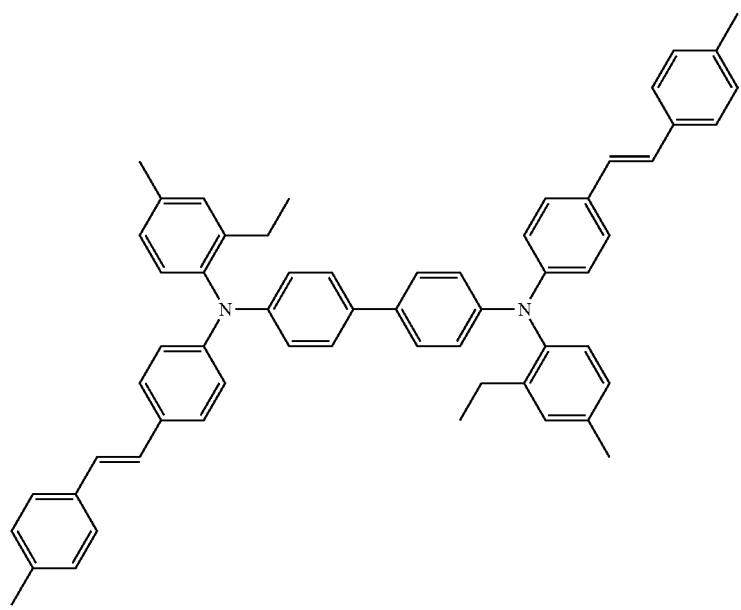

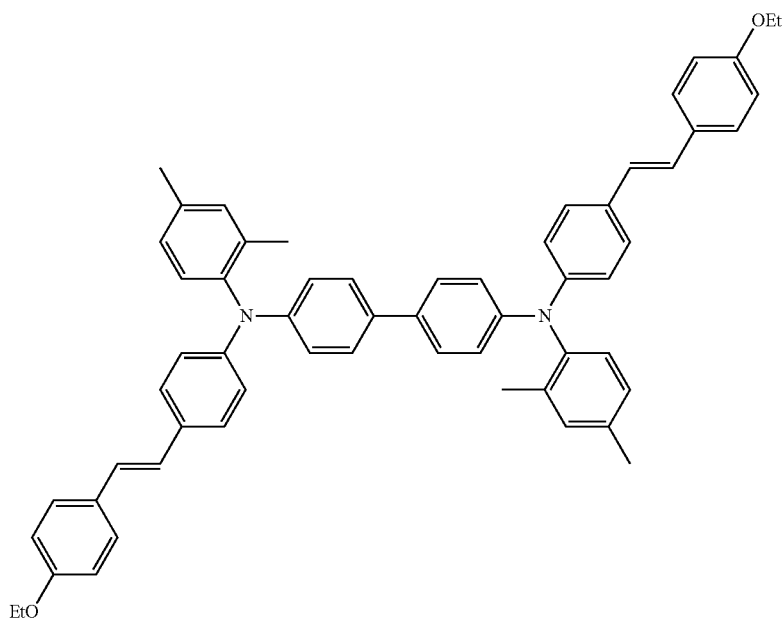
CT1-10
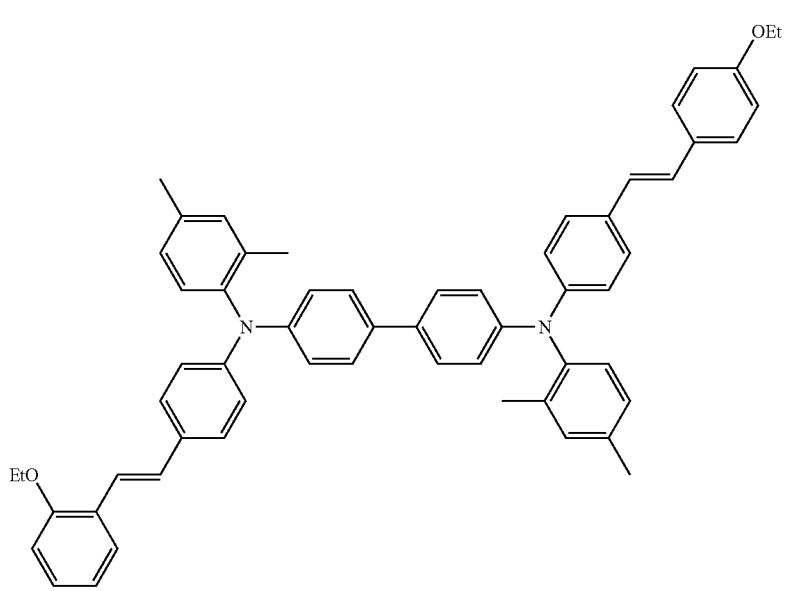
CT1-11

-continued
CT1-12
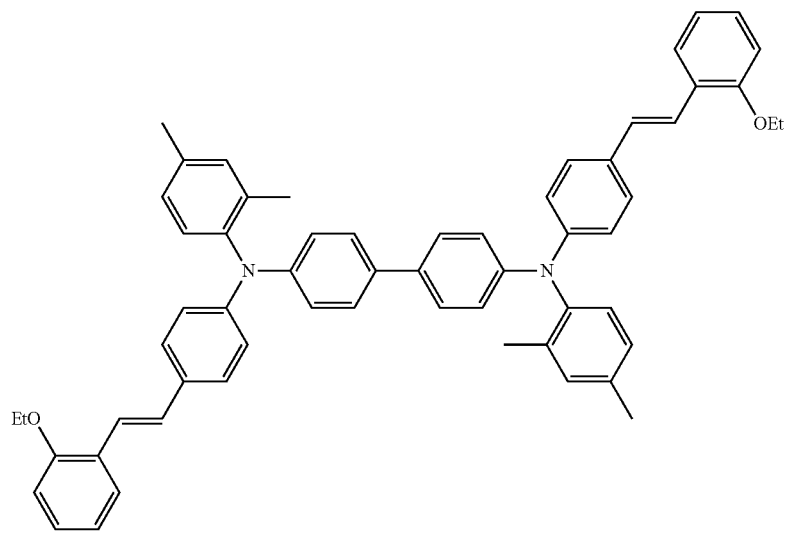
CT1-13
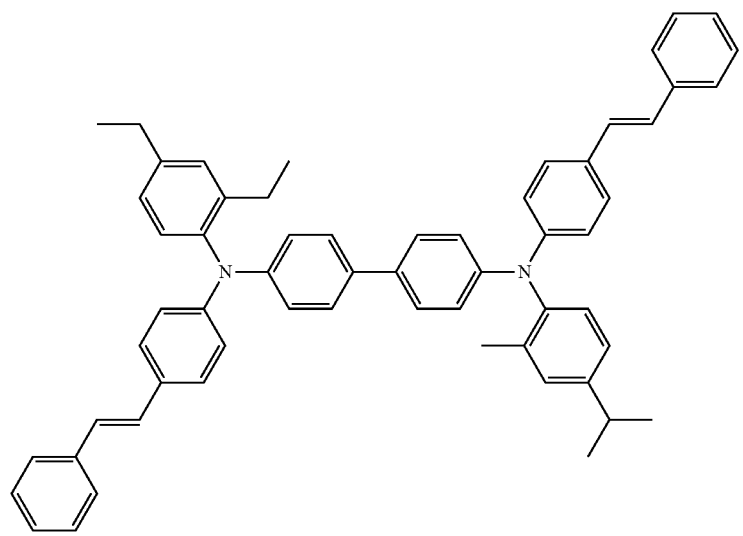
CT1-14
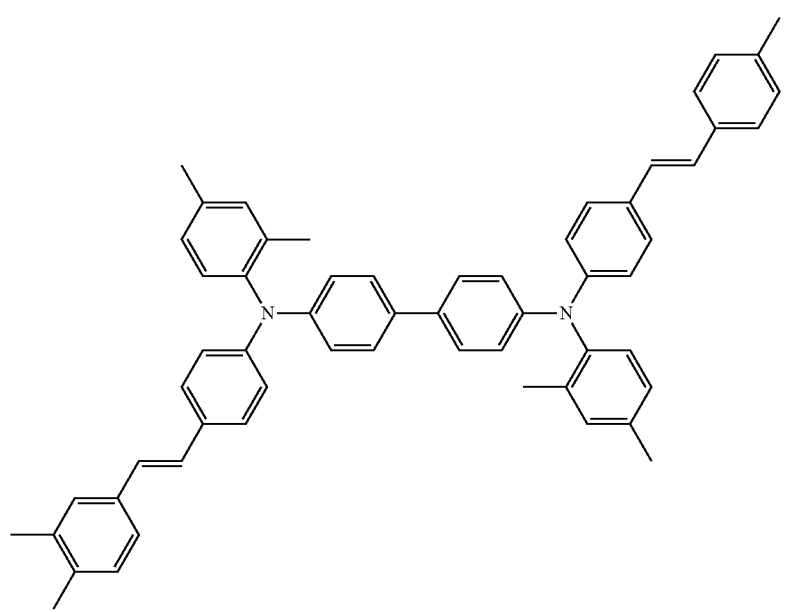

-continued
CT1-15
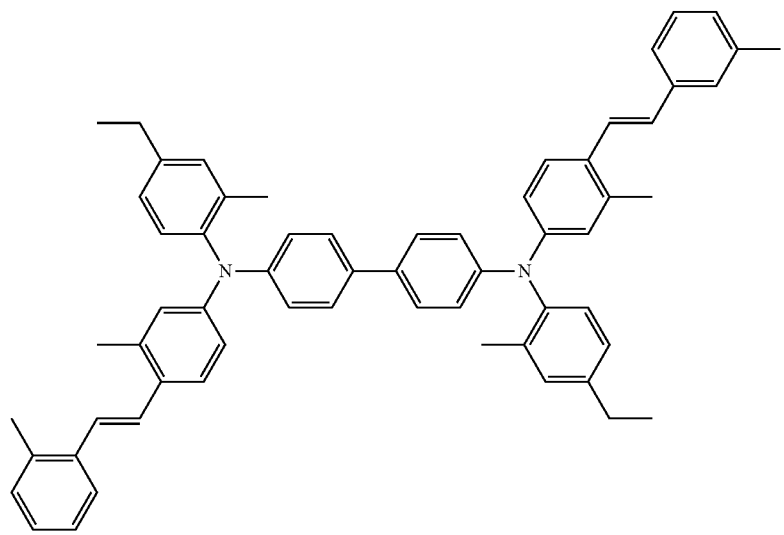
CT1-16
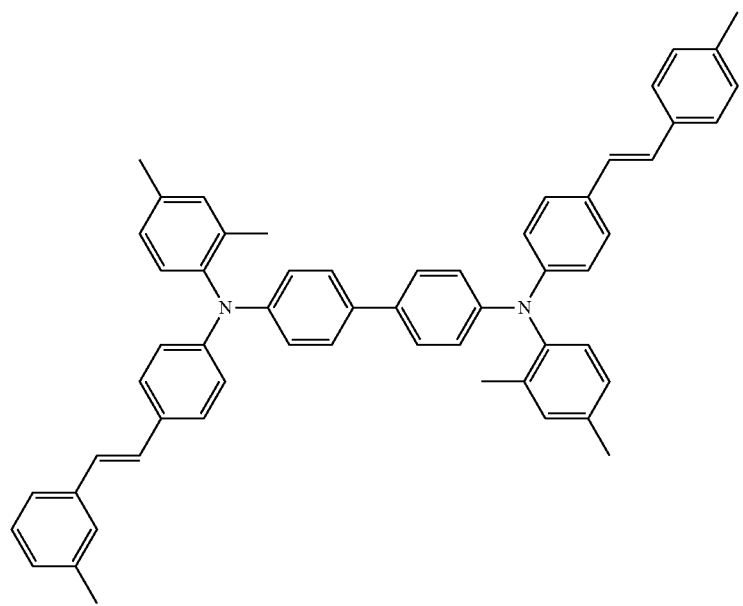

-continued
[Chem. 7]
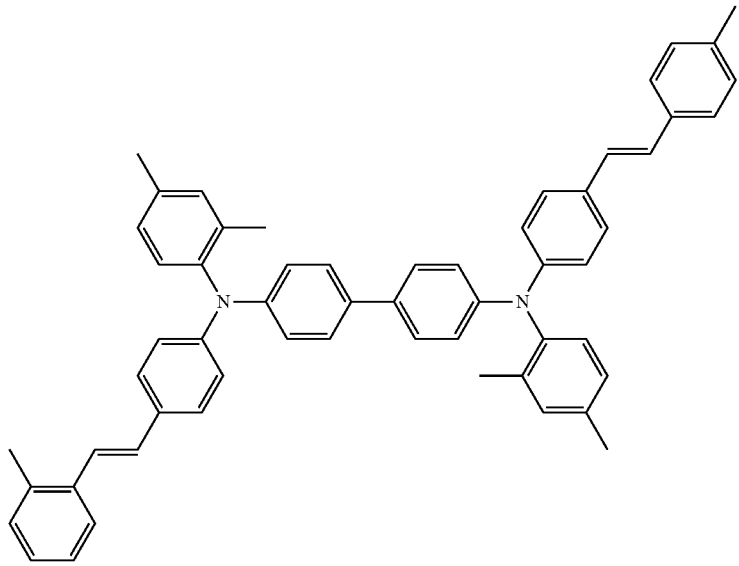
CT1-17
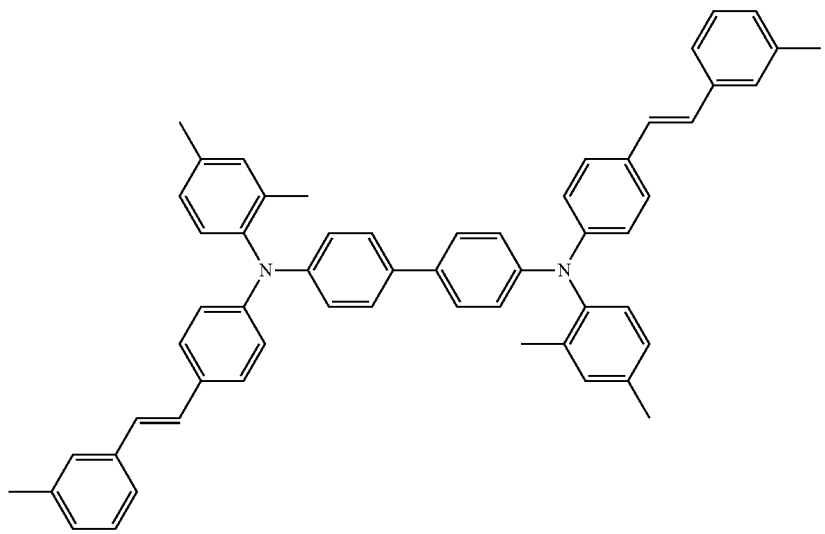
CT1-18
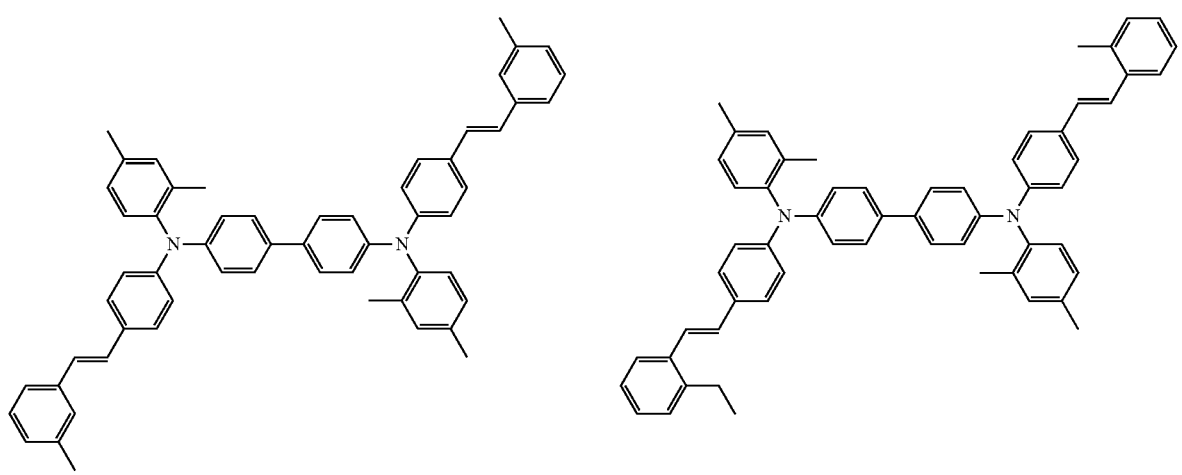
CT1-19 CT1-20

CT1-21
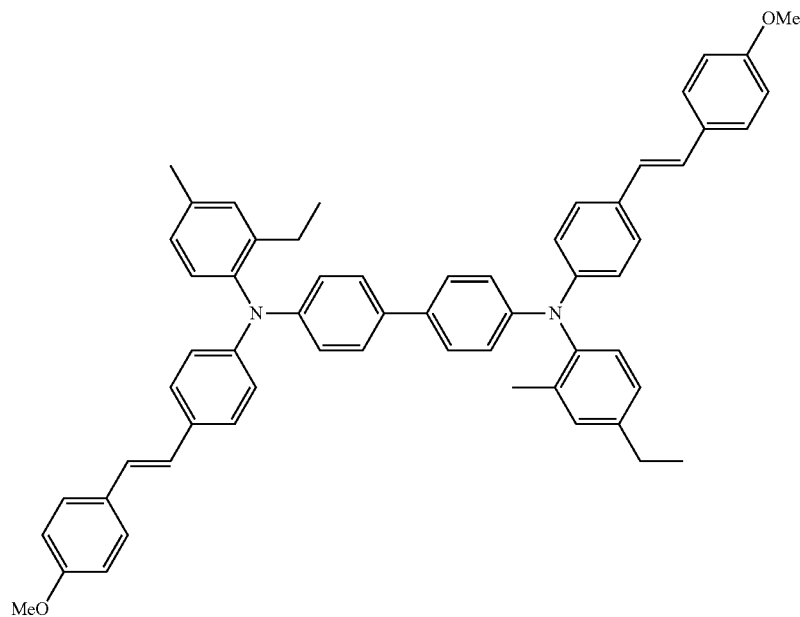
CT1-22
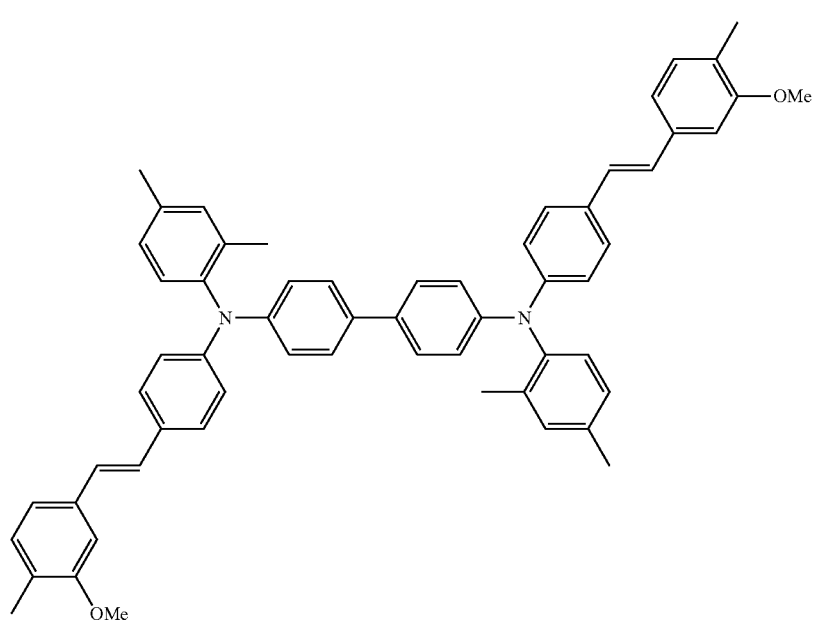

-continued
CT1-23
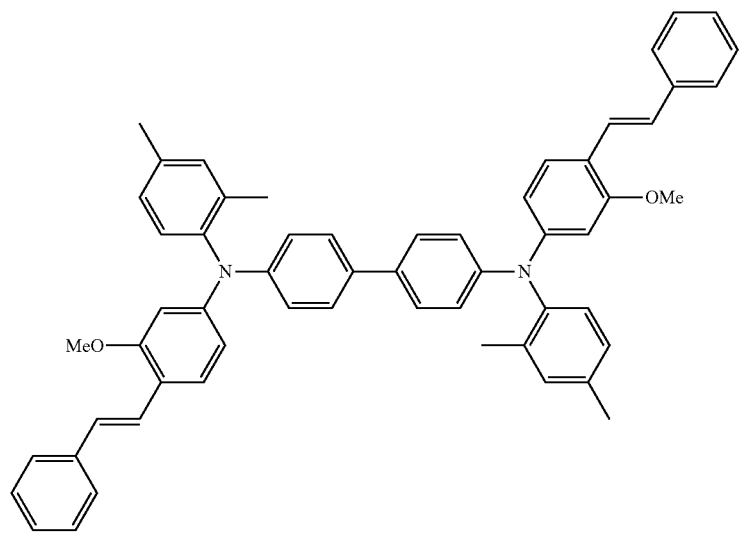
CT1-24
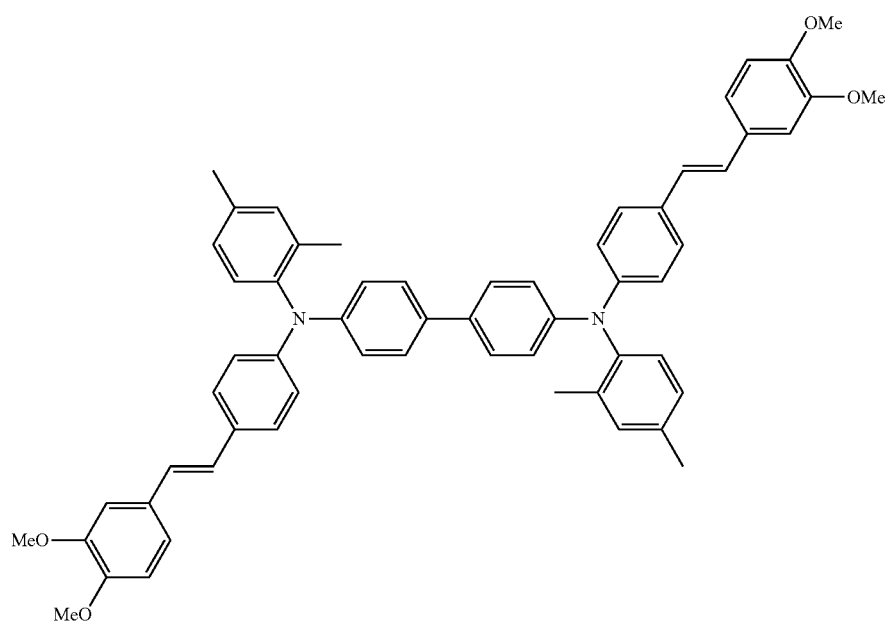

[Chem. 8]
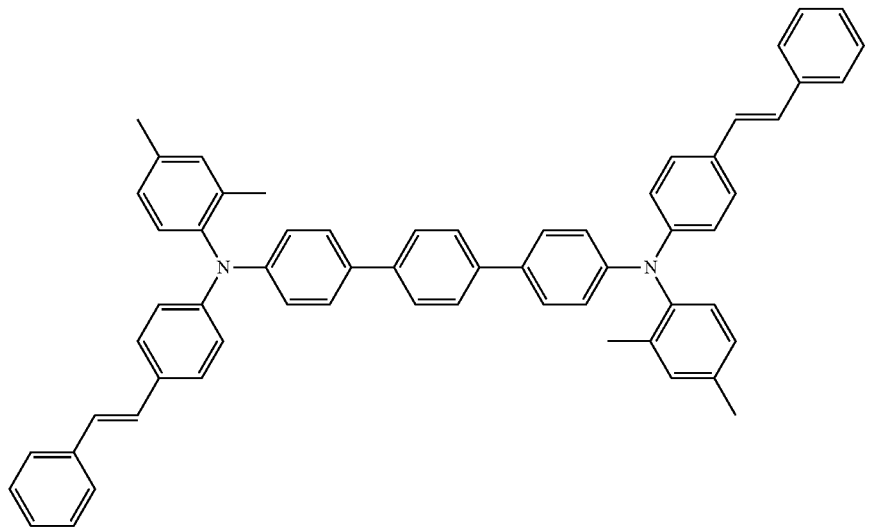
CT1-25
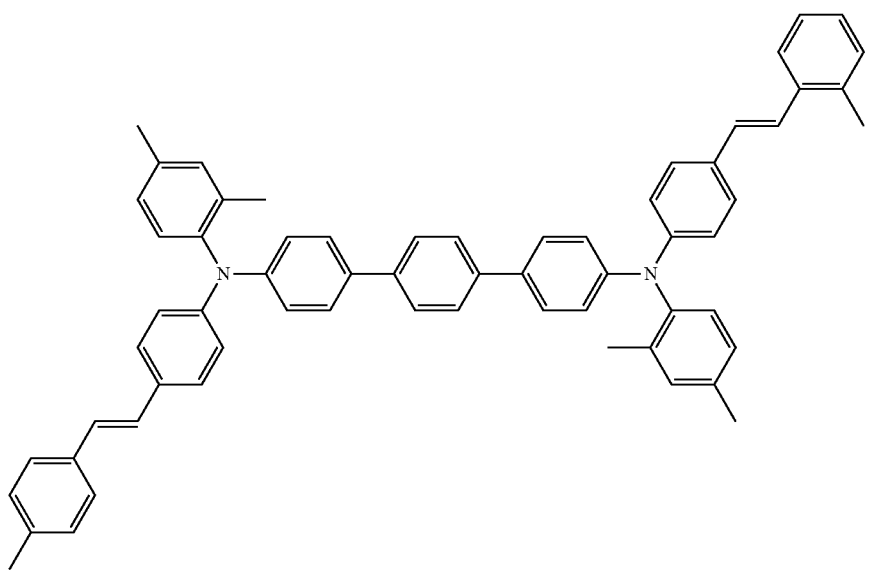
CT1-26

-continued
CT1-27
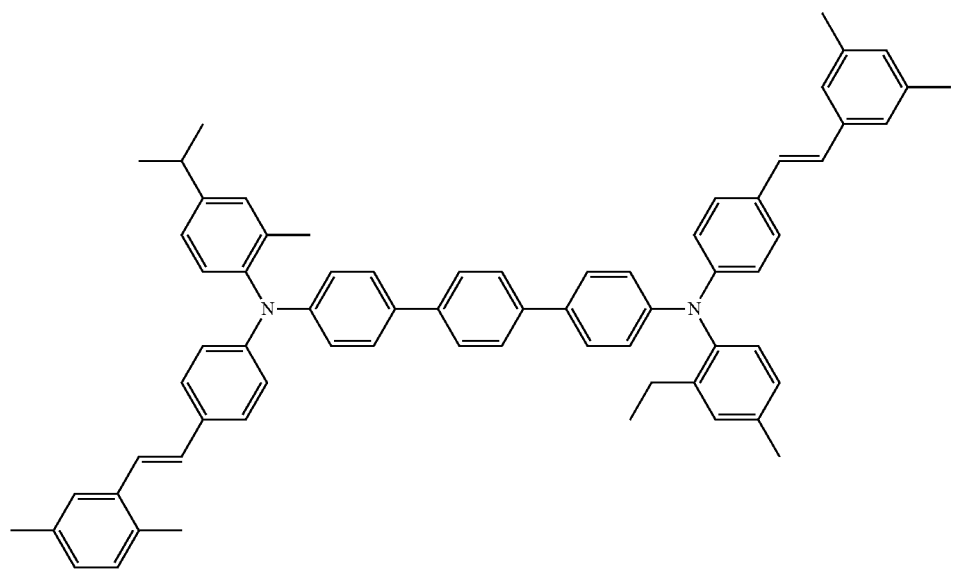
CT1-28
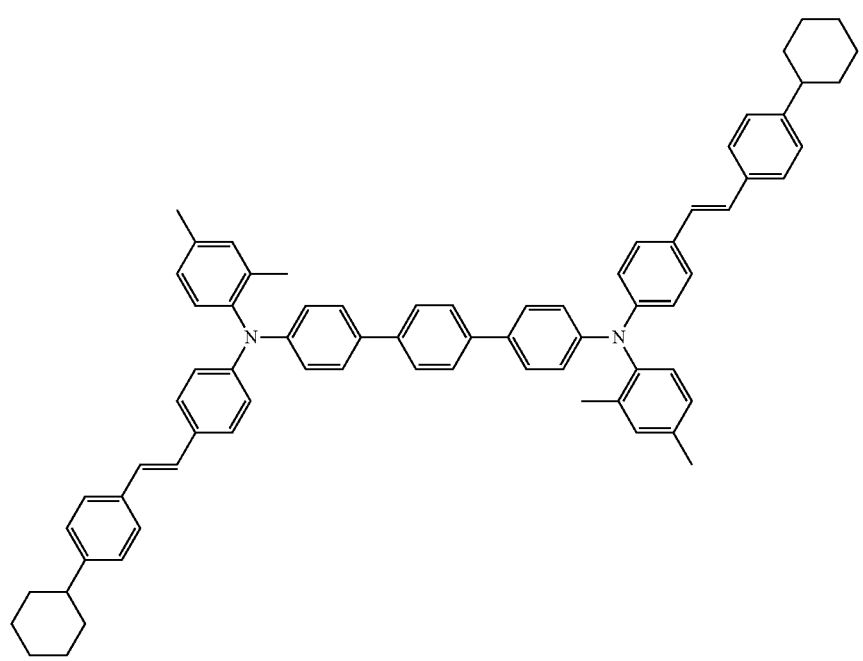

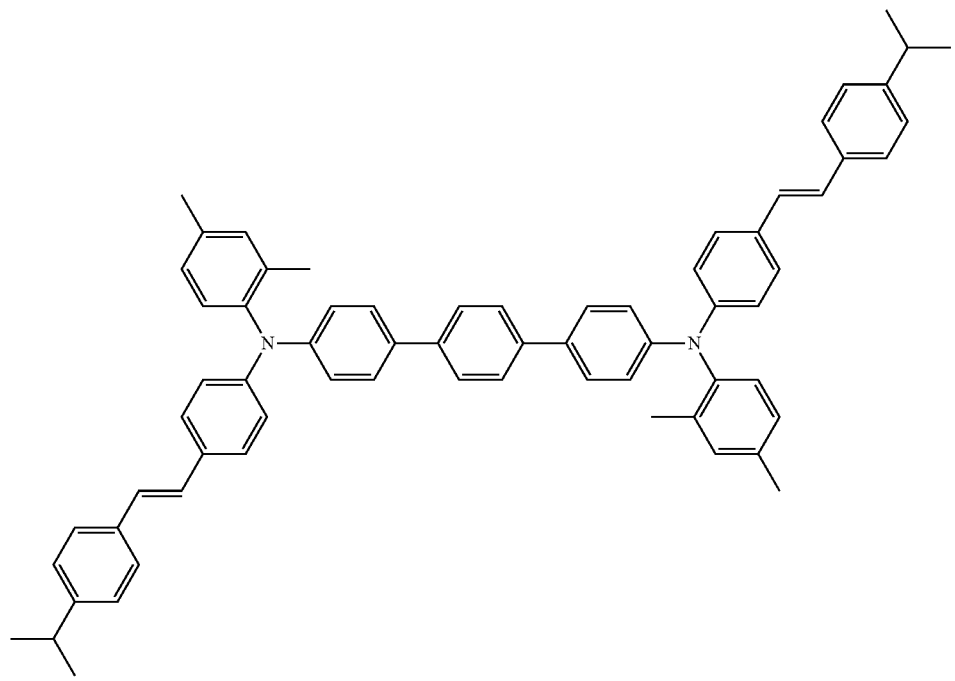
CT1-29
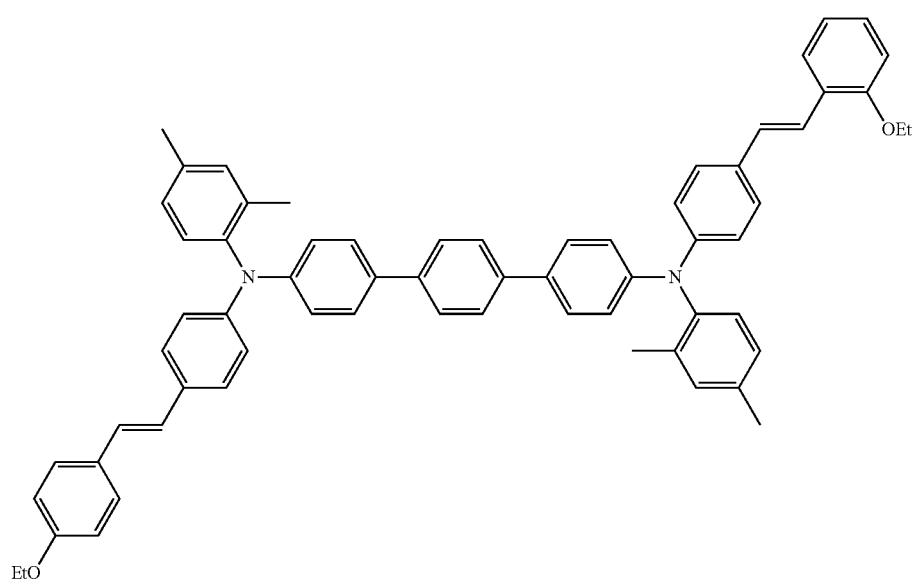
CT1-30

CT1-31
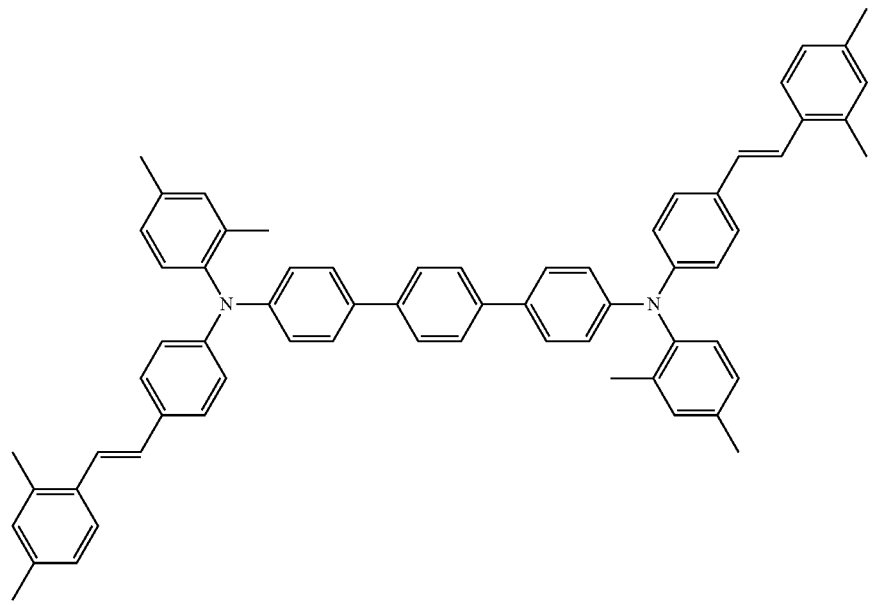
CT1-32
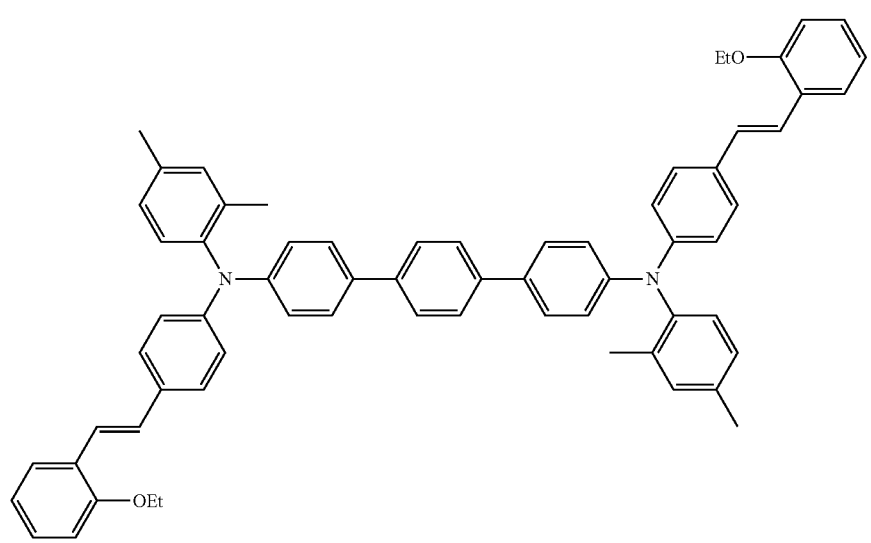

CT1-33
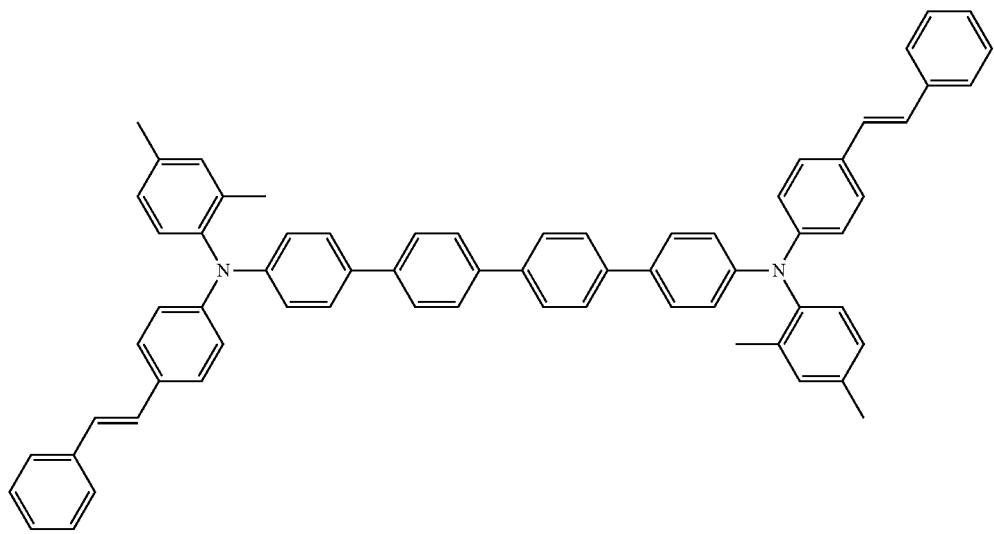
CT1-34
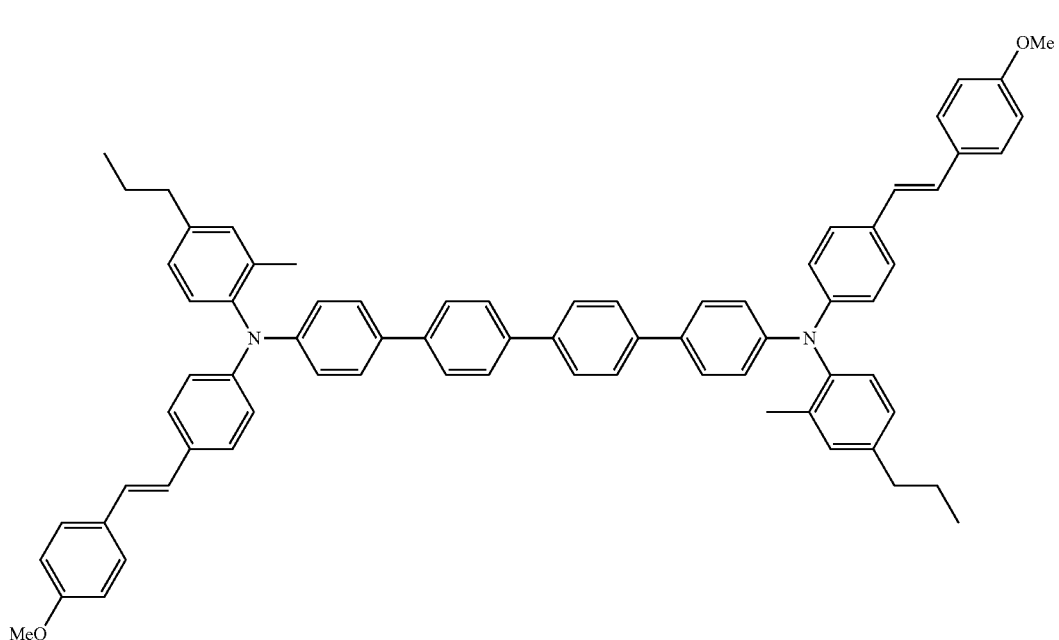

CT1-35
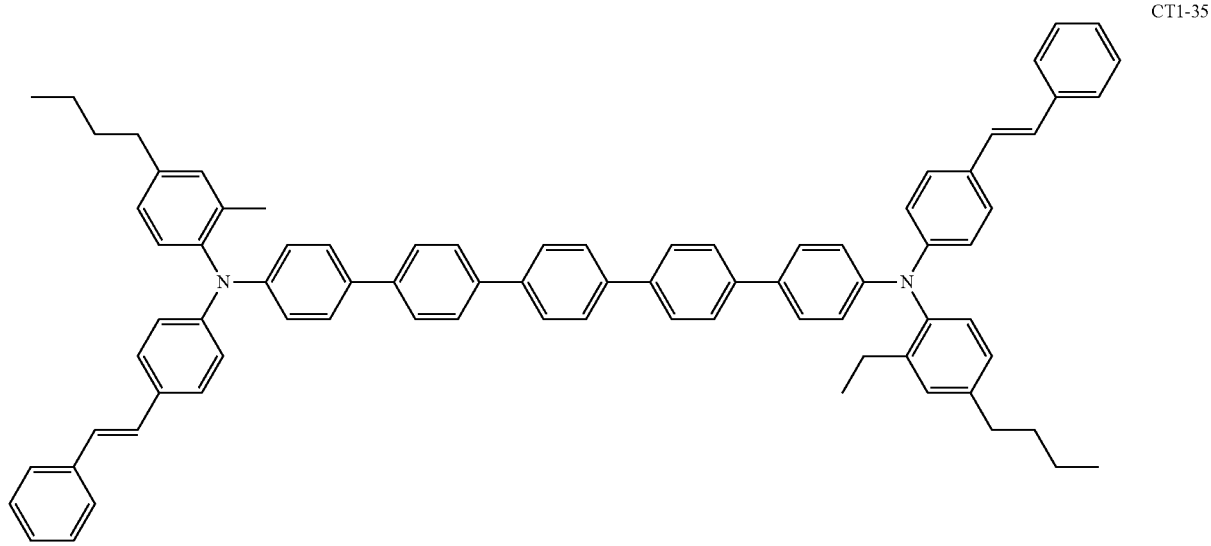
CT1-36
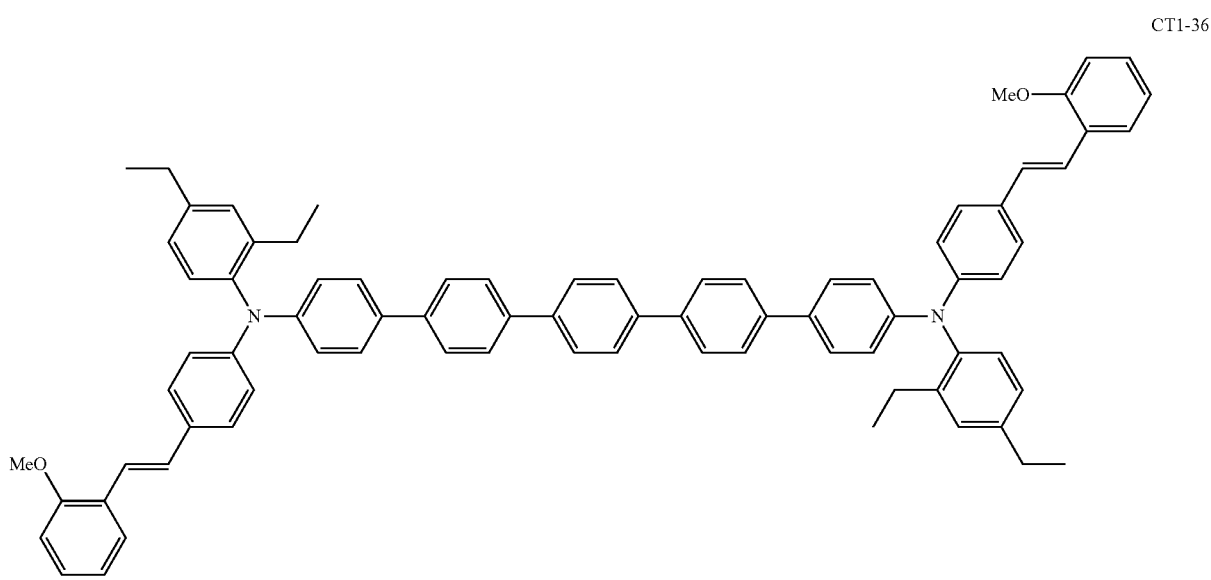
[Chem. 10]
CT1-37
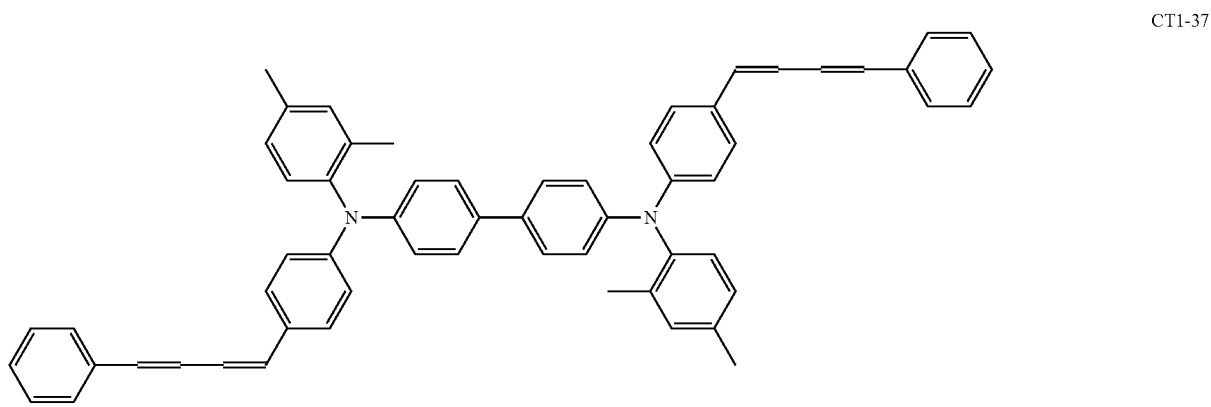

-continued
CT1-38
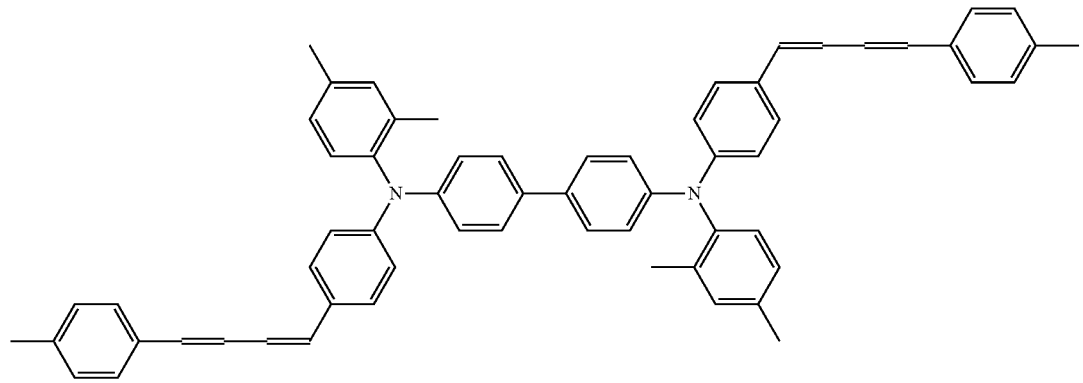
CT1-39
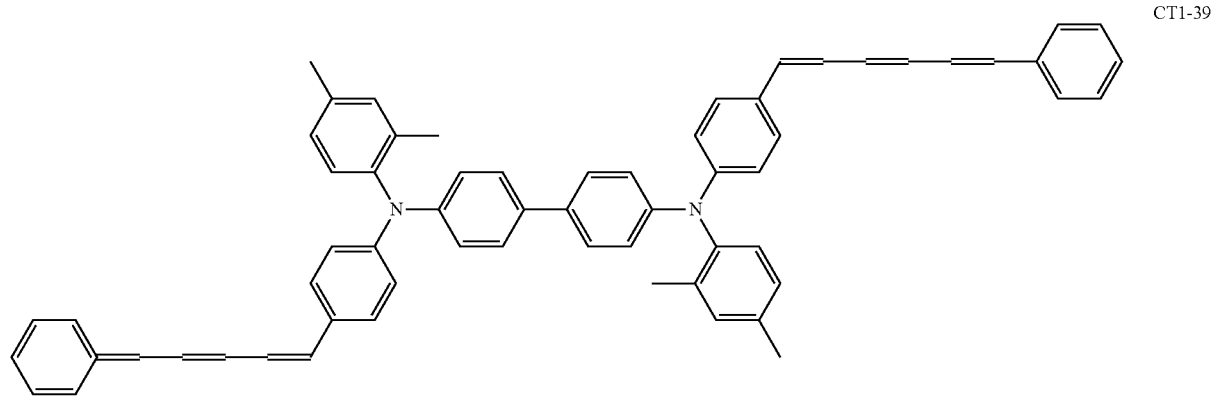
CT1-40
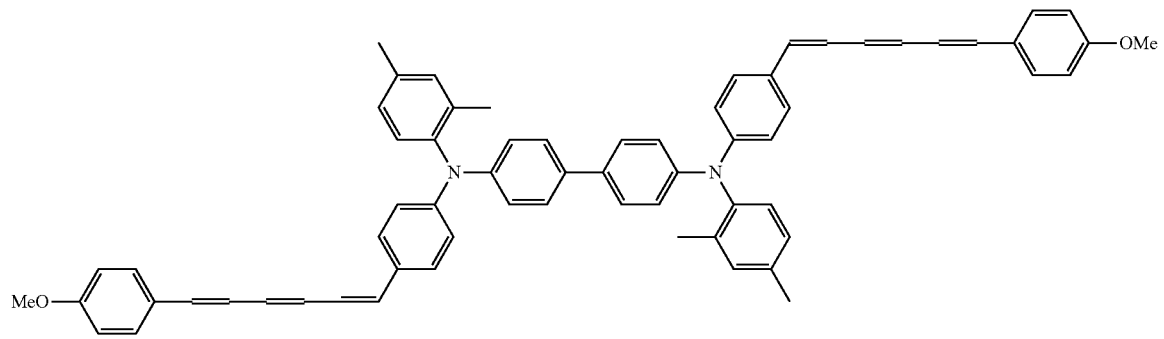
CT1-41
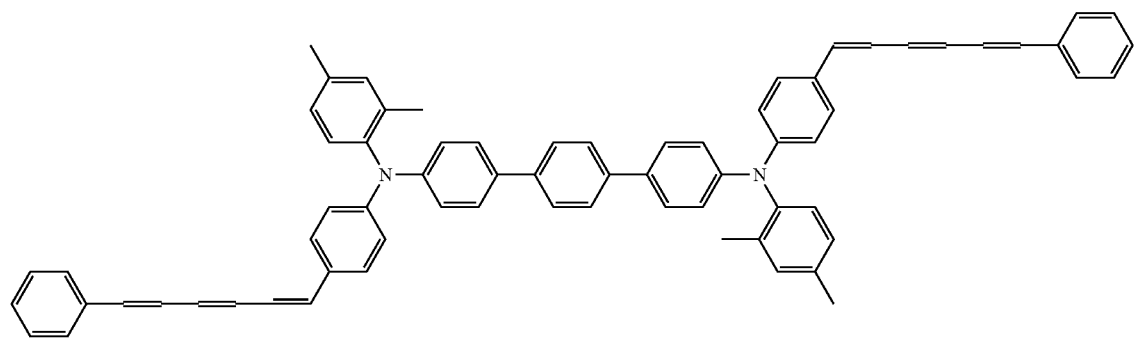

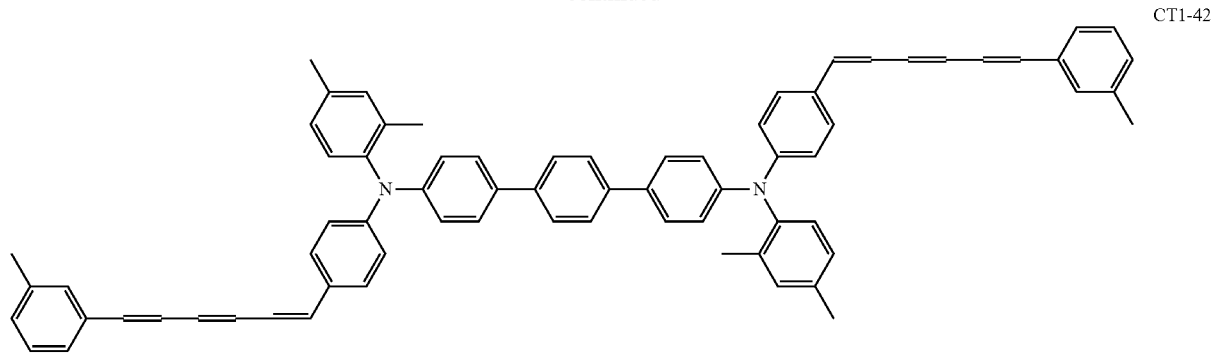

<Processes for Producing Charge Transport Substance According to First Aspect>

The charge transport substances CT1-1 to CT1-42 shown above as examples can be easily synthesized by known methods. For example, the example compound CT1-8 can be produced in accordance with the scheme shown below.

[Chem. 11]

For example, the compound can be produced by formylating a compound having a tetraphenylbenzidine framework by, for example, the Vilsmeier reaction and then reacting the formylated compound with a phosphoric ester compound to introduce styryl groups thereinto (scheme 1).

(Scheme 1)

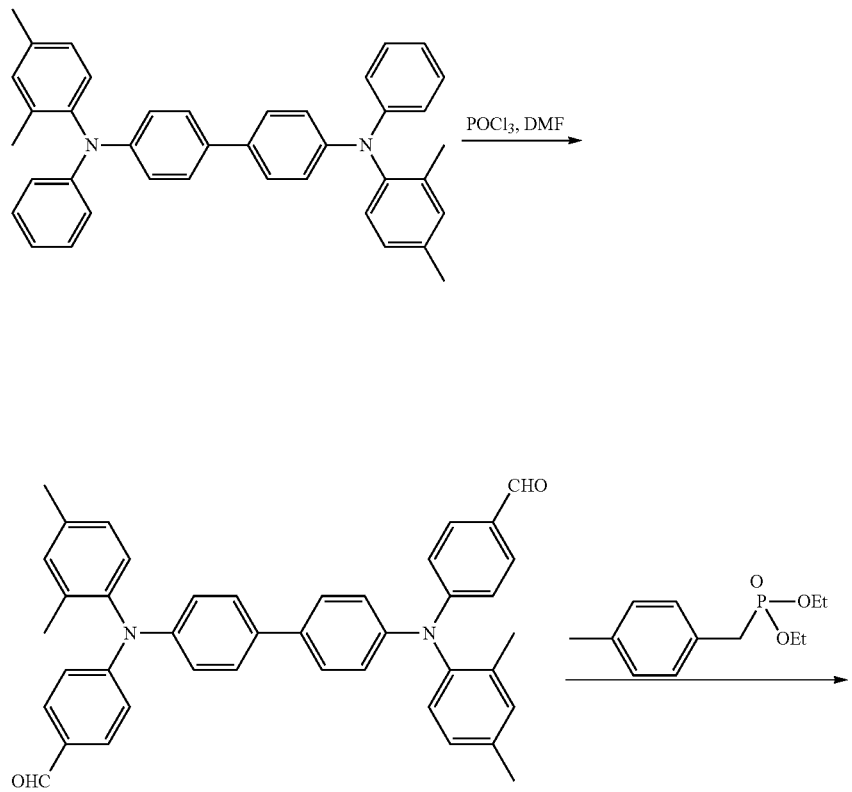

-continued
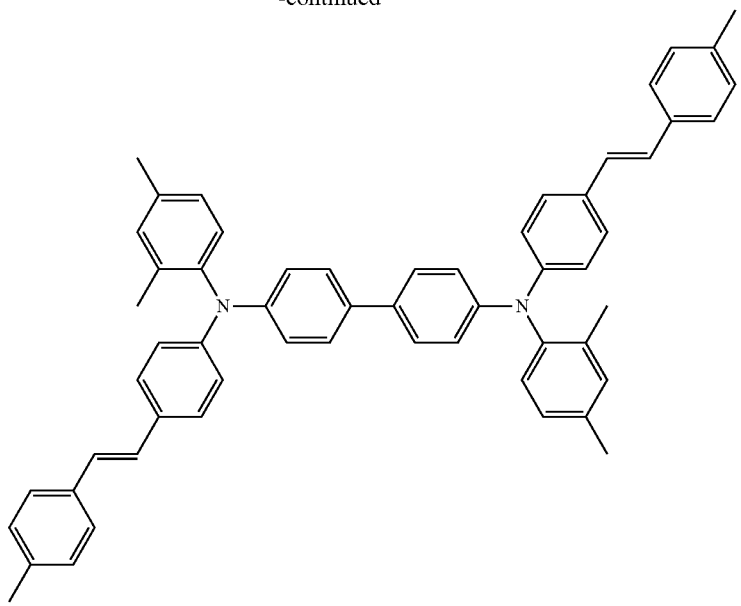
In another production process, an N,N'-diphenylbenzidine compound is subjected to coupling reaction with a halogenated stilbene compound. Thus, the desired compound can be produced (scheme 2).
(Scheme 2)
[Chem. 12]
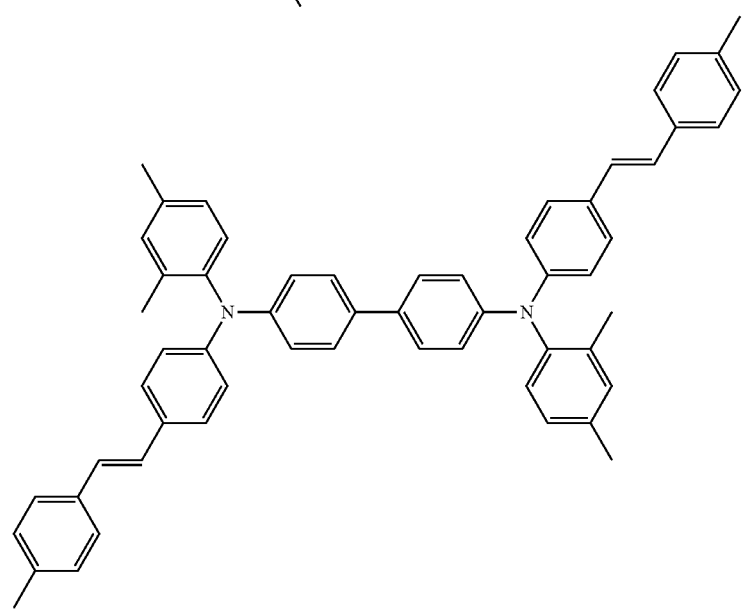

<Structure of Charge Transport Substance According to Second Aspect>

The charge transport substance according to the second aspect of the invention may be any compound represented by the following formula (2).

[Chem. 13]

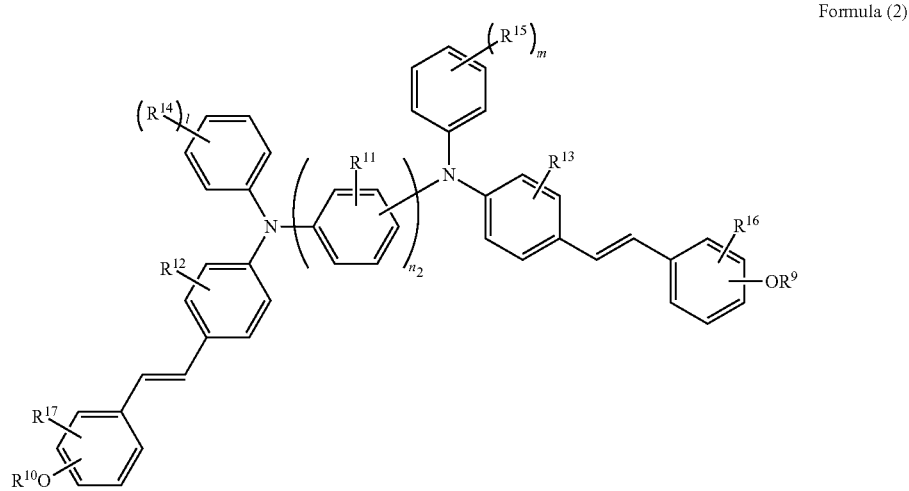

Formula (2)

(In formula (2), $R^9$ and $R^{10}$ each independently represent an alkyl group, and $R^{11}$ to $R^{17}$ each independently represent a hydrogen atom, an alkyl group, an aryl group, or an alkoxy group. Symbol $n_2$ represents an integer of 1-5, and l and m each independently represent an integer of 1-5.)

In formula (2), $R^9$ and $R^{10}$ each independently represent an alkyl group. Specifically, examples thereof include linear alkyl groups such as methyl, ethyl, n-propyl, and n-butyl, branched alkyl groups such as isopropyl and ethylhexyl, and cycloalkyl groups such as cyclohexyl. Preferred of these alkyl groups are alkyl groups having 1-8 carbon atoms, from the standpoint of the suitability of starting materials for general-purpose use. From the standpoint of handleability during production, alkyl groups having 1-6 carbon atoms are more preferred. From the standpoint of the photo-decay characteristics of the electrophotographic photoreceptor, alkyl groups having 1-4 carbon atoms are even more preferred. Especially preferred from the standpoint of the charge-transporting ability of the charge transport substance are the groups with 1-2 carbon atoms.

The position at which each styryl group has been substituted with the alkoxy group constituted from $R^9$ or $R^{10}$ can be usually any of the o-, m-, and p-positions with respect to the styryl group. However, from the standpoint of ease of production, the position thereof is preferably an o-position of the p-position. It is more preferred, from the standpoint of the properties of the electrophotographic photoreceptor, that both $R^9$ and $R^{10}$ should be at the p-positions or at o-positions or that $R^9$ should be at the p-position and $R^{10}$ be at an o-position.

In formula (2), $R^{11}$ to $R^{13}$ each independently represent a hydrogen atom, an alkyl group, an aryl group, or an alkoxy group. Specifically, examples of the alkyl group include linear alkyl groups such as methyl, ethyl, n-propyl, and n-butyl, branched alkyl groups such as isopropyl and ethylhexyl, and cycloalkyl groups such as cyclohexyl. Examples of the aryl group include phenyl and naphthyl groups which may have a substituent. Examples of the alkoxy group include linear alkoxy groups such as methoxy, ethoxy, n-propoxy, and n-butoxy, branched alkoxy groups such as isopropoxy and ethylhexyloxy, and cyclohexyloxy. Preferred of these are hydrogen atom, alkyl groups having 1-8 carbon atoms, and alkoxy groups having 1-8 carbon atoms, from the standpoint of the suitability of starting materials for general-purpose use. More preferred from the standpoint of handleability during production are hydrogen atom, alkyl groups having 1-6 carbon atoms, and alkoxy groups having 1-6 carbon atoms. Even more preferred from the standpoint of the photo-decay characteristics of the electrophotographic photoreceptor are hydrogen atom and the alkyl groups having 1-2 carbon atoms. Hydrogen atom is especially preferred from the standpoint of the charge-transporting ability of the charge transport substance.

In formula (2), $R^{14}$ and $R^{15}$ each independently represent any of a hydrogen atom, an alkyl group, an aryl group, and an alkoxy group. Specifically, examples of the alkyl group include linear alkyl groups such as methyl, ethyl, n-propyl, and n-butyl, branched alkyl groups such as isopropyl and ethylhexyl, and cycloalkyl groups such as cyclohexyl. Examples of the aryl group include phenyl and naphthyl groups which may have a substituent. Examples of the alkoxy group include linear alkoxy groups such as methoxy, ethoxy, n-propoxy, and n-butoxy, branched alkyl groups such as isopropoxy and ethylhexyloxy, and cyclohexyloxy. Preferred of these are hydrogen atom, alkyl groups having 1-8 carbon atoms, and alkoxy groups having 1-8 carbon atoms, from the standpoint of the suitability of starting materials for general-purpose use. More preferred from the standpoint of handleability during production are hydrogen atom, alkyl groups having 1-6 carbon atoms, and alkoxy groups having 1-6 carbon atoms. Even more preferred from the standpoint of the photo-decay characteristics of the electrophotographic photoreceptor are alkyl groups having 1-4 carbon atoms and alkoxy groups having 1-4 carbon atoms. Especially preferred from the standpoint of the ozone resistance of the electrophotographic photoreceptor are alkyl groups having 1-4 carbon atoms. Most preferred from the standpoint of the charge-transporting ability of the charge transport substance are the alkyl groups having 1-2 carbon atoms.

In formula (2), l and m each independently represent an integer of 1-5. In the case where l and m each represent an integer of 2 or larger, the multiple $R^{14}$ moieties bonded to the benzene ring may be different from each other, and the multiple $R^{15}$ moieties bonded to the benzene ring also may be different from each other.

The positions at which the arylamine groups have been substituted with $R^{14}$ and $R^{15}$ can be usually any of the o-, m-, and p-positions. However, from the standpoint of ease of production, the positions thereof are preferably o-positions or the p-positions. More preferred, from the standpoint of the photo-decay characteristics of the electrophotographic photoreceptor, are the p-positions. In the case where there are a plurality of $R^{14}$ substituents or $R^{15}$ substituents, the bonding sites thereof are usually not limited unless the effects of the invention are considerably lessened. However, it is preferred, from the standpoint of the solubility of the charge transport substance, that the substituents should have been bonded at any of the p- and o-positions.

In formula (2), $R^{16}$ and $R^{17}$ each independently represent a hydrogen atom, an alkyl group, an aryl group, or an alkoxy group. Specifically, examples of the alkyl group include linear alkyl groups such as methyl, ethyl, n-propyl, and n-butyl, branched alkyl groups such as isopropyl and ethylhexyl, and cycloalkyl groups such as cyclohexyl. Examples of the aryl group include phenyl and naphthyl groups which may have a substituent. Examples of the alkoxy group include linear alkoxy groups such as methoxy, ethoxy, n-propoxy, and n-butoxy, branched alkoxy groups such as isopropoxy and ethylhexyloxy, and cyclohexyloxy. Preferred of these are hydrogen atom, alkyl groups having 1-8 carbon atoms, and alkoxy groups having 1-8 carbon atoms, from the standpoint of the suitability of starting materials for general-purpose use. More preferred from the standpoint of the ozone resistance of the electrophotographic photoreceptor are hydrogen atom and alkyl groups having 1-4 carbon atoms. Even more preferred from the standpoint of the charge-transporting ability of the charge transport substance is hydrogen atom.

In formula (2), $n_2$ represents an integer of 1-5. From the standpoint of improving the solubility in coating-fluid solvents, $n_2$ is preferably 4 or less. From the standpoint of the charge-transporting ability of the charge transport substance, $n_2$ is more preferably 3 or less. From the standpoint of the photo-decay characteristics of the electrophotographic photoreceptor, $n_2$ is even more preferably 2 or less. Meanwhile, from the standpoint of inhibiting the electrophotographic photoreceptor from decreasing in charging property, $n_2$ is preferably 2 or larger.

In formula (2), the arylene moiety to which the diphenylamino groups have been bonded represents a phenylene group when $n_2=1$, a biphenylene group when $n_2=2$, a terphenylene group when $n_2=3$, a quaterphenylene group when $n_2=4$, and a quinquephenylene group when $n_2=5$. The positions at which the two diphenylamino groups have been bonded to the arylene group are not limited unless the effects of the invention are considerably lessened. However, when $n_2=1$, it is preferred, from the standpoint of the charging properties of the electrophotographic photoreceptor, that the two diphenylamino groups should be bonded to the phenylene group at meta positions to each other. When $n_2=2$, it is preferred, from the standpoint of the charge-transporting ability of the charge transport substance, that the two diphenylamino groups should be bonded at the 4- and 4'-positions of the biphenylene group. When $n_2=3$, the terphenylene group is preferably a p-terphenylene group from the standpoint of the suitability of starting materials for general-purpose use, and it is preferred, from the standpoint of the charge-transporting ability of the charge transport substance, that the diphenylamine groups should be bonded to the p-terphenylene group at the 4- and 4"-positions. When $n_2=4$, the quaterphenylene group is preferably a p-quaterphenylene group from the standpoint of the suitability of starting materials for general-purpose use, and it is preferred, from the standpoint of the charge-transporting ability of the charge transport substance, that the diphenylamine groups should be bonded to the p-quaterphenylene group at the 4- and 4'''-positions. When $n_2=5$, the quinquephenylene group is preferably a p-quinquephenylene group from the standpoint of the suitability of starting materials for general-purpose use, and it is preferred, from the standpoint of the charge-transporting ability of the charge transport substance, that the diphenylamine groups should be bonded to the p-quinquephenylene group at the 4- and 4''''-positions.

In the case where one or more charge transport substances according to the second aspect of the invention are used to obtain an electrophotographic photoreceptor in the invention, the photosensitive layer of this electrophotographic photoreceptor may be a photosensitive layer which contains a compound represented by formula (2) as the only component represented by the formula, or may contain a mixture of compounds of different structures represented by formula (2). From the standpoint of productivity including the property of forming the photosensitive layer, it is preferred to use a mixture including positional isomers of a compound represented by formula (2). In the invention, in the case where a mixture of positional isomers is used, it is more preferred from the standpoint of the properties of the electrophotographic photoreceptor that the mixture should be a mixture of positional isomers which differ in the positions of substitution with the alkoxy groups constituted from $R^9$ and $R^{10}$. This mixture of positional isomers in terms of the positions of the alkoxy groups usually includes two or more positional isomers, and the positional isomers included therein may be isomers in which the positions of substitution with the alkoxy groups constituted from $R^9$ and $R^{10}$ are any of the o-, m-, and p-positions with respect to the styryl groups. Preferred of such isomer mixtures, from the standpoint of procurement of starting materials, is a positional-isomer mixture in which at least one of the positional isomers has the alkoxy group constituted from $R^9$ or $R^{10}$ at any of the o- and p-positions with respect to the styryl group. From the standpoint of production of the charge transport substance, it is preferred that the positional-isomer mixture should be a mixture of any two or more positional isomers selected from an $o(R^9)$-$o(R^{10})$ isomer, an $o(R^9)$-$p(R^{10})$ isomer, and a $p(R^9)$-$p(R^{10})$ isomer. From the standpoint of the charge-transporting ability of the charge transport substance, it is more preferred that the mixture should be a mixture of positional isomers which at least include a $p(R^9)$-$p(R^{10})$ isomer, and it is even more preferred that the mixture should be a mixture composed of three positional isomers which are an $o(R^9)$-$o(R^{10})$ isomer, an $o(R^9)$-$p(R^{10})$ isomer, and a $p(R^9)$-$p(R^{10})$ isomer.

In the case where the mixture of positional isomers differing in the positions of substitution with the alkoxy groups constituted from $R^9$ and $R^{10}$ is used, the mixing ratio of the positional isomers is not particularly limited. However, from the standpoint of the photo-decay characteristics of the electrophotographic photoreceptor, it is preferred that the positional isomers should be mixed in such a ratio that the $p(R^9)$-$p(R^{10})$ isomer is contained in a highest proportion in the positional-isomer mixture. Specifically, the lower limit of the proportion of the $p(R^9)$-$p(R^{10})$ isomer is usually 35% or higher, preferably 40% or higher, while the upper limit thereof is usually 75% or less, preferably 60% or less, from the standpoint of the solubility of the charge transport substance.

Examples of the structures of charge transport substances suitable for the second aspect of the invention are shown below. The following structures are examples for a more detailed understanding of the invention, and the structure of the charge transport substance should not be construed as being limited to the following structures unless these structures depart from the spirit of the invention.

[Chem. 14]

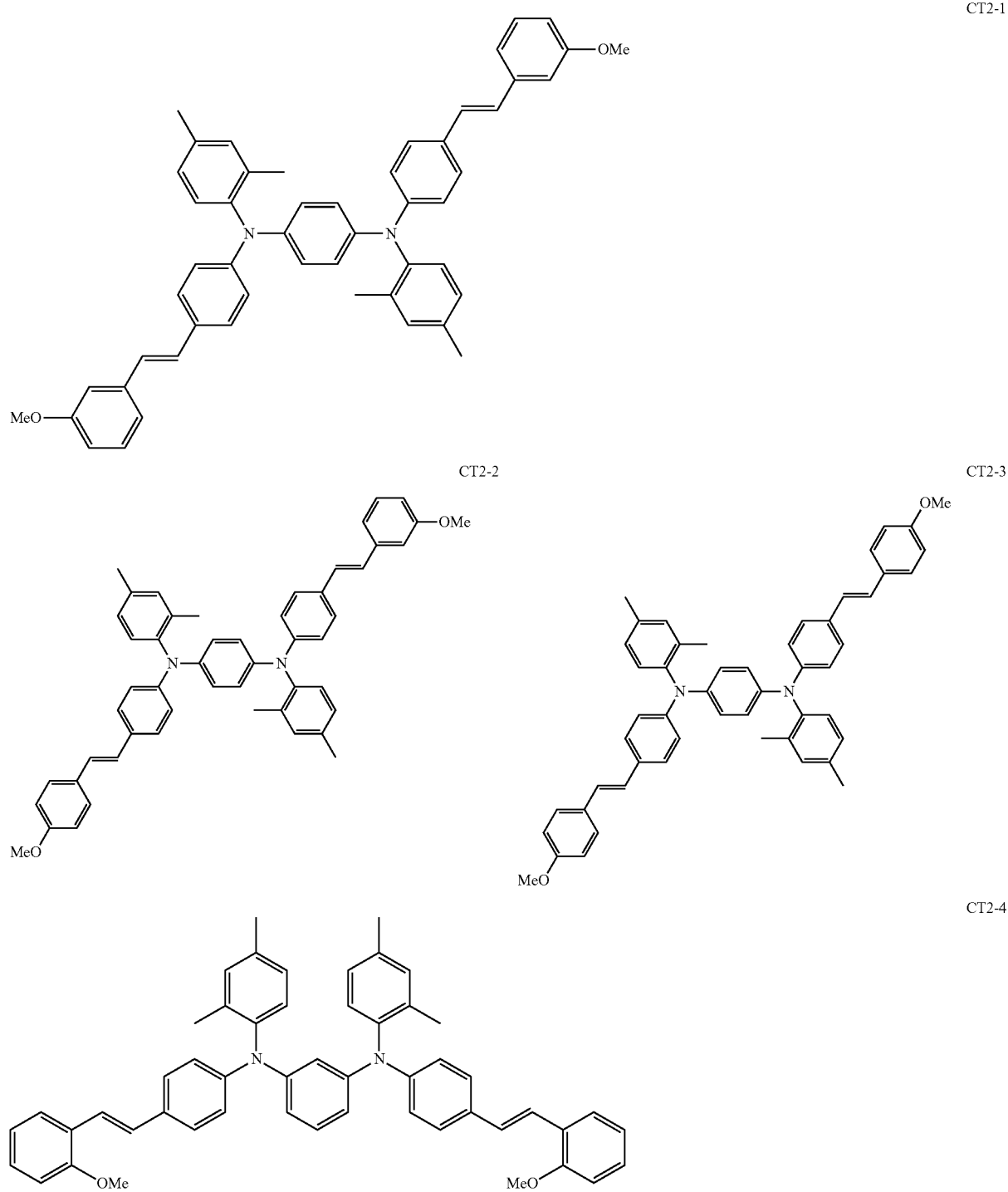

CT2-5
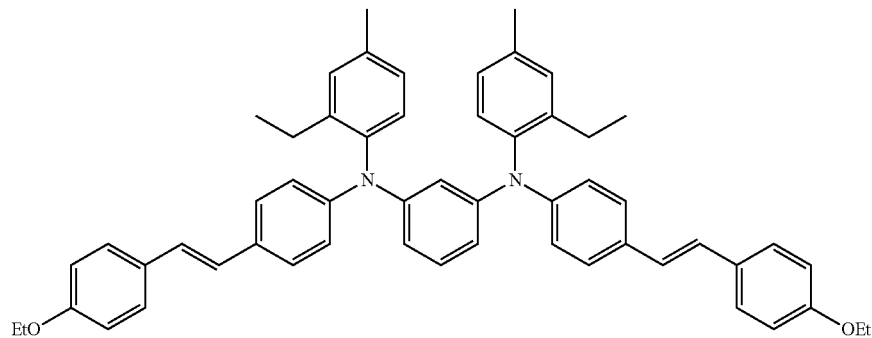
CT2-6
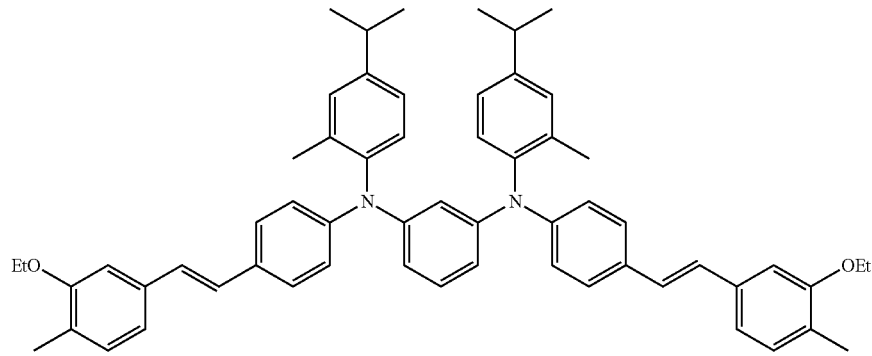
CT2-7
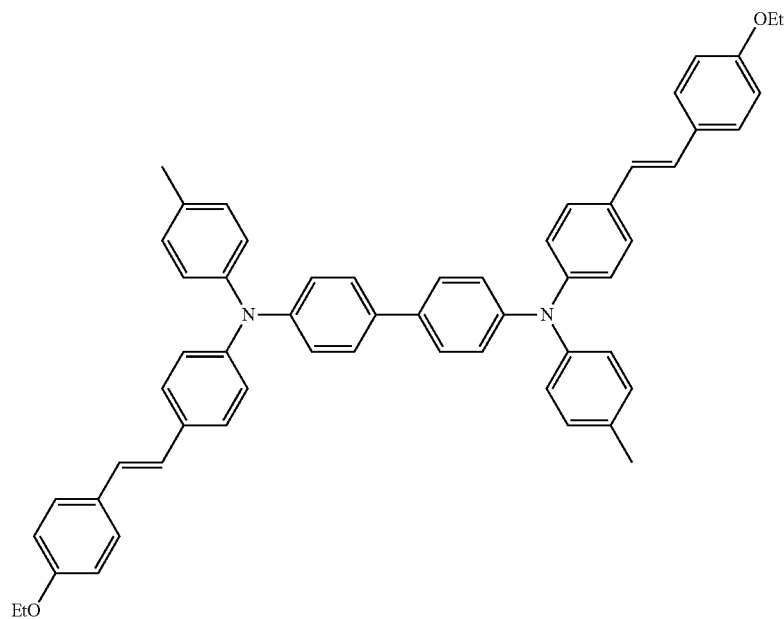

-continued
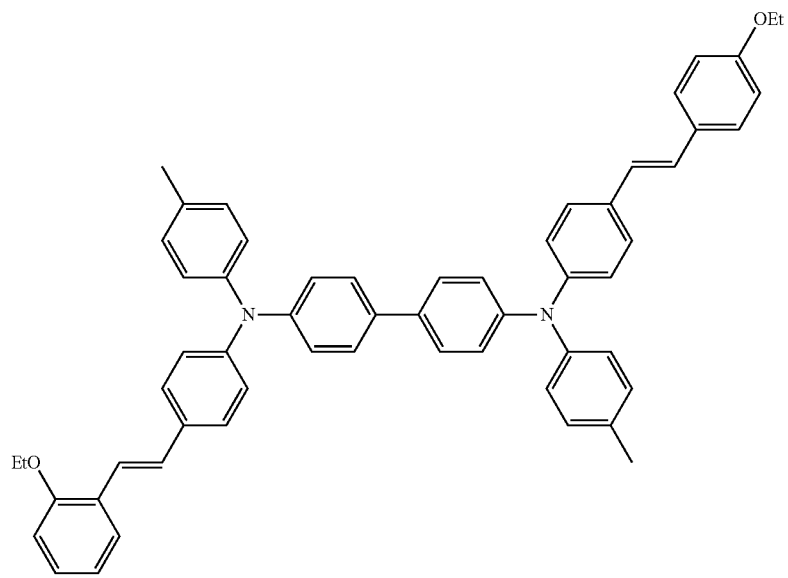
CT2-8
[Chem. 15]
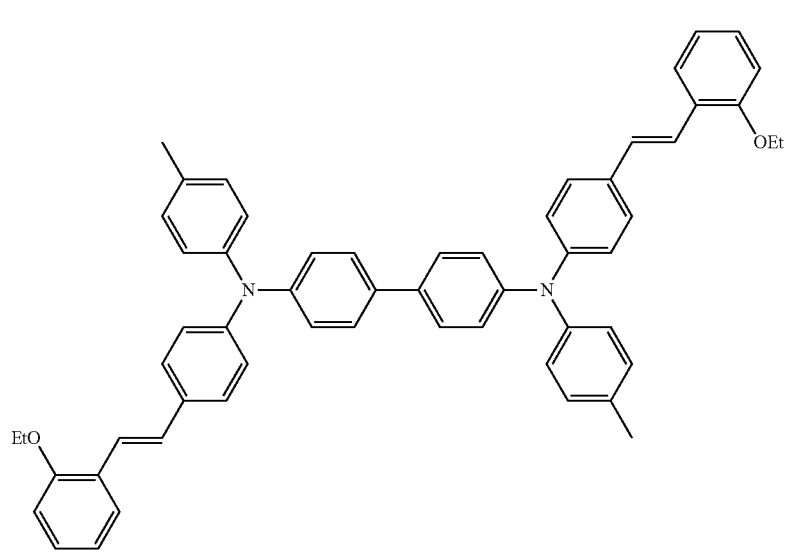
CT2-9

-continued
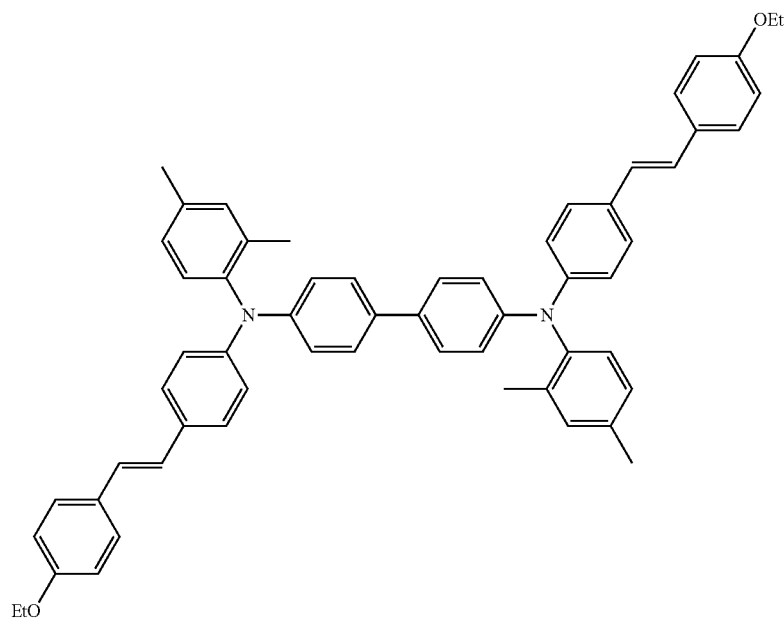
CT2-10
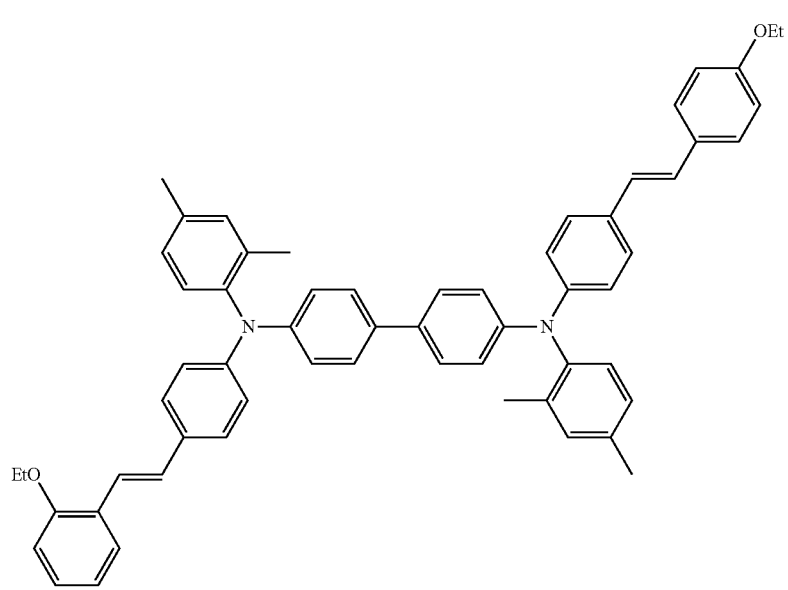
CT2-11

-continued
CT2-12
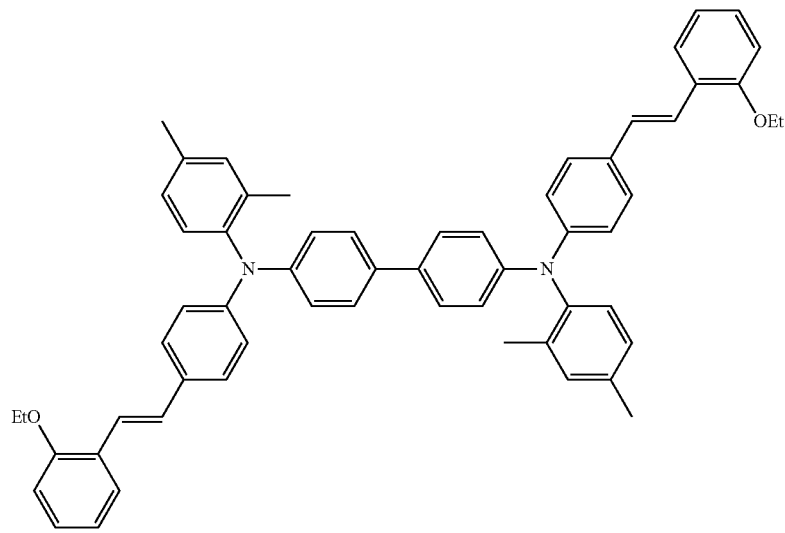
CT2-13
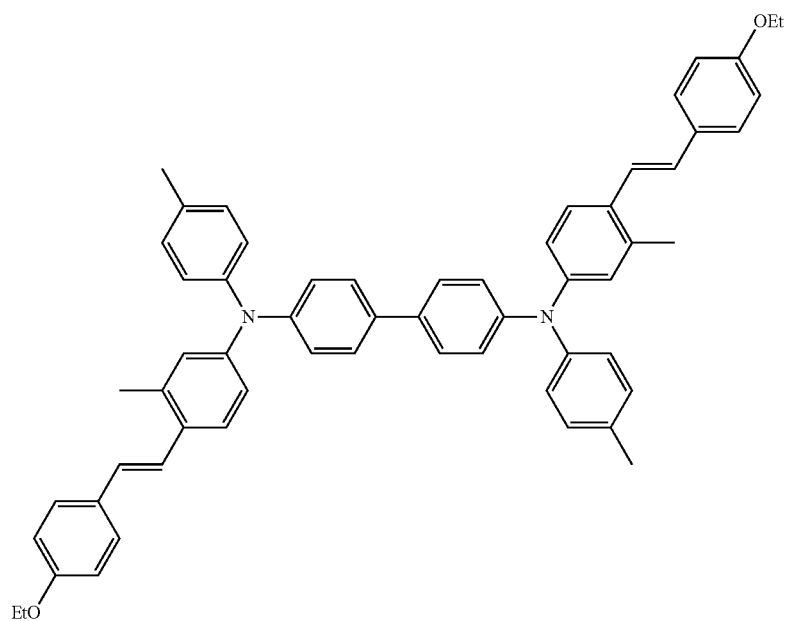

-continued
CT2-14
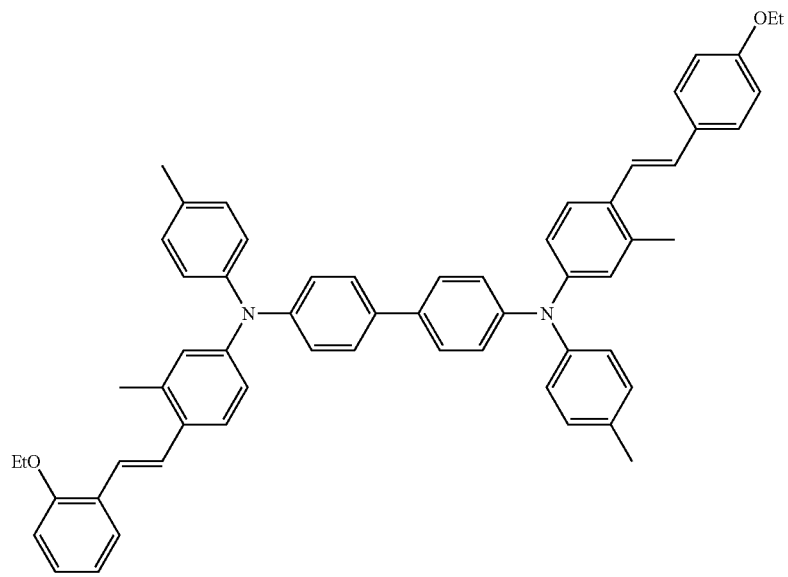
CT2-15
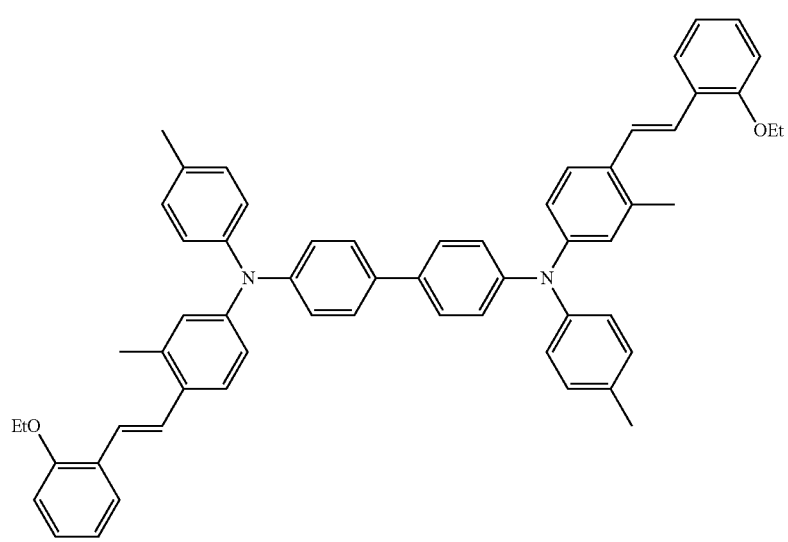

CT2-16
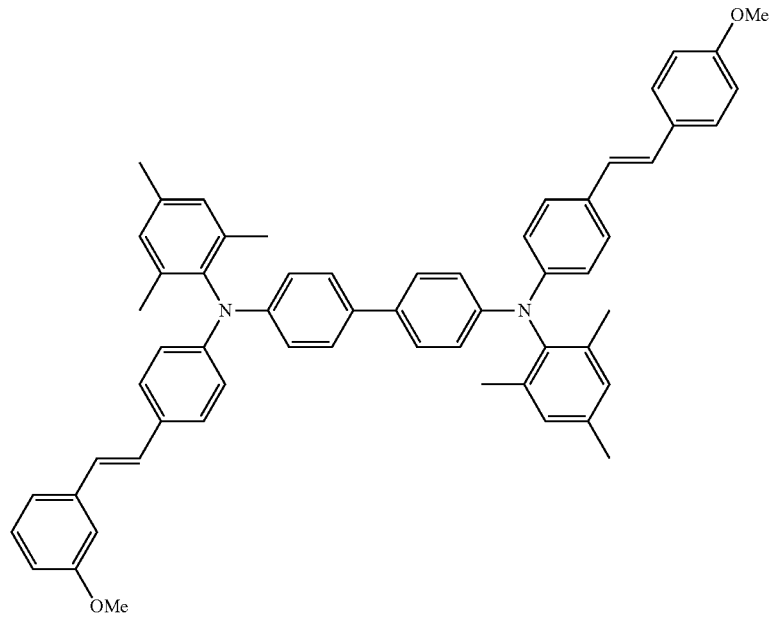
[Chem. 16]
CT2-17
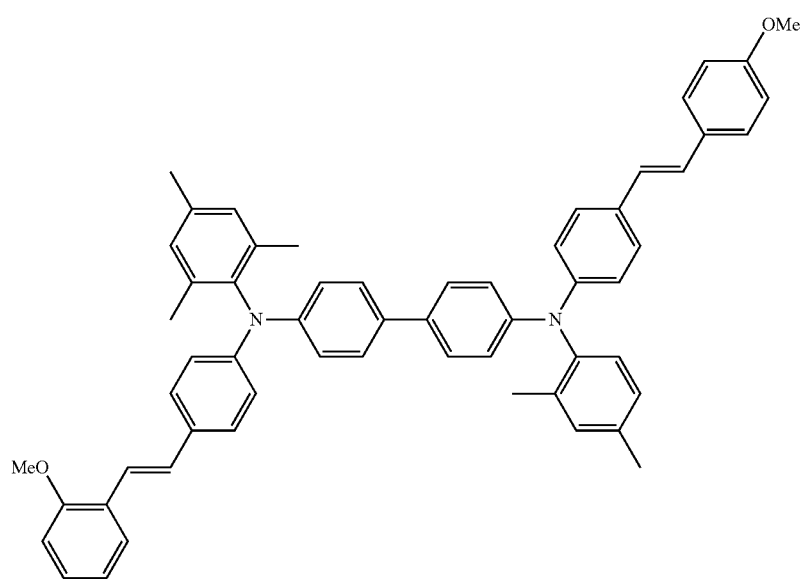

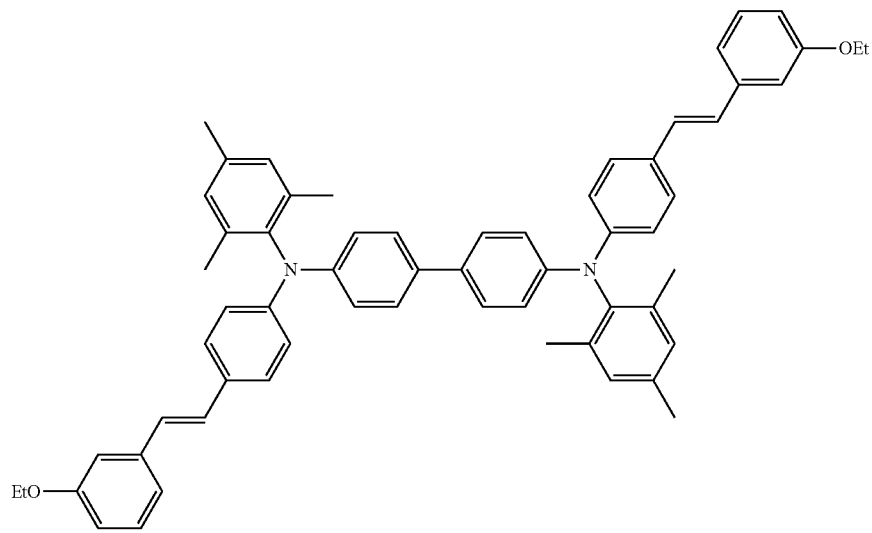
CT2-18
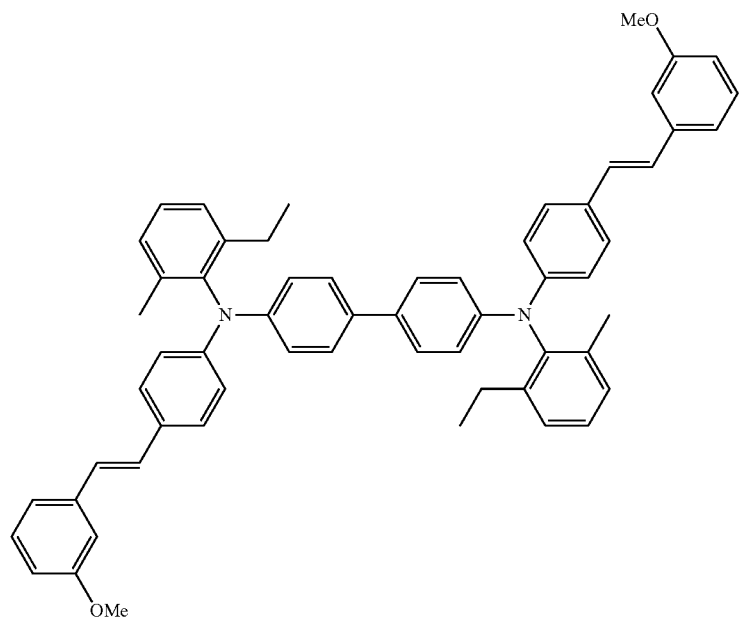
CT2-19

CT2-20
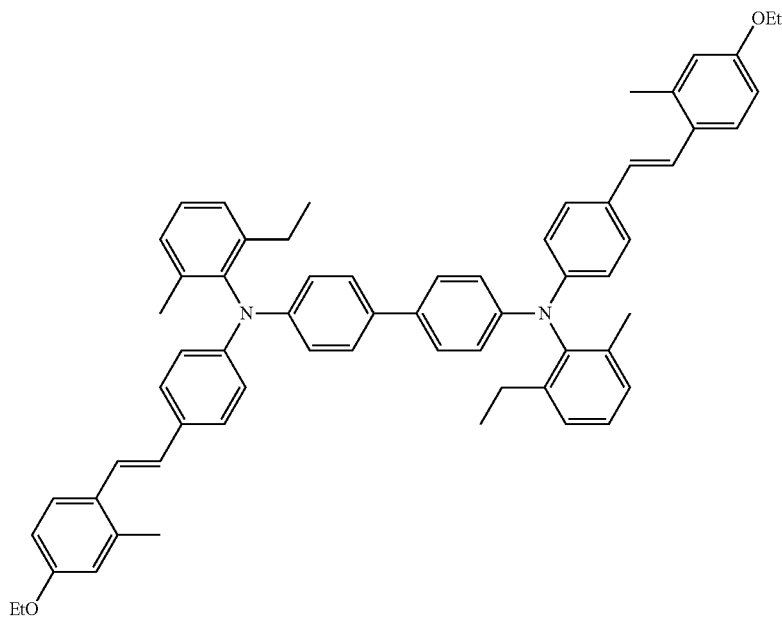
CT2-21
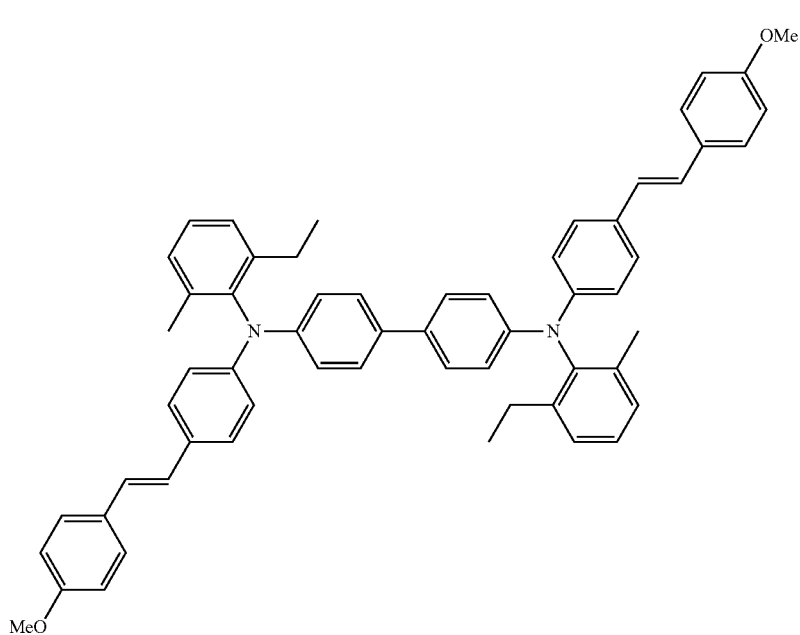

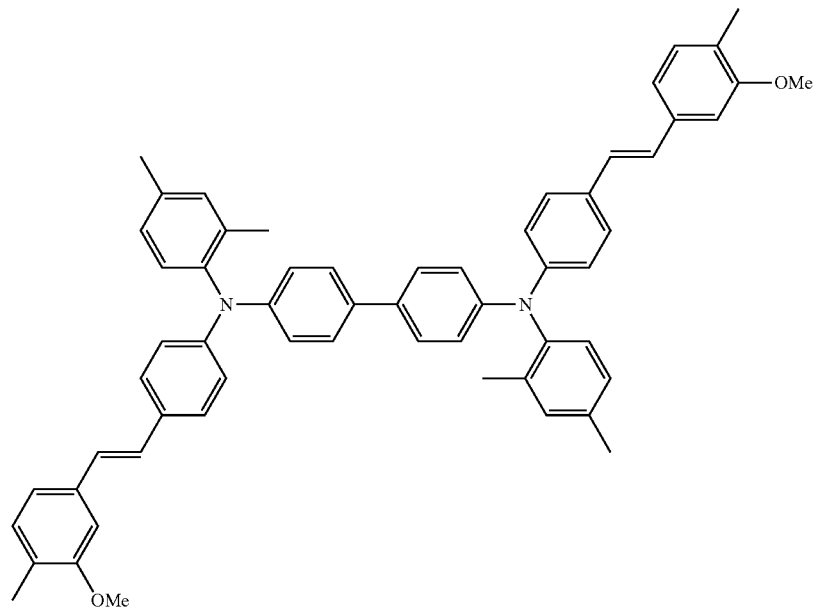
CT2-22
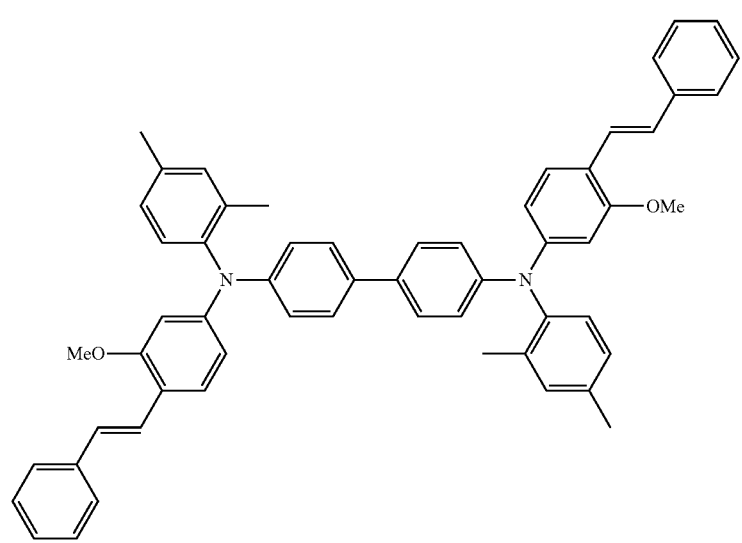
CT2-23

-continued
CT2-24
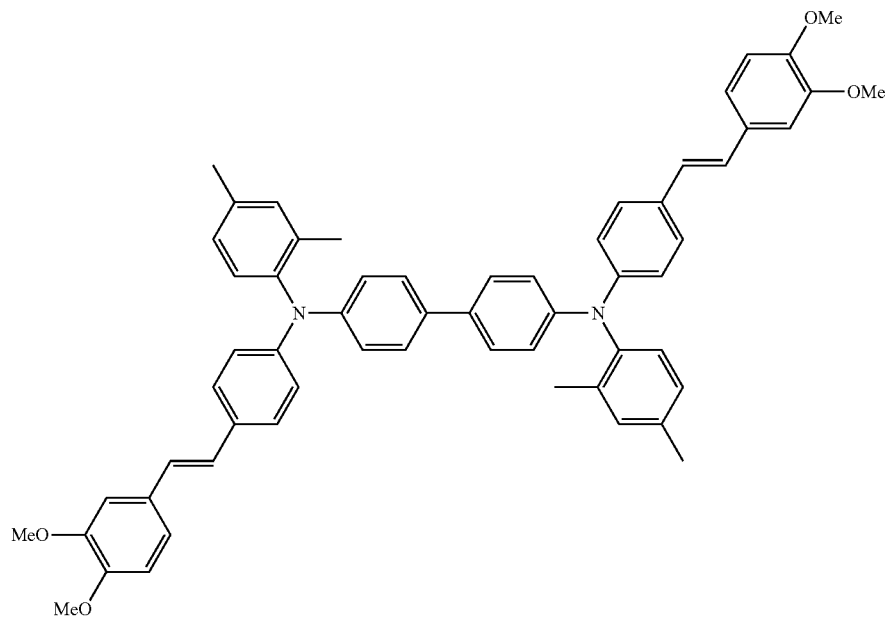
[Chem. 17]
CT2-25
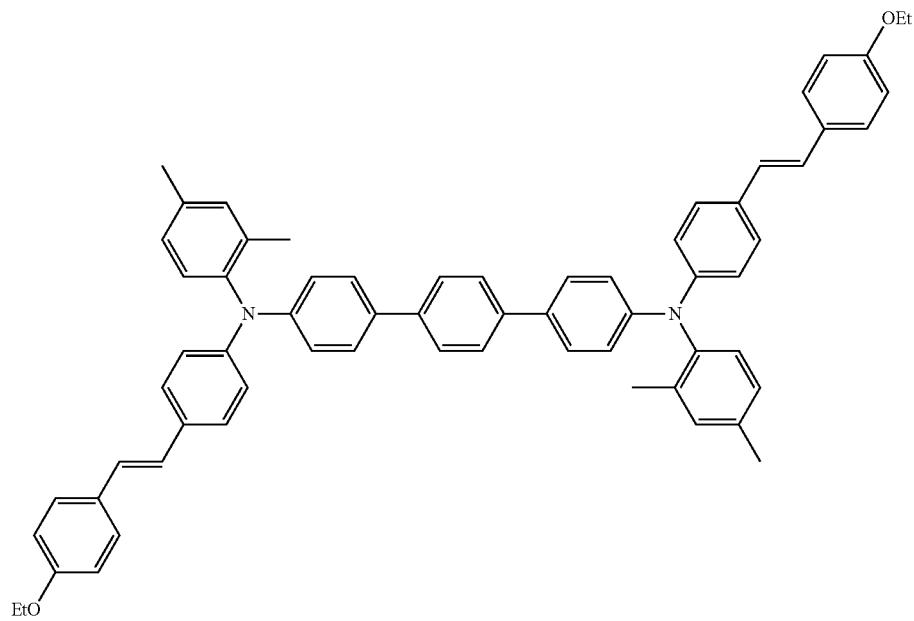

CT2-26
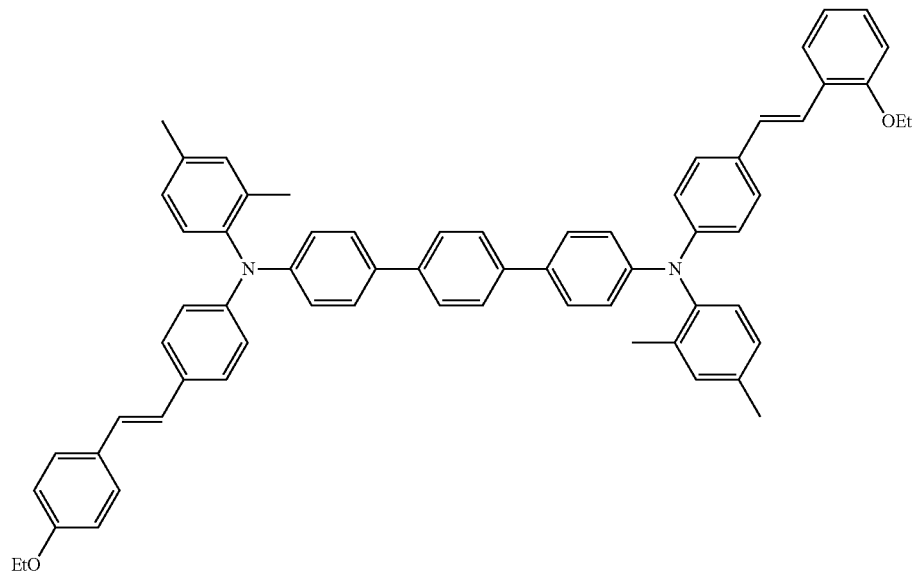
CT2-27
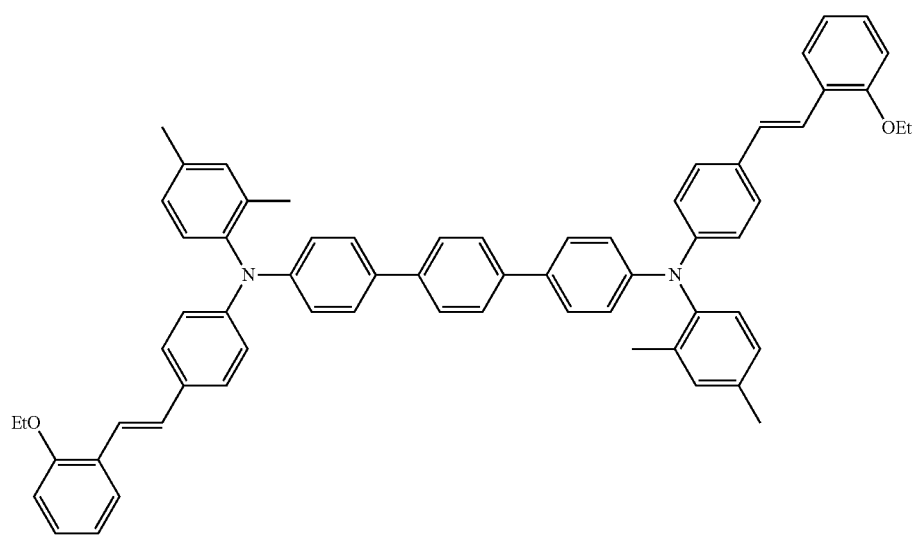

CT2-28
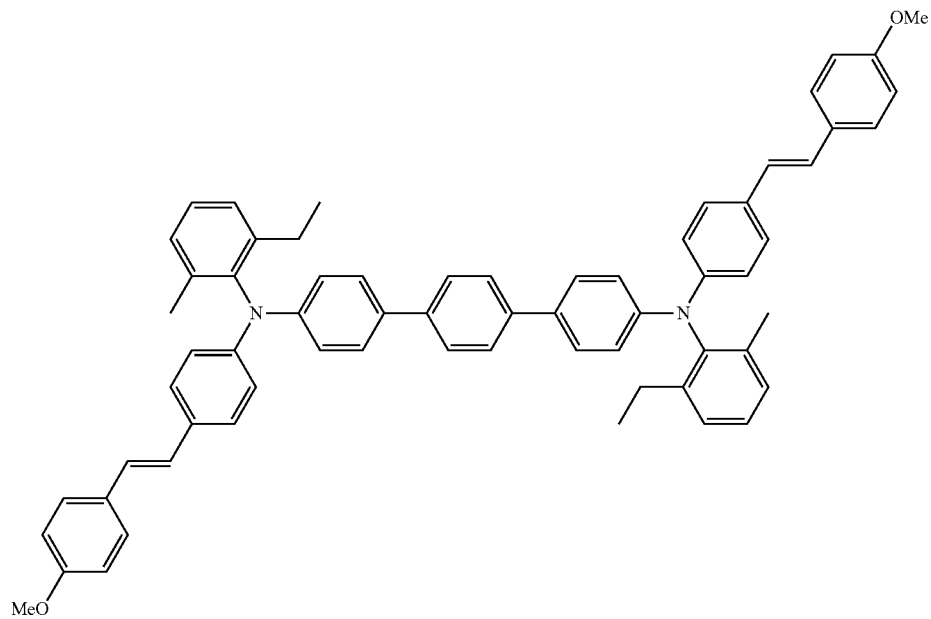
CT2-29
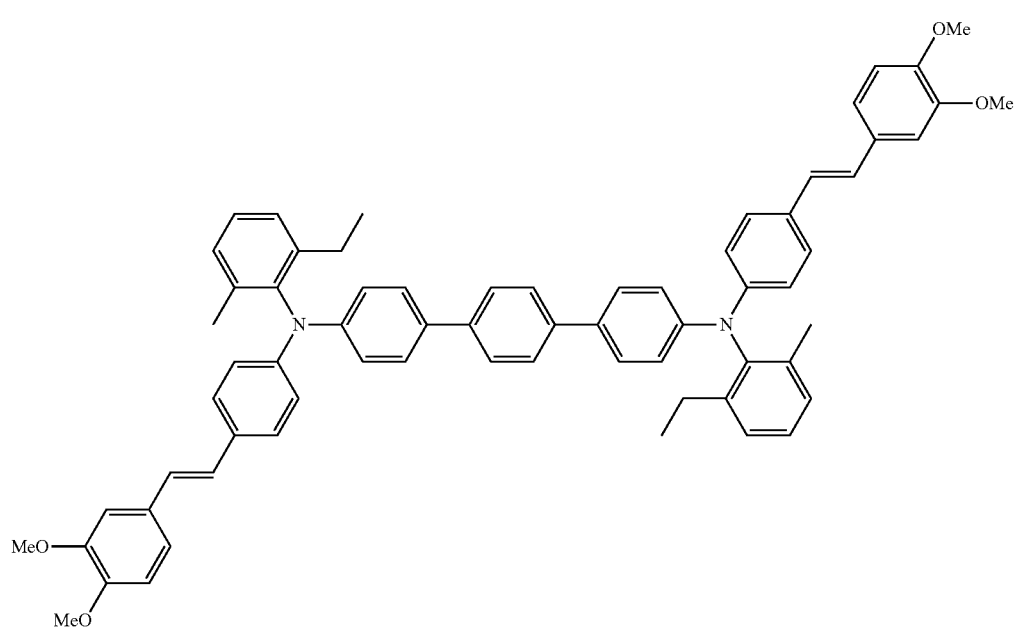

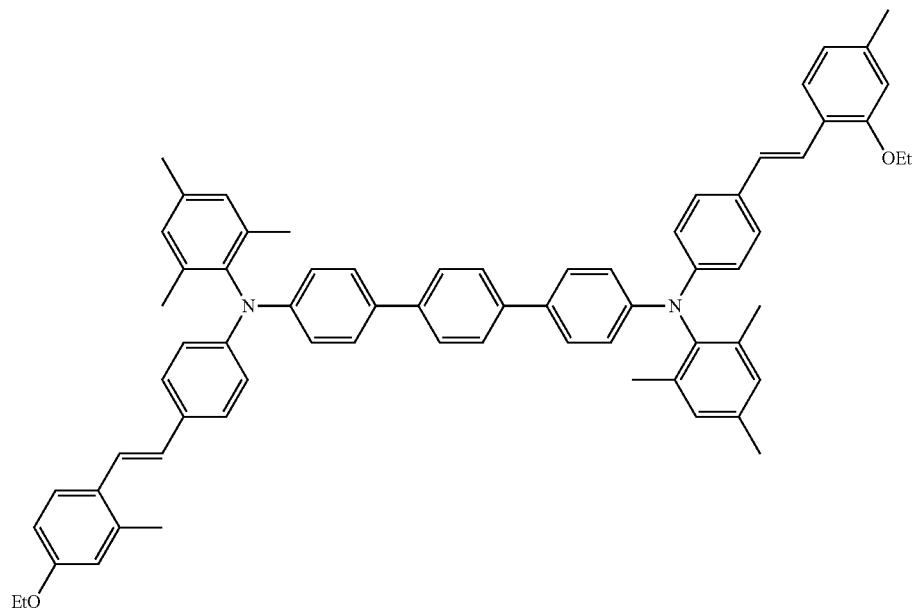
CT2-30
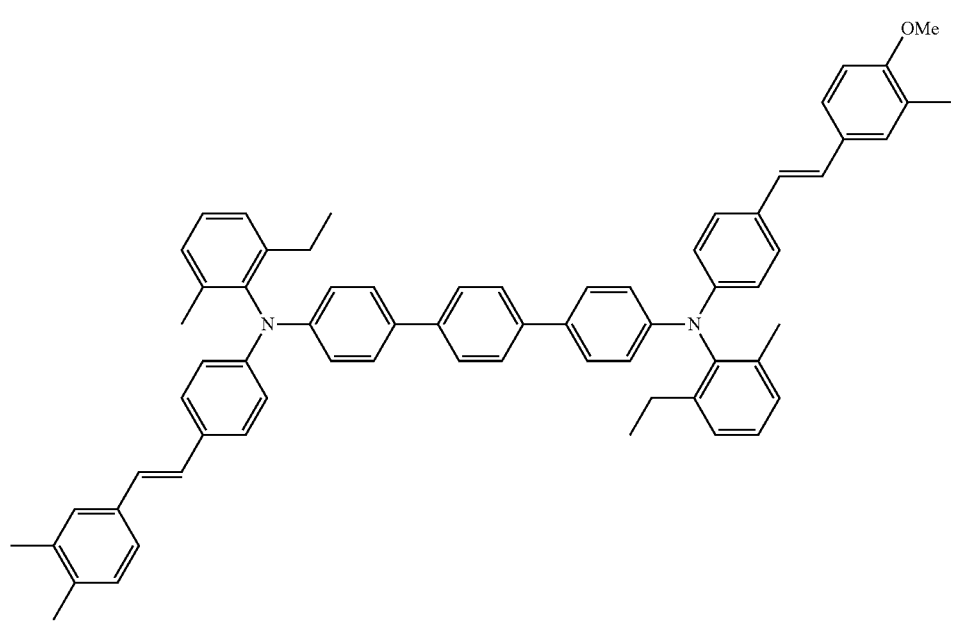
CT2-31

CT2-32
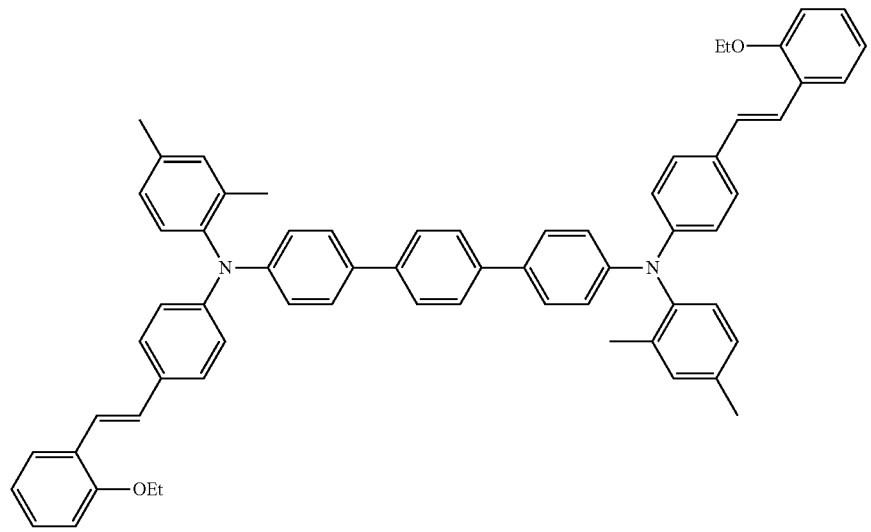
[Chem. 18]
CT2-33
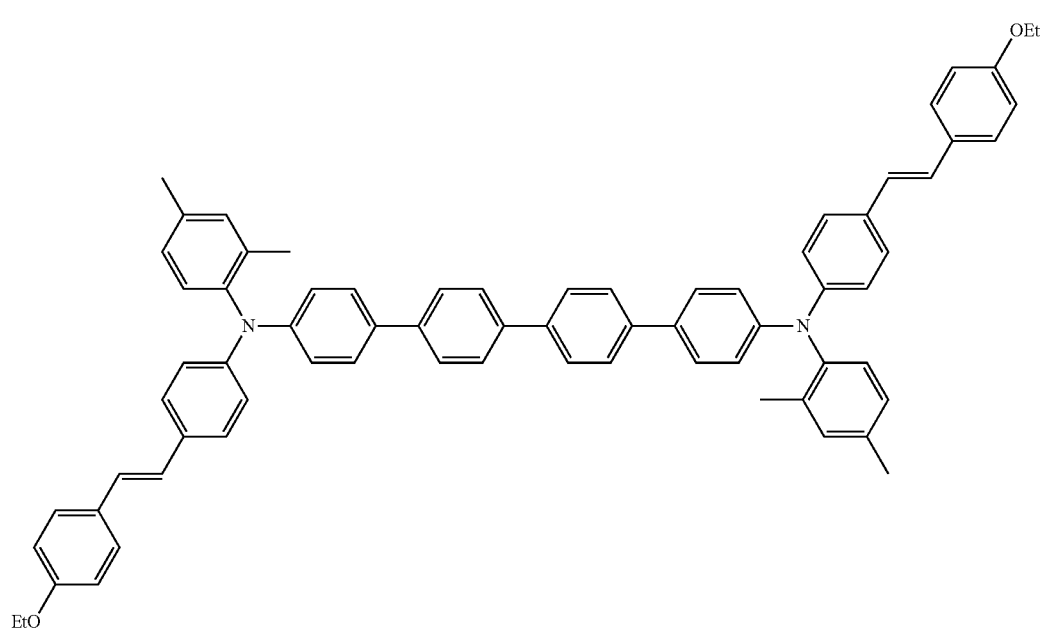

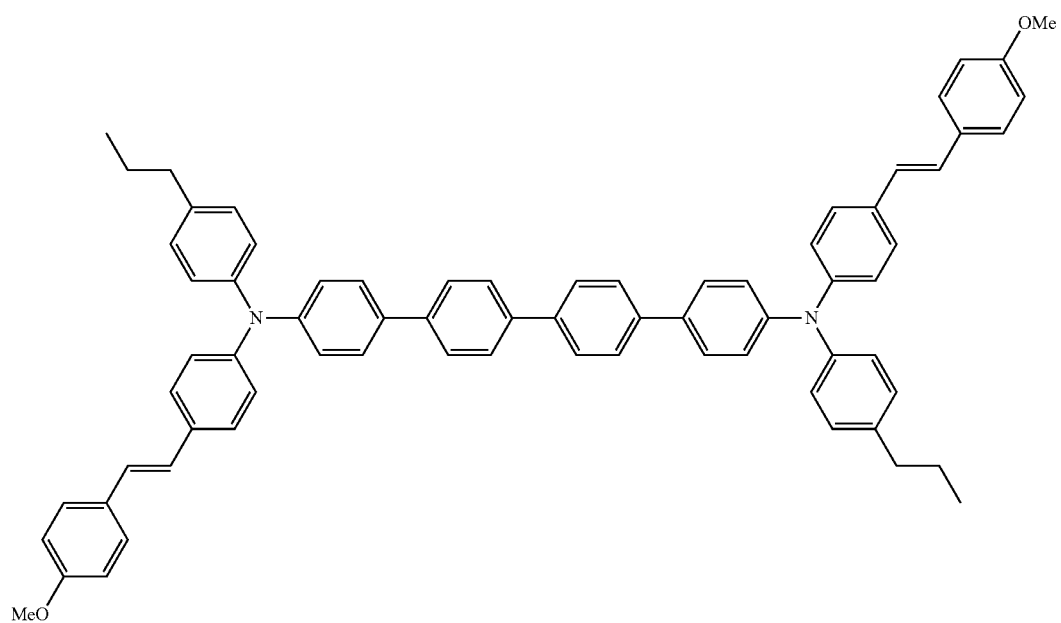
CT2-34
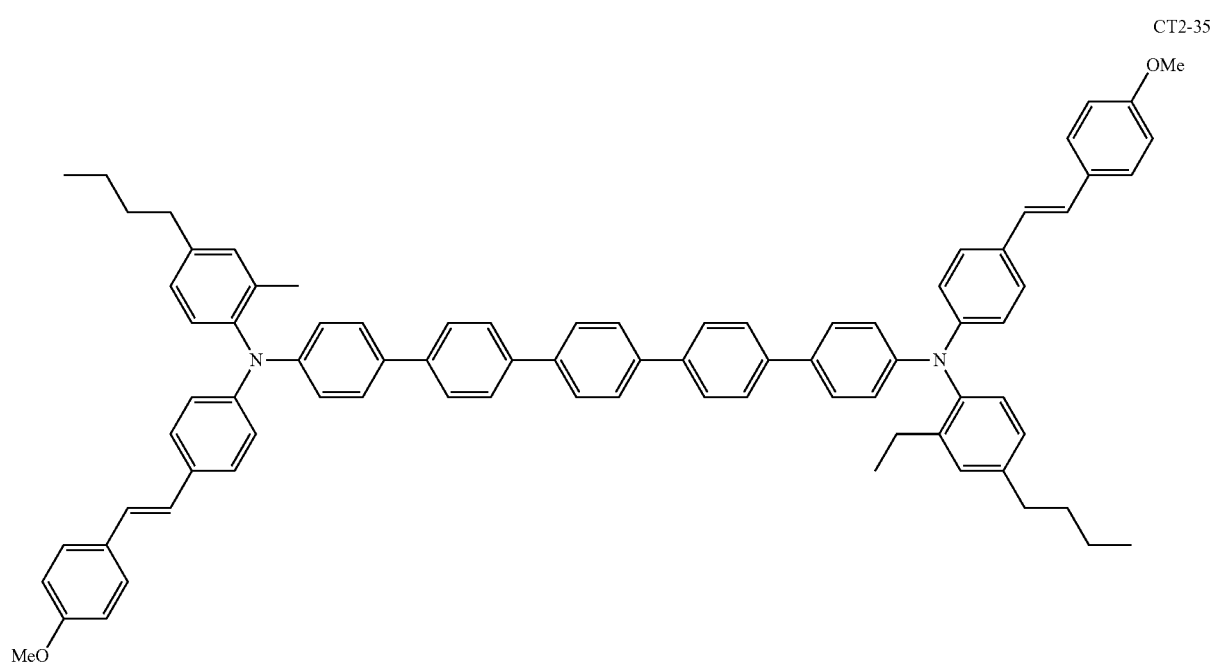
CT2-35

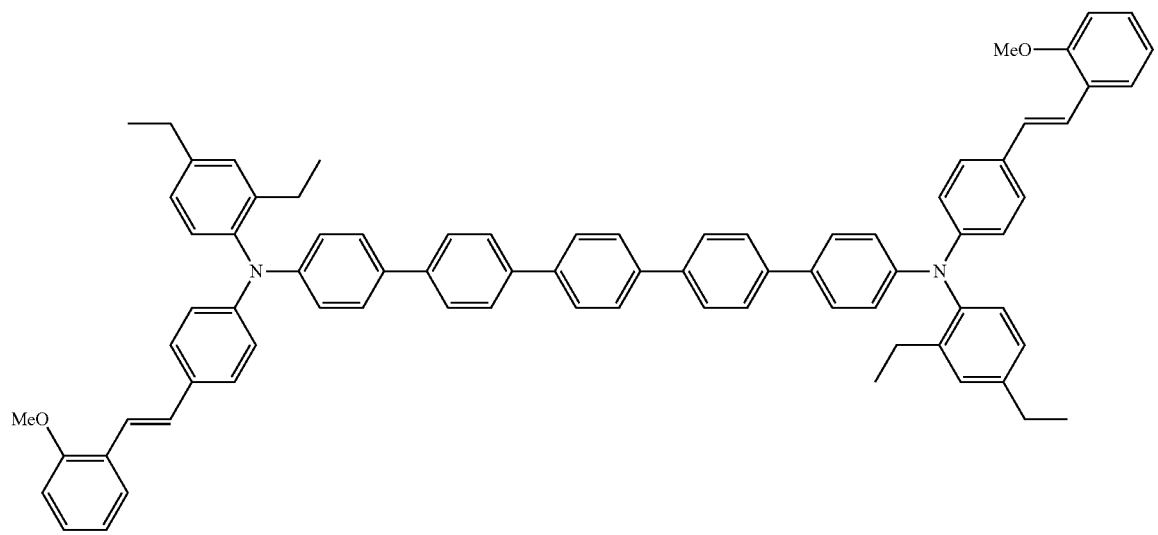

CT2-36

<Process for Producing Charge Transport Substance According to Second Aspect>

The charge transport substances CT2-1 to CT2-36 shown above as examples can be easily synthesized by known methods. For example, a positional-isomer mixture composed of the example compounds CT2-10 to CT2-12 can be produced in accordance with the scheme shown below.

For example, the mixture can be produced by formylating a compound having a tetraphenylbenzidine framework by, for example, the Vilsmeier reaction and then reacting the formylated compound with phosphoric ester compounds to introduce styryl groups thereinto (scheme 3).

(Scheme 3)

[Chem. 19]

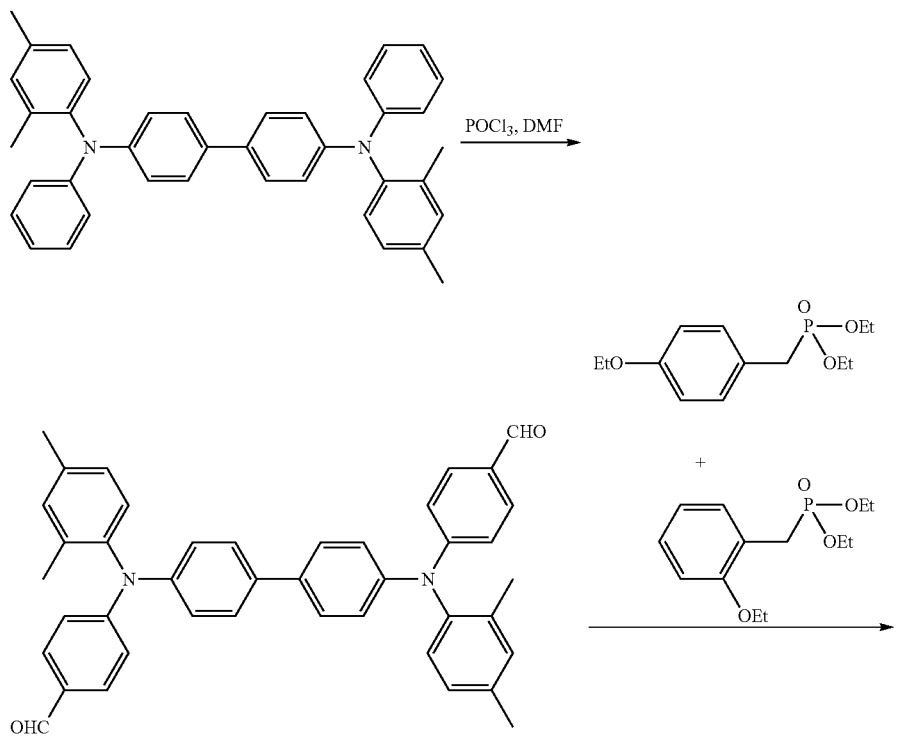

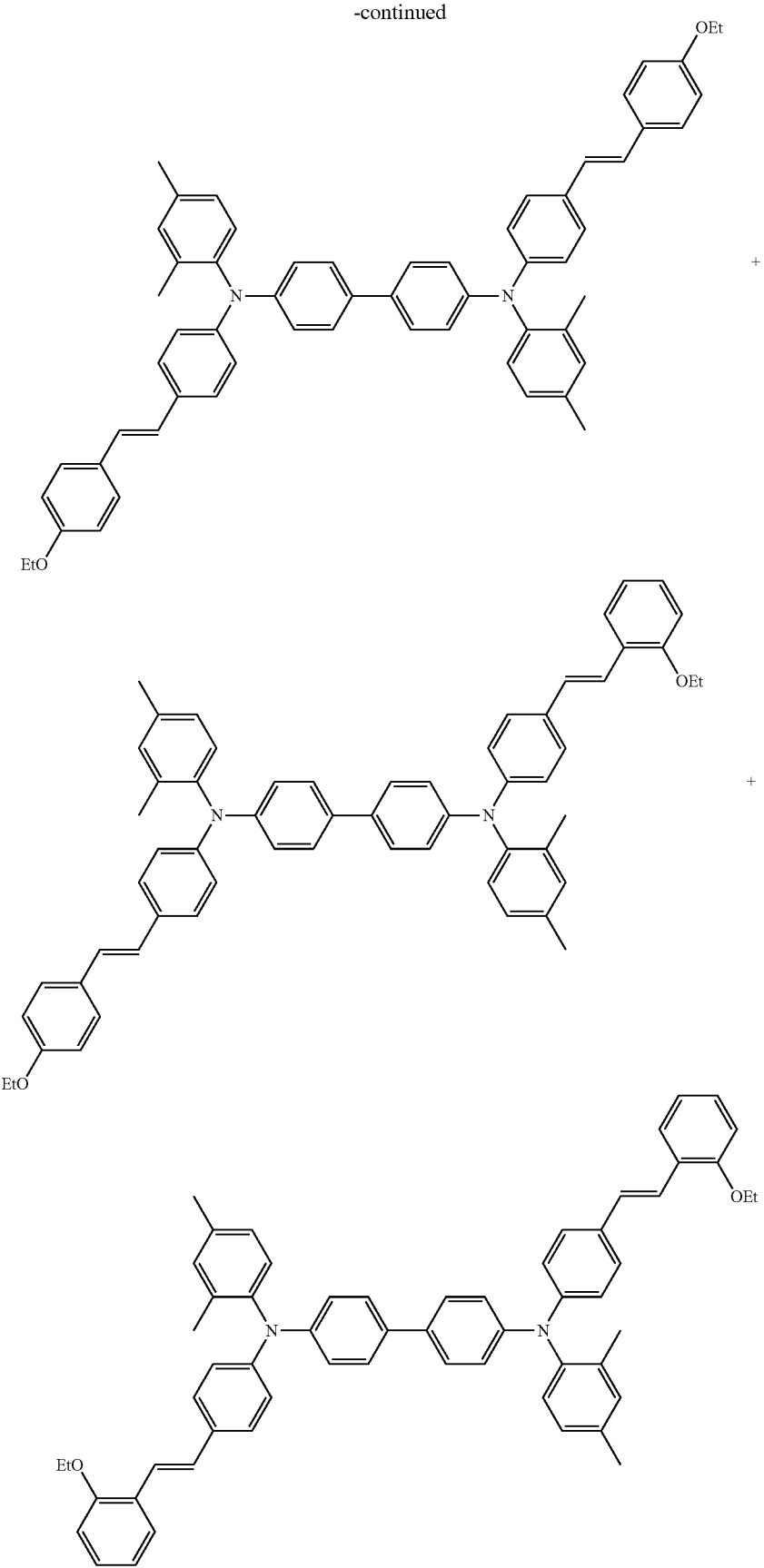

<<Electrophotographic Photoreceptor>>

The configuration of the electrophotographic photoreceptor of the invention is explained below.

The electrophotographic photoreceptor of the invention is not particularly limited in the structure thereof so long as the photoreceptor includes a conductive support and, disposed thereover, a photosensitive layer that contains either a charge transport substance according to the first aspect, which is represented by formula (1), or a charge transport substance according to the second aspect, which is represented by formula (2).

In the case where the photosensitive layer of the electrophotographic photoreceptor is of the multilayer type which will be explained later, this photosensitive layer includes a charge transport layer which contains a charge transport substance represented by formula (1) or formula (2) and a binder resin and which further contains an antioxidant, a leveling agent, and other additives according to need. In the case where the photosensitive layer of the electrophotographic photoreceptor is of the single-layer type which will be explained later, a charge generation material and an electron transport material are generally used in addition to the ingredients used in the above-described charge transport layer of the multilayer type photoreceptor.

<Conductive Support>

There are no particular limitations on the conductive support. For example, use may be mainly made of a metallic material such as aluminum, an aluminum alloy, stainless steel, copper, or nickel, a resinous material to which electrical conductivity has been imparted by adding thereto a conductive powder of a metal, carbon, tin oxide, or the like, or a resin, glass, paper, or the like having a surface on which a conductive material such as aluminum, nickel, or ITO (indium-tin oxide) has been deposited by vapor deposition or coating fluid application. One of these materials may be used alone, or any desired two or more thereof may be used in combination in any desired proportion. The shape of the conductive support may be a drum, sheet, or belt form or another form. Furthermore, use may be made of a conductive support which is made of a metallic material and which has been coated with a conductive material having an appropriate resistivity for the purpose of regulating conductivity, surface properties, etc. or of covering defects.

In the case where a metallic material such as an aluminum alloy is used as the conductive support, an anodized coating film may be formed thereon before the support is used. In the case where an anodized coating film has been formed, it is desirable to conduct a pore-filling treatment by a known method.

The surface of the conductive support may be smooth, or may have been roughened by using a special cutting technique or by conducting grinding. The conductive support may have a roughened surface obtained by incorporating particles having an appropriate particle diameter into the material constituting the support. From the standpoint of cost reduction, a drawn tube can be used as such without being subjected to cutting.

<Undercoat Layer>

An undercoat layer may be disposed between the conductive support and the photosensitive layer, which will be described later, in order to improve adhesion, nonblocking properties, etc. As the undercoat layer, use is made, for example, of a resin or a mixture of a resin and particles of a metal oxide or the like dispersed therein. The undercoat layer made be a layer constituted of a single layer, or may be a layer composed of a plurality of layers.

Examples of the metal oxide particles for use in the undercoat layer include particles of metal oxides containing one metallic element, such as titanium oxide, aluminum oxide, silicon oxide, zirconium oxide, zinc oxide, and iron oxide, and particles of metal oxides containing a plurality of metallic elements, such as calcium titanate, strontium titanate, and barium titanate. Metal oxide particles of one kind among these may be used alone, or a mixture of multiple kinds of metal oxide particles may be used. Preferred of these particulate metal oxides are titanium oxide and aluminum oxide. Especially preferred is titanium oxide. The surface of the titanium oxide particles may have undergone a treatment with an inorganic substance such as tin oxide, aluminum oxide, antimony oxide, zirconium oxide, or silicon oxide or with an organic substance such as stearic acid, a polyol, or a silicone. With respect to the crystal form of the titanium oxide particles, any of rutile, anatase, brookite, and amorphous ones can be used. Furthermore, the particles may include ones having a plurality of crystal states.

With respect to the particle diameter of the metal oxide particles, particles having various particle diameters can be utilized. Especially from the standpoints of properties and the stability of the fluid, the average primary particle diameter thereof is preferably 10-100 nm, especially preferably 10-50 nm. This average particle diameter can be obtained, for example, from a TEM photograph.

It is desirable that the undercoat layer should be formed as a layer in which particles of a metal oxide have been dispersed in a binder resin. Examples of binder resins usable for the undercoat layer include known binder resins such as epoxy resins, polyethylene resins, polypropylene resins, acrylic resins, methacrylic resins, polyamide resins, vinyl chloride resins, vinyl acetate resins, phenolic resins, polycarbonate resins, polyurethane resins, polyimide resins, vinylidene chloride resins, poly(vinyl acetal) resins, vinyl chloride/vinyl acetate copolymers, poly(vinyl alcohol) resins, polyurethane resins, polyacrylic resins, polyacrylamide resins, polyvinylpyrrolidone resins, polyvinylpyridine resins, water-soluble polyester resins, cellulose ester resins including nitrocellulose, cellulose ether resins, casein, gelatin, poly(glutamic acid), starch, starch acetate, aminostarch, organozirconium compounds including zirconium chelate compounds and zirconium alkoxide compounds, organic titanyl compounds including titanyl chelate compounds and titanium alkoxide compounds, and silane coupling agents. One of these binder resins may be used alone, or any desired two or more thereof may be used in combination in any desired proportion. A binder resin may be incorporated together with a hardener to use the resin in a cured state. Preferred of those binder resins are alcohol-soluble copolyamides, modified polyamides, and the like because these resins show satisfactory dispersibility and applicability.

The proportion of the metal oxide particles to be used, to the binder resin to be used for the undercoat layer, can be selected at will. However, from the standpoint of the stability and applicability of the dispersion, it is preferred to use the metal oxide particles in a proportion usually in the range of 10-500% by mass based on the binder resin.

The undercoat layer may have any desired thickness unless the effects of the invention are considerably lessened. However, from the standpoint of improving the electrical properties, suitability for intense exposure, image-forming properties, and repeatability of the electrophotographic photoreceptor and applicability during production, the thickness thereof is usually 0.01 µm or larger, preferably 0.1 µm or larger, and is usually 30 µm or less, preferably 20 µm or less.

A known antioxidant and the like may be incorporated into the undercoat layer. Pigment particles, resin particles, or the like may be used for the purpose of, for example, preventing image defects.

<Photosensitive Layer>

The photosensitive layer is formed over the conductive support described above (when the undercoat layer described above has been disposed, the photosensitive layer is formed on the undercoat layer). The photosensitive layer is a layer which contains a charge transport substance represented by the general formula (1) or general formula (2) described above. With respect to the type thereof, examples thereof include: a photosensitive layer of a single-layer structure in which a charge generation material and a charge transport material (including the charge transport substance of the invention) are present in the same layer and these materials have been dispersed in a binder resin (hereinafter suitably referred to as "single-layer type photosensitive layer"); and a photosensitive layer of the function allocation type having a multilayer structure composed of two or more layers including a charge generation layer in which a charge generation material has been dispersed in a binder resin and a charge transport layer in which a charge transport material (including the charge transport substance of the invention) has been dispersed in a binder resin (hereinafter suitably referred to as "multilayer type photosensitive layer"). The photosensitive layer may be either of these types.

Examples of the multilayer type photosensitive layer include a normal-superposition type photosensitive layer obtained by disposing a charge generation layer and a charge transport layer in this order from the conductive-support side and a reverse-superposition type photosensitive layer obtained by disposing the two layers in the reverse order, i.e., in the order of a charge transport layer and a charge generation layer from the conductive-support side. Although either of these photosensitive layers can be employed, the normal-superposition type photosensitive layer, which is capable of exhibiting most balanced photoconductivity, is preferred.

<Multilayer Type Photosensitive Layer>

[Charge Generation Layer]

The charge generation layer of the multilayer type photosensitive layer (function allocation type photosensitive layer) contains a charge generation material and usually further contains a binder resin and other ingredients which are used according to need. Such a charge generation layer can be obtained, for example, by dissolving or dispersing a charge generation material and a binder resin in a solvent or dispersion medium to produce a coating fluid, applying this coating fluid on a conductive support (or on an undercoat layer when the undercoat layer has been disposed) in the case of a normal-superposition type photosensitive layer or applying the coating fluid on a charge transport layer in the case of a reverse-superposition type photosensitive layer, and drying the coating fluid applied.

Examples of the charge generation substance include inorganic photoconductive materials such as selenium, alloys thereof, and cadmium sulfide and organic photoconductive materials such as organic pigments. However, organic photoconductive materials are preferred, and organic pigments are especially preferred of these. Examples of the organic pigments include phthalocyanine pigments, azo pigments, dithioketopyrrolopyrrole pigments, squalene (squarylium) pigments, quinacridone pigments, indigo pigments, perylene pigments, polycyclic quinone pigments, anthanthrone pigments, and benzimidazole pigments. Especially preferred of these are phthalocyanine pigments or azo pigments. In the case where an organic pigment is used as a charge generation substance, any of those organic pigments is used usually in the form of a dispersion layer in which fine particles of the organic pigment have been bound with any of various binder resins.

In the case where a phthalocyanine pigment is used as a charge generation substance, usable phthalocyanines specifically include phthalocyanines having different crystal forms such as metal-free phthalocyanine and phthalocyanine compounds to which a metal, e.g., copper, indium, gallium, tin, titanium, zinc, vanadium, silicon, germanium, or aluminum, or an oxide, halide, hydroxide, alkoxide, or another form of the metal has coordinated, and further include phthalocyanine dimmers or the like in which an oxygen atom or the like is used as a crosslinking atom. Especially suitable are X-form and τ-form metal-free phthalocyanines, which are crystal forms having high sensitivity, A-form (also called β-form), B-form (also called α-form), D-form (also called Y-form), and other titanyl phthalocyanines (another name: oxytitanium phthalocyanines), vanadyl phthalocyanines, chloroindium phthalocyanines, hydroxyindium phthalocyanines, II-form and other chlorogallium phthalocyanines, V-form and other hydroxygallium phthalocyanines, G-form, I-form, and other μ-oxogallium phthalocyanine dimers, and II-form and other μ-oxoaluminum phthalocyanine dimers.

Especially preferred of these phthalocyanines are A-form (also called β-form), B-form (also called α-form), D-form (Y-form) titanyl phthalocyanine which shows a distinct peak at a Bragg angle (diffraction angle) $(2\theta \pm 0.2°)$ of 27.2° in X-ray powder diffractometry using a KCuKα characteristics X-ray line, II-form chlorogallium phthalocyanine, V-form hydroxygallium phthalocyanine, hydroxygallium phthalocyanine which has a highest peak at 28.1°, hydroxygallium phthalocyanine which has no peak at a Bragg angle $(2\theta \pm 0.2°)$ of 26.2° but has a distinct peak at 28.1° and which has a half-value width at 25.9°, W, of $0.1° \leq W \leq 0.4°$, G-form μ-oxogallium phthalocyanine dimer, and the like. Most preferred is D-form (Y-form) titanyl phthalocyanine (oxytitanium phthalocyanine) which shows peaks at least at Bragg angles $(2\theta \pm 0.2°)$ of 24.1° and 27.2°.

In the case where a metal-free phthalocyanine compound or a metal-containing phthalocyanine compound is used as a charge generation substance, a photoreceptor which is highly sensitive to relatively long-wavelength laser light, e.g., laser light having a wavelength of about 780 nm, is obtained. In the case where an azo pigment such as a monoazo, diazo, or trisazo pigment is used, it is possible to obtain a photoreceptor which has sufficient sensitivity to white light, laser light having a wavelength of about 660 nm, or laser light having a relatively short wavelength (e.g., laser light having a wavelength in the range of 380-500 nm).

A single phthalocyanine compound may be used alone, or a mixture of some phthalocyanine compounds or a mixture of some crystal states may be used. This mixed state of phthalocyanine compounds or of crystal states to be used here may be a mixture obtained by mixing the components prepared beforehand, or may be a mixture which came into the mixed state during phthalocyanine compound production/treatment steps such as synthesis, pigment formation, crystallization, etc. Known as such treatment steps include an acid paste treatment, grinding, solvent treatment, and the like. Examples of methods for obtaining a mixed-crystal state include a method in which two kinds of crystals are mixed, subsequently mechanically ground to render the crystals amorphous, and then subjected to a solvent treatment to convert into specific crystal states, as described in JP-A-10-48859.

Meanwhile, in the case of using an azo pigment as a charge generation material, conventionally known various azo pigments can be used so long as the azo pigments have sensitivity to the light source for light input. However, various kinds of bisazo pigments and trisazo pigments are suitable. Preferred examples of the azo pigments are shown below.

more charge generation substances which have spectral sensitivity characteristics in different spectral regions, i.e., the visible region and the near-infrared region, should be used in combination. More preferred of such methods is to use a disazo pigment or trisazo pigment and a phthalocyanine pigment in combination.

The binder resin to be used for the charge generation layer as a component of the multilayer type photosensitive layer is not particularly limited. Examples thereof include: insulating resins such as poly(vinyl acetal) resins, e.g., poly

[Chem. 20]

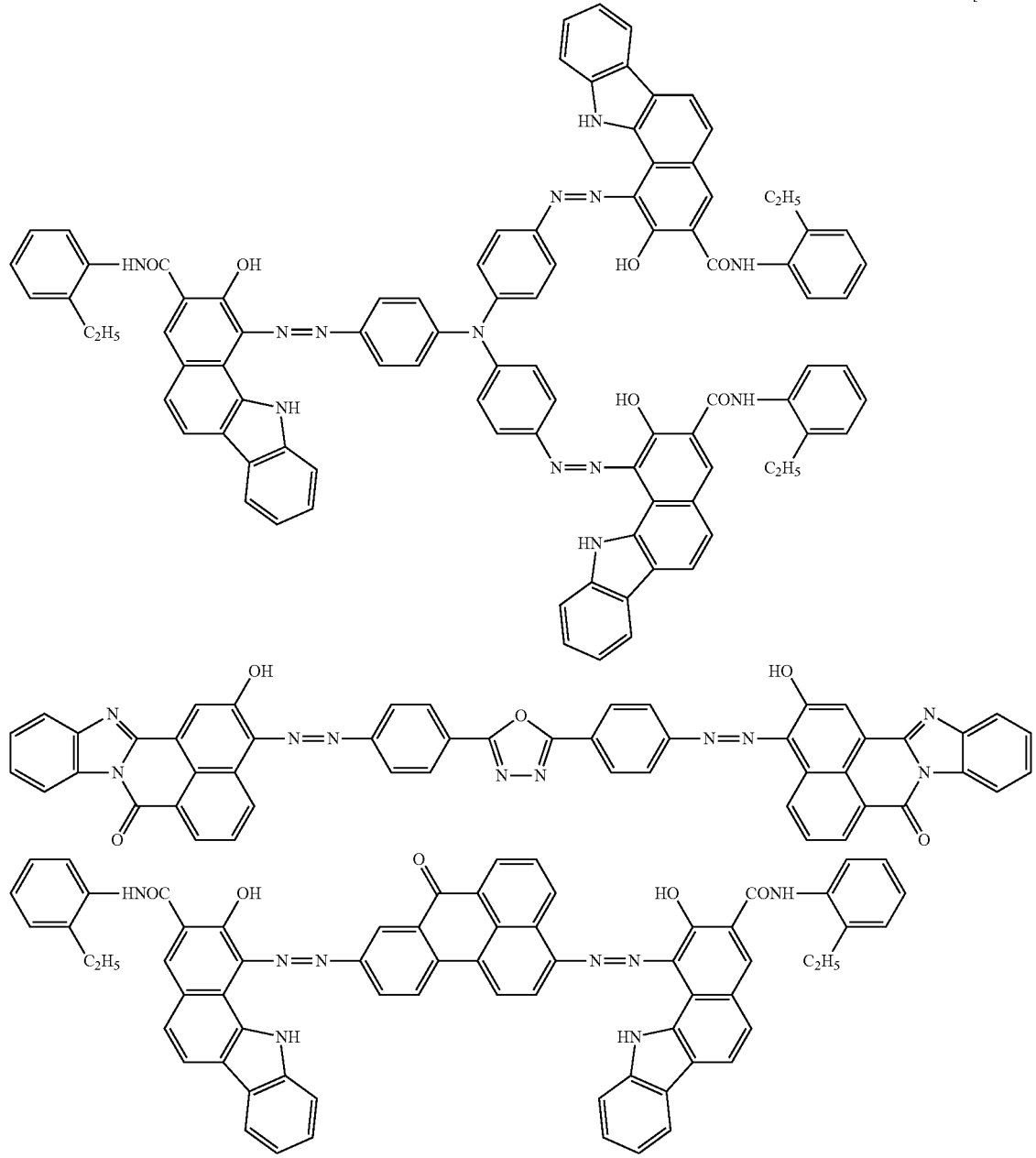

In the case where one or more of the organic pigments (azo pigments) shown above as examples are used as a charge generation substance, two or more pigments may be used as a mixture thereof although one of the azo pigments may be used alone. In this case, it is preferred that two or (vinyl butyral) resins, poly(vinyl formal) resins, and partly acetalized poly(vinyl butyral) resins in which the butyral moieties have been partly modified with formal, acetal, or the like, polyarylate resins, polycarbonate resins, polyester resins, modified ether-type polyester resins, phenoxy resins, poly(vinyl chloride) resins, poly(vinylidene chloride) resins, poly(vinyl acetate) resins, polystyrene resins, acrylic resins, methacrylic resins, polyacrylamide resins, polyamide resins, polyvinylpyridine resins, cellulosic resins, polyurethane resins, epoxy resins, silicone resins, poly(vinyl alcohol) resins, polyvinylpyrrolidone resins, casein, copolymers based on vinyl chloride and vinyl acetate, e.g., vinyl chloride/vinyl acetate copolymers, hydroxy-modified vinyl chloride/vinyl acetate copolymers, carboxyl-modified vinyl chloride/vinyl acetate copolymers, and vinyl chloride/vinyl acetate/maleic anhydride copolymers, styrene/butadiene copolymers, vinylidene chloride/acrylonitrile copolymers, styrene-alkyd resins, silicone-alkyd resins, and phenol-formaldehyde resins; and organic photoconductive polymers such as poly-N-vinylcarbazole, polyvinylanthracene, and polyvinylperylene. Any one of these binder resins may be used alone, or any desired two or more thereof may be used as a mixture thereof.

The charge generation layer is formed specifically by dissolving the binder resin described above in an organic solvent, dispersing a charge generation substance in the resultant solution to prepare a coating fluid, and applying this coating fluid on a conductive support (or on an undercoat layer when the undercoat layer has been disposed).

The solvent to be used for producing the coating fluid is not particularly limited so long as the binder resin dissolves therein. Examples thereof include saturated aliphatic solvents such as pentane, hexane, octane, and nonane, aromatic solvents such as toluene, xylene, and anisole, halogenated aromatic solvents such as chlorobenzene, dichlorobenzene, and chloronaphthalene, amide solvents such as dimethylformamide and N-methyl-2-pyrrolidone, alcohol solvents such as methanol, ethanol, isopropanol, n-butanol, and benzyl alcohol, aliphatic polyhydric alcohols such as glycerol and polyethylene glycol, chain or cyclic ketone solvents such as acetone, cyclohexanone, methyl ethyl ketone, and 4-methoxy-4-methyl-2-pentanone, ester solvents such as methyl formate, ethyl acetate, and n-butyl acetate, halogenated hydrocarbon solvents such as methylene chloride, chloroform, and 1,2-dichloroethane, chain or cyclic ether solvents such as diethyl ether, dimethoxyethane, tetrahydrofuran, 1,4-dioxane, methyl Cellosolve, and ethyl Cellosolve, aprotic polar solvents such as acetonitrile, dimethyl sulfoxide, sulfolane, and hexamethylphosphoric triamide, nitrogen-containing compounds such as n-butylamine, isopropanolamine, diethylamine, triethanolamine, ethylenediamine, triethylenediamine, and triethylamine, mineral oils such as ligroin, and water. One of these solvents may be used alone, or two or more thereof may be used in combination. In the case where the undercoat layer described above is disposed, solvents in which this undercoat layer does not dissolve are preferred.

In the charge generation layer, the ratio (mass ratio) of the binder resin and the charge generation substance is in such a range that the amount of the charge generation substance per 100 parts by mass of the binder resin is usually 10 parts by mass or larger, preferably 30 parts by mass or larger, and is usually 1,000 parts by mass or less, preferably 500 parts by mass or less. In case where the proportion of the charge generation substance to the binder resin is too high, there is a possibility that the coating fluid might have reduced stability due to the aggregation of the charge generation substance, etc. Meanwhile, in case where the proportion of the charge generation substance to the binder resin is too low, there is the possibility of resulting in a decrease in the sensitivity of the photoreceptor. The thickness of the charge generation layer is usually 0.1 µm or larger, preferably 0.15 µm or larger, and is usually 10 µM or less, preferably 0.6 µm or less.

For dispersing the charge generation substance, known dispersing techniques can be used, such as ball mill dispersion, attritor dispersion, and sand mill dispersion. In this case, it is preferred to finely reduce the particles to a particle size of 0.5 µm or less, preferably 0.3 µm or less, more preferably 0.15 µm or less.

<Charge Transport Layer>

The charge transport layer of the multilayer type photoreceptor contains a charge transport substance and usually further contains a binder resin and other ingredients which are used according to need. Such a charge transport layer can be obtained, specifically, by dissolving or dispersing a charge transport substance, etc. and a binder resin in a solvent to produce a coating fluid, applying this coating fluid on the charge generation layer in the case of a normal-superposition type photosensitive layer or applying the coating fluid on a conductive support (or on an undercoat layer when the undercoat layer has been disposed) in the case of a reverse-superposition type photosensitive layer, and drying the coating fluid applied.

Preferred as the charge transport substance is a charge transport substance represented by the formula (1) or formula (2) described above. A known charge transport substance may be further used in combination with a charge transport substance represented by the formula (1) or formula (2) described above. In the case of using another charge transport substance in combination with the charge transport substance represented by formula (1) or (2), the kind thereof is not particularly limited. However, preferred charge transport substances which can be optionally used are, for example, carbazole derivatives, hydrazone compounds, aromatic amine derivatives, enamine derivatives, butadiene derivatives, and compounds each constituted of two or more of these derivatives bonded to each other. Any one of these charge transport substances may be used alone, or any desired two or more thereof may be used in combination.

From the standpoint of enabling the charge transport substance of the invention to exhibit the effects thereof, the proportion of the charge transport substance represented by formula (1) or formula (2) of the invention to all charge transport substances is usually 10% by mass or higher. The proportion thereof is preferably 30% by mass or higher from the standpoint of the photo-decay characteristics of the electrophotographic photoreceptor, and is more preferably 50% by mass or higher, especially preferably 70% by mass or higher, from the standpoint of the high-speed responsiveness of the electrophotographic photoreceptor.

The binder resin is used in order to ensure film strength. Examples of the binder resin for use in the charge transport layer include butadiene resins, styrene resins, vinyl acetate resins, vinyl chloride resins, acrylic ester resins, methacrylic ester resins, vinyl alcohol resins, polymers and copolymers of vinyl compounds, e.g., ethyl vinyl ether, poly(vinyl butyral) resins, poly(vinyl formal) resins, partly modified poly(vinyl acetal)s, polycarbonate resins, polyester resins, polyarylate resins, polyamide resins, polyurethane resins, cellulose ester resins, phenoxy resins, silicone resins, silicone-alkyd resins, and poly-N-vinylcarbazole resins. Preferred of these are polycarbonate resins and polyarylate resins. It is possible to use an appropriate hardener to crosslink these binder resins by means of heat, light, or the like. Any one of those binder resins may be used alone, or any desired two or more thereof may be used in combination.

With respect to the ratio of the binder resin and the charge transport substance in the charge transport layer, the charge transport substance may be used in a proportion of 10 parts by mass or more per 100 parts by mass of the binder resin. In particular, the proportion of the charge transport substance is preferably 20 parts by mass or more from the standpoint of reducing residual potential, and is more preferably 30 parts by mass or more from the standpoints of stability and charge mobility during repeated use. Meanwhile, from the standpoint of the thermal stability of the photosensitive layer, the charge transport substance is used in a proportion of usually 120 parts by mass or less per 100 parts by mass of the binder resin. In particular, the proportion of the charge transport substance is preferably 100 parts by mass or less from the standpoint of compatibility between the charge transport material and the binder resin, more preferably 90 parts by mass or less from the standpoint of printing durability, and most preferably 80 parts by mass or less from the standpoint of scratch resistance.

The thickness of the charge transport layer is not particularly limited. However, from the standpoints of long life and image stability and of high resolution, the thickness thereof is usually 5 μm or larger, preferably 10 μm or larger, but is usually 50 μm or less, preferably 45 μm or less, more preferably 30 μm or less.

<Single-Layer Type Photosensitive Layer>

The single-layer type photosensitive layer is formed using a charge generation substance and a charge transport substance and further using a binder resin in order to ensure film strength as in the charge transport layer of the multilayer type photoreceptor. Specifically, the single-layer type photosensitive layer can be obtained by dissolving or dispersing a charge generation substance, a charge transport substance, and any of various binder resins in a solvent to produce a coating fluid, applying the coating fluid on a conductive support (or on an undercoat layer when the undercoat layer has been disposed), and drying the coating fluid applied.

The kinds of the charge transport substance and binder resin and the ratio of these ingredients to be used are the same as explained above with regard to the charge transport layer of the multilayer type photoreceptor. A charge generation substance is further dispersed in a charge transport medium including the charge transport substance and binder resin.

As the charge generation substance, the same charge generation substances as those explained above with regard to the charge generation layer of the multilayer type photoreceptor can be used. In the case of the photosensitive layer of the single-layer type photoreceptor, however, it is necessary to regulate the charge generation substance so as to have a sufficiently reduced particle diameter. Specifically, the particle diameter of the charge generation substance is regulated to usually 1 μm or less, preferably 0.5 μm or less.

With respect to the amount of the charge generation substance dispersed in the single-layer type photosensitive layer, too small amounts thereof make it impossible to obtain sufficient sensitivity, while too large amounts thereof exert adverse influences to result in a decrease in charging property, decrease in sensitivity, etc. Consequently, the charge generation substance is used in an amount which is usually 0.5% by mass or larger, preferably 1% by mass or larger, and is usually 50% by mass or less, preferably 20% by mass or less, based on the whole single-layer type photosensitive layer.

With respect to the ratio of the binder resin and charge generation substance used in the single-layer type photosensitive layer, the proportion of the charge generation substance per 100 parts by mass of the binder resin is usually 0.1 part by mass or larger, preferably 1 part by mass or larger, and is usually 30 parts by mass or less, preferably 10 parts by mass or less.

The thickness of the single-layer type photosensitive layer is usually 5 μm or larger, preferably 10 μm or larger, and is usually 100 μm or less, preferably 50 μm or less.

<Other Functional Layers>

Known additives, e.g., an antioxidant, plasticizer, ultraviolet absorber, electron-attracting compound, leveling agent, and visible-light-shielding agent, may be incorporated into the photosensitive layer of each of the multilayer type photoreceptor and the single-layer type photoreceptor or into the layers constituting the photosensitive layer, for the purpose of improving film-forming properties, flexibility, applicability, nonfouling properties, gas resistance, light resistance, etc.

In either the multilayer type photoreceptor or the single-layer type photoreceptor, the photosensitive layer formed in the manner described above may be the uppermost layer, i.e., the surface layer thereof. It is, however, possible to further dispose another layer as a surface layer on the photosensitive layer. For example, a protective layer may be disposed for the purpose of preventing the photosensitive layer from being damaged or wearing or of preventing or lessening the deterioration of the photosensitive layer caused by, for example, discharge products generated from the charging device, etc.

The protective layer can be formed from a mixture obtained by incorporating a conductive material into an appropriate binder resin, or can be formed using the copolymer described in JP-A-9-190004, which is produced using a compound having charge-transporting ability, e.g., a triphenylamine framework.

As the conductive material for the protective layer, use can be made of aromatic amino compounds such as TPD (N,N'-diphenyl-N,N'-bis(m-tolyl)benzidine), metal oxides such as antimony oxide, indium oxide, tin oxide, titanium oxide, tin oxide/antimony oxide, aluminum oxide, and zinc oxide, and the like. However, the conductive material is not limited to these examples.

As the binder resin for the protective layer, use can be made of known resins such as polyamide resins, polyurethane resins, polyester resins, epoxy resins, polyketone resins, polycarbonate resins, poly(vinyl ketone) resins, polystyrene resins, polyacrylamide resins, and siloxane resins. It is also possible to use a copolymer of a framework having charge-transporting ability, e.g., a triphenylamine framework, with any of those resins, such as the copolymer described in JP-A-9-190004.

The protective layer has an electrical resistance usually in the range of $10^9$-$10^{14}$ Ω·cm. In case where the electrical resistance thereof is higher than that range, the photoreceptor has an elevated residual potential to give fogged images. Meanwhile, in case where the electrical resistance thereof is lower than that range, there is the possibility of resulting in image blurring and a decrease in resolution. The protective layer must be configured so that this layer does not substantially prevent the light irradiated for image-wise exposure from passing therethrough.

A fluororesin, silicone resin, polyethylene resin, or the like, particles of any of these resins, or particles of an inorganic compound may be incorporated into the surface layer for the purposes of reducing the frictional resistance and wear of the photoreceptor surface, heightening the efficiency of toner transfer from the photoreceptor to a transfer belt and to paper, etc. Alternatively, a layer containing any of these resins or such particles may be newly formed as a surface layer.

<Method for Forming Each Layer>

The layers for constituting the photoreceptor are formed in the following manner. The substances to be incorporated into each layer are dissolved or dispersed in a solvent to obtain a coating fluid. The coating fluids thus obtained for the respective layers are successively applied on a conductive support by a known technique, such as dip coating, spray coating, nozzle coating, bar coating, roll coating, or blade coating, and dried. By repeating this application/drying step for each layer, the constituent layers are formed.

The solvent or dispersion medium to be used for producing the coating fluids is not particularly limited. However, examples thereof include alcohols such as methanol, ethanol, propanol, and 2-methoxyethanol, ethers such as tetrahydrofuran, 1,4-dioxane, and dimethoxyethane, esters such as methyl formate and ethyl acetate, ketones such as acetone, methyl ethyl ketone, cyclohexanone, and 4-methoxy-4-methyl-2-pentanone, aromatic hydrocarbons such as benzene, toluene, and xylene, chlorinated hydrocarbons such as dichloromethane, chloroform, 1,2-dichloroethane, 1,1,2-trichloroethane, 1,1,1-trichloroethane, tetrachloroethane, 1,2-dichloropropane, and trichloroethylene, nitrogen-containing compounds such as n-butylamine, isopropanolamine, diethylamine, triethanolamine, ethylenediamine, and triethylenediamine, and aprotic polar solvents such as acetonitrile, N-methylpyrrolidone, N,N-dimethylformamide, and dimethyl sulfoxide. One of these compounds may be used alone, or any desired two or more compounds of any desired kind(s) may be used in combination.

The amount of the solvent or dispersion medium to be used is not particularly limited. It is, however, preferred to suitably regulate the amount thereof so that the properties of the coating fluid, such as solid concentration and viscosity, are within desired ranges, while taking account of the purpose of each layer and the nature of the selected solvent or dispersion medium.

For example, in the case of the single-layer type photoreceptor and of the charge transport layer of the function allocation type photoreceptor, the solid concentration of each coating fluid is usually 5% by mass or higher, preferably 10% by mass or higher, and is usually 40% by mass or less, preferably 35% by mass or less. Furthermore, the viscosity of this coating fluid, as measured at the temperature at which the coating fluid is used, is usually 10 mPa·s or higher, preferably 50 mPa·s or higher, and is usually 500 mPa·s or less, preferably 400 mPa·s or less.

Meanwhile, in the case of the charge generation layer of the multilayer type photoreceptor, the solid concentration of the coating fluid is usually 0.1% by mass or higher, preferably 1% by mass or higher, and is usually 15% by mass or less, preferably 10% by mass or less. The viscosity of this coating fluid, as measured at the temperature at which the coating fluid is used, is usually 0.01 mPa·s or higher, preferably 0.1 mPa·s or higher, and is usually 20 mPa·s or less, preferably 10 mPa·s or less.

Examples of techniques for applying the coating fluids include dip coating, spray coating, spinner coating, bead coating, wire-wound bar coating, blade coating, roller coating, air-knife coating, and curtain coating. It is also possible to use other known coating techniques.

In a preferred method for drying each coating fluid, the coating fluid applied is dried at room temperature until the coating film becomes dry to the touch, and is thereafter dried with heating at a temperature usually in the range of 30-200° C. for a period of 1 minute to 2 hours, stationarily or with air blowing. The heating temperature may be constant, or the heating for drying may be conducted while changing the temperature.

<<Image-Forming Apparatus>>

Next, embodiments of the image-forming apparatus (image-forming apparatus of the invention) which employs the electrophotographic photoreceptor of the invention are explained by reference to FIG. 1, which illustrates the configuration of important parts of the apparatus. It is, however, noted that embodiments of the apparatus are not limited to the following explanations and the apparatus can be modified at will unless the modifications depart from the spirit of the invention.

As shown in FIG. 1, the image-forming apparatus is configured so as to be equipped with an electrophotographic photoreceptor 1, a charging device 2, an exposure device 3, and a developing device 4. The apparatus is further provided with a transfer device 5, a cleaner 6, and a fixing device 7 according to need.

The electrophotographic photoreceptor (hereinafter also referred to simply as "photoreceptor") 1 is not particularly limited so long as it is the electrophotographic photoreceptor of the invention described above. FIG. 1 shows, as an example thereof, a drum-shaped photoreceptor obtained by forming the photosensitive layer described above on the surface of a cylindrical conductive support. The charging device 2, exposure device 3, developing device 4, transfer device 5, and cleaner 6 have been disposed along the peripheral surface of this electrophotographic photoreceptor 1.

The charging device 2 serves to charge the electrophotographic photoreceptor 1. This device evenly charges the surface of the electrophotographic photoreceptor 1 to a given potential. Suitable for use as the charging device 2 is a corona charging device, such as a corotron or a scorotron, a direct charging device in which a direct charging member to which a voltage is being applied is brought into contact with the photoreceptor surface to charge the surface (contact type charging device), or the like. Examples of the direct charging device include charging rollers and charging brushes. FIG. 1 shows a roller type charging device (charging roller) as an example of the charging device 2. Either charging which is accompanied with aerial discharge or injection charging which is not accompanied with aerial discharge is a possible means for direct charging. As the voltage to be applied for the charging, a direct-current voltage only can be used or an alternating current superimposed on a direct current is also usable.

The exposure device 3 is not particularly limited in the kind thereof so long as the device can illuminate the electrophotographic photoreceptor 1 and thereby form an electrostatic latent image on the photosensitive surface of the electrophotographic photoreceptor 1. Examples thereof include halogen lamps, fluorescent lamps, lasers such as semiconductor lasers and He—Ne lasers, and LEDs. It is also possible to conduct exposure by the technique of internal photoreceptor exposure. Any desired light may be used for exposure. For example, monochromatic light having a wavelength of 780 nm, monochromatic light having a slightly short wavelength of 600-700 nm, monochromatic light having a short wavelength of 380-500 nm, or the like may be used to conduct exposure.

The developing device 4 is not particularly limited in the kind thereof, and any desired device can be used, such as a device operated by a dry development technique, e.g., cascade development, development with one-component insulating toner, development with one-component conductive toner, or two-component magnetic-brush development, or by a wet development technique, etc. In FIG. 1, the developing device 4 includes a developing vessel 41, agitators 42, a feed roller 43, a developing roller 44, and a control member 45. This device has been configured so that a toner T is stored in the developing vessel 41. According to need, the developing device 4 may be equipped with a replenishing device (not shown) for replenishing the toner T. This replenishing device is configured so that the toner T can be replenished from a container, e.g., a bottle or a cartridge.

The feed roller 43 is made of a conductive sponge, etc. The developing roller 44 is constituted of, for example, a metallic roll made of iron, stainless steel, aluminum, nickel, or the like or a resinous roll obtained by coating such a metallic roll with a silicone resin, urethane resin, fluororesin, or the like. The surface of this developing roller 44 may be subjected to surface-smoothing processing or surface-roughening processing according to need.

The developing roller 44 is disposed between the electrophotographic photoreceptor 1 and the feed roller 43, and is in contact with both the electrophotographic photoreceptor 1 and the feed roller 43. The feed roller 43 and the developing roller 44 are rotated by a rotation driving mechanism (not shown). The feed roller 43 holds the toner T stored and supplies the toner T to the developing roller 44. The developing roller 44 holds the toner T supplied by the feed roller 43 and brings the toner T into contact with the surface of the electrophotographic photoreceptor 1.

The control member 45 is constituted of a resinous blade made of a silicone resin, urethane resin, or the like, a metallic blade made of stainless steel, aluminum, copper, brass, phosphor bronze, or the like, a blade obtained by coating such as a metallic blade with a resin, etc. This control member 45 is in contact with the developing roller 44, and is pushed against the developing roller 44 with springs or the like at a given force (the linear blade pressure is generally 5-500 g/cm). According to need, this control member 45 may be made to have the function of charging the toner T based on electrification caused by friction with the toner T.

The agitators 42 are each rotated by the rotation driving mechanism. The agitators 42 agitate the toner T and convey the toner T to the feed roller 43 side. A plurality of agitators 42 differing in blade shape, size, etc. may be disposed.

The kind of the toner T is not limited, and a polymerization toner or the like obtained by suspension polymerization, emulsion polymerization, etc. can be used besides a powdery toner. Especially when a polymerization toner is used, this toner preferably is one including toner particles having a small particle diameter of about 4-8 µm. The toner particles to be used can have any of various shapes ranging from a shape close to sphere to a shape which is not spherical, such as a potato shape. Polymerization toners are excellent in terms of evenness of charging and transferability and are suitable for image quality improvement.

The transfer device 5 is not particularly limited in the kind thereof, and use can be made of a device operated by any desired technique selected from an electrostatic transfer technique, pressure transfer technique, adhesive transfer technique, and the like, such as, for example, corona transfer, roller transfer, and belt transfer. Here, the transfer device 5 is a device configured of a transfer charger, transfer roller, transfer belt, or the like disposed so as to face the electrophotographic photoreceptor 1. A given voltage (transfer voltage) which has the polarity opposite to that of the charge potential of the toner T is applied to the transfer device 5, and this transfer device 5 thus serves to transfer the toner image formed on the electrophotographic photoreceptor 1 to recording paper (paper or medium) P.

There are no particular limitations on the cleaner 6, and any desired cleaner can be used, such as a brush cleaner, magnetic brush cleaner, electrostatic brush cleaner, magnetic roller cleaner, or bladed cleaner. The cleaner 6 serves to scrape off the residual toner adherent to the photoreceptor 1 with a cleaning member and thus recover the residual toner. However, when there is little or substantially no toner adherent to the surface of the photoreceptor, the cleaner 6 may be omitted.

The fixing device 7 is configured of an upper fixing member (fixing roller) 71 and a lower fixing member (fixing roller) 72. The upper fixing member 71 or the lower fixing member 72 is equipped with a heater 73 inside. FIG. 1 shows an example in which the upper fixing member 71 is equipped with a heater 73 inside. As each of the upper and lower fixing members 71 and 72, use can be made of a known heat-fixing member such as a fixing roll obtained by coating a metallic tube made of stainless steel, aluminum, or the like with a silicone rubber, a fixing roll obtained by further coating that fixing roll with a Teflon (registered trademark) resin, or a fixing sheet. Furthermore, the fixing members 71 and 72 may be configured so that a release agent such as a silicone oil is supplied thereto in order to improve release properties, or may be configured so that the two members are forcedly pressed against each other with springs or the like.

The toner T which has been transferred to the recording paper P passes through the nip between the upper fixing member 71 heated at a given temperature and the lower fixing member 72, during which the toner T is heated to a molten state. After the passing, the toner is cooled and fixed to the recording paper P.

The fixing device 7 also is not particularly limited in the kind thereof. Fixing devices which are operated by any desired fixing technique, such as heated-roller fixing, flash fixing, oven fixing, or pressure fixing, can be disposed besides the fixing device used here.

In the electrophotographic apparatus having the configuration described above, image recording is conducted in the following manner. First, the surface (photosensitive surface) of the photoreceptor 1 is charged to a given potential (e.g., −600 V) by the charging device 2. This charging may be conducted with a direct-current voltage or with a direct-current voltage on which an alternating-current voltage has been superimposed.

Subsequently, the charged photosensitive surface of the photoreceptor 1 is exposed to light by the exposure device 3 according to the image to be recorded. Thus, an electrostatic latent image is formed on the photosensitive surface. This electrostatic latent image formed on the photosensitive surface of the photoreceptor 1 is developed by the developing device 4.

In the developing device 4, toner T fed by the feed roller 43 is spread into a thin layer on the developing roller 44 with the control member (developing blade) 45 and, simultaneously therewith, frictionally charged so as to have given polarity (here, the toner is charged so as to have negative polarity, which is the same as the polarity of the charge potential of the photoreceptor 1). This toner T is conveyed while being held by the developing roller 44 and is brought into contact with the surface of the photoreceptor 1.

When the toner T held on the developing roller 44 comes into contact with the surface of the photoreceptor 1, a toner image corresponding to the electrostatic latent image is formed on the photosensitive surface of the photoreceptor 1. This toner image is transferred to recording paper P by the transfer device 5. Thereafter, the toner which has not been transferred and remains on the photosensitive surface of the photoreceptor 1 is removed by the cleaner 6.

After the transfer of the toner image to the recording paper P, this recording paper P is passed through the fixing device 7 to thermally fix the toner image to the recording paper P. Thus, a finished image is obtained.

Incidentally, the image-forming apparatus may be configured so that an erase step, for example, can be conducted, besides the configuration described above. The erase step is a step in which the electrophotographic photoreceptor is exposure to light to thereby remove the residual charges from the electrophotographic photoreceptor. As an eraser, use may be made of a fluorescent lamp, LED, or the like. The light to be used in the erase step, in many cases, is light having such an intensity that the exposure energy thereof is at least 3 times that of the exposure light.

The configuration of the image-forming apparatus may be further modified. For example, the apparatus may be configured so that steps such as a pre-exposure step and an auxiliary charging step can be conducted therein, or may be configured so that offset printing is conducted therein. Furthermore, the apparatus may have a full-color tandem configuration in which a plurality of toners are used.

Incidentally, the electrophotographic photoreceptor 1 may be combined with one or more of the charging device 2, exposure device 3, developing device 4, transfer device 5, cleaner 6, and fixing device 7 to constitute an integrated cartridge (hereinafter suitably referred to as "electrophotographic photoreceptor cartridge"), and this electrophotographic photoreceptor cartridge may be used in a configuration in which the cartridge can be demounted from the main body of an electrophotographic apparatus, e.g., copier or laser beam printer. In this case, when the electrophotographic photoreceptor 1 or another member has deteriorated, this electrophotographic photoreceptor cartridge is demounted from the main body of the image-forming apparatus and a fresh electrophotographic photoreceptor cartridge is mounted on the main body of the image-forming apparatus. Thus, maintenance of the image-forming apparatus is facilitated.

EXAMPLES

The invention will be explained below in more detail by reference to Production Examples, Reference Production Examples, Examples, and Comparative Examples. Incidentally, the following Examples are intended to illustrate the invention in detail, and the invention should not be construed as being limited to the following Examples unless the invention departs from the spirit thereof.

<Production of Charge Transport Substances Represented by Formula (1)>

Production Example 1: Example Compound CT1-8

Example compound CT1-8 was produced in accordance with the following scheme 1. Detailed conditions are shown below.

(Scheme 1)

[Chem. 21]

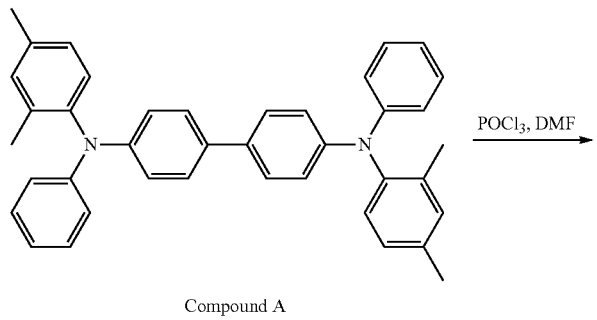

Compound A

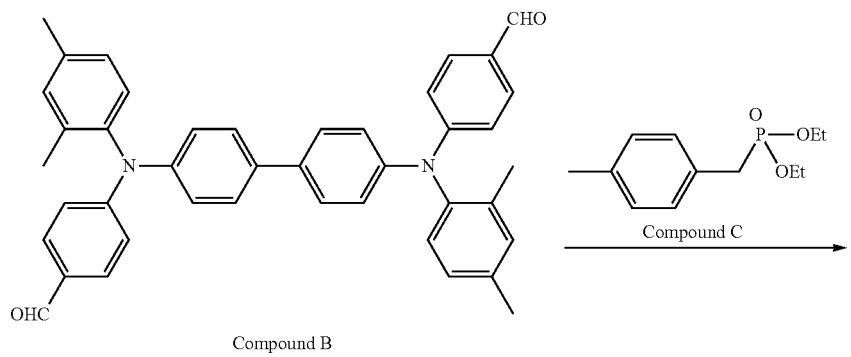

Compound B

-continued

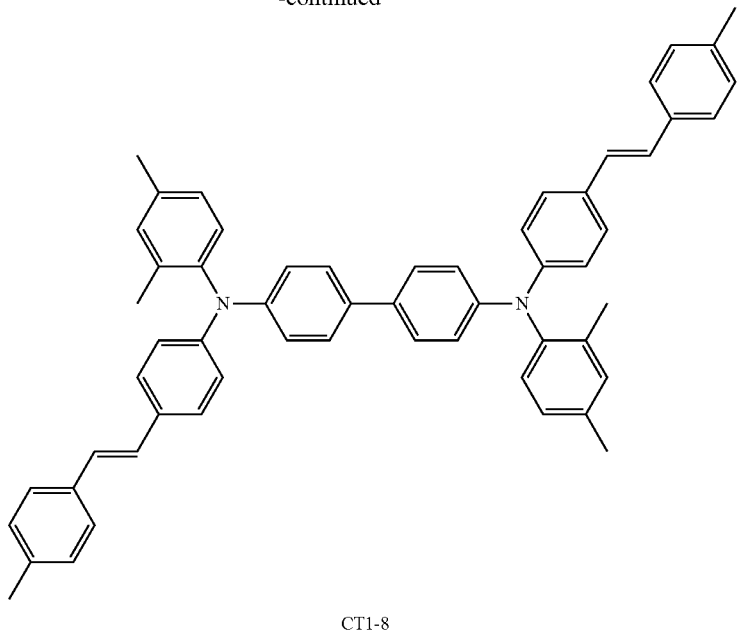

CT1-8

Five grams of compound A, which is a tetraphenylbenzidine derivative, was added to 50 mL of N,N-dimethylformamide (DMF), and this mixture was heated to 60° C. After the heating, 4.3 g of phosphorus oxychloride was added dropwise thereto at 70° C. or lower. After completion of the dropwise addition, the resultant mixture was reacted for 4 hours at a temperature in the range of 60-70° C. After completion of the reaction, the liquid reaction mixture was cooled to room temperature and poured into a liquid mixture of 100 mL of water and 100 mL of toluene to conduct hydrolysis. After the hydrolysis, the organic layer was taken out, washed with an aqueous sodium hydroxide solution and water until the organic layer became neutral, and then concentrated. The resultant residue was purified by silica gel chromatography. Thus, compound B, which is a tetraphenylbenzidine derivative having formyl groups, was obtained in an amount of 4.5 g (yield, 81.8%).

Figure 3:
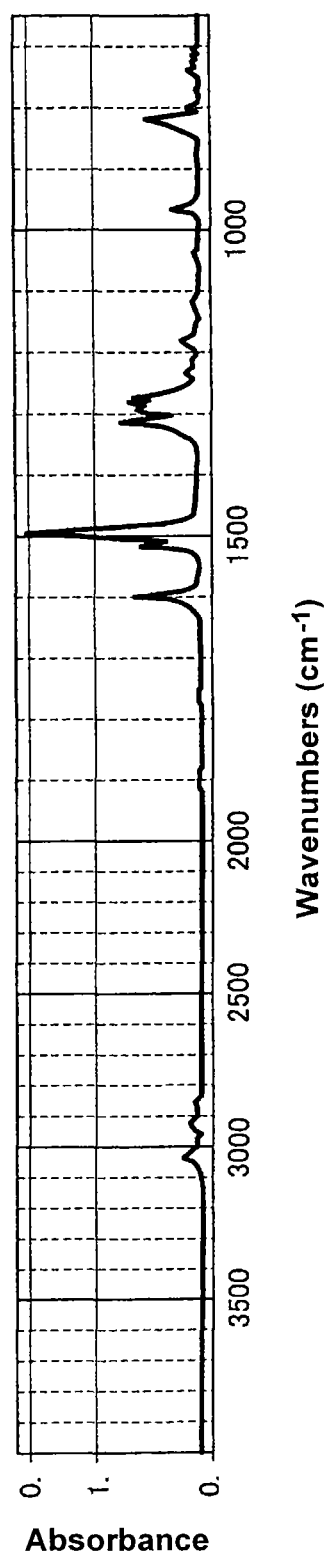
FIG. 3 is an IR chart of example compound CT1-8 obtained in Production Example 1.

To 100 mL of tetrahydrofuran (THF) were added 4.5 g of the formyl compound B and 4.0 g of compound C, which is a phosphoric ester derivative. These compounds were dissolved in the THF. After the dissolution, 2.2 g of t-butoxypotassium was added thereto, and this mixture was stirred at room temperature for 30 minutes and reacted thereby. After completion of the reaction, the liquid reaction mixture was poured into water, and this mixture was extracted with toluene. Thereafter, the organic layer was concentrated, and the resultant residue was purified by silica gel chromatography. Thus, charge transport substance CT1-8, which was the target substance, was obtained in an amount of 4.3 g (yield, 73.8%). The charge transport substance CT1-8 obtained was examined with "Protege 460", manufactured by Nicolet, and the IR chart obtained is shown in FIG. 3.

Production Example 2: Positional-Isomer Mixture Composed of Example Compounds CT1-10, CT1-11, and CT1-12 (Positional-Isomer Mixture Composed of Example Compounds CT2-10, CT2-11, and CT2-12)

Figure 4:
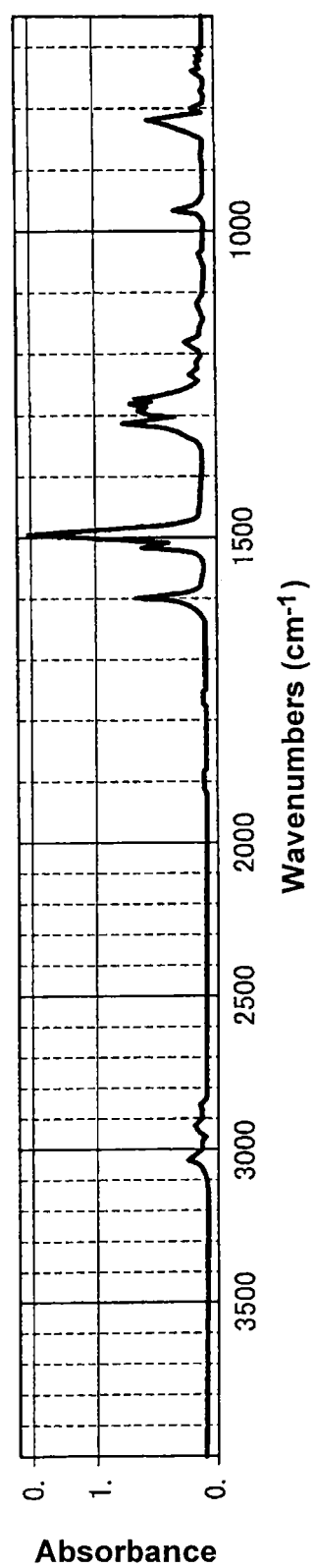
FIG. 4 is an IR chart of example compounds CT1-10 to CT1-12 (corresponding to CT2-10 to CT2-12) obtained in Production Example 2.

The same procedure as in Production Example 1 was conducted, except that the phosphoric ester compound C used in Production Example 1 was replaced with 4.5 g of a positional-isomer mixture composed of the following phosphoric ester compounds D and E (D/E=73/27) and the procedure was conducted in accordance with the following scheme 1-1. Thus, a positional-isomer mixture composed of CT1-10, CT1-11, and CT1-12, which were the target charge transport substances, was obtained in an amount of 4.4 g (yield, 70.1%). The composition of the positional-isomer mixture obtained was determined by examining the mixture by $^{1}$H-NMR (nuclear magnetic resonance) spectroscopy (composition: CT1-10/CT1-11/CT1-12=54/39/7). The IR chart obtained by examining the obtained positional-isomer mixture with "Protege 460", manufactured by Nicolet, is shown in FIG. 4.

(Scheme 1-1)
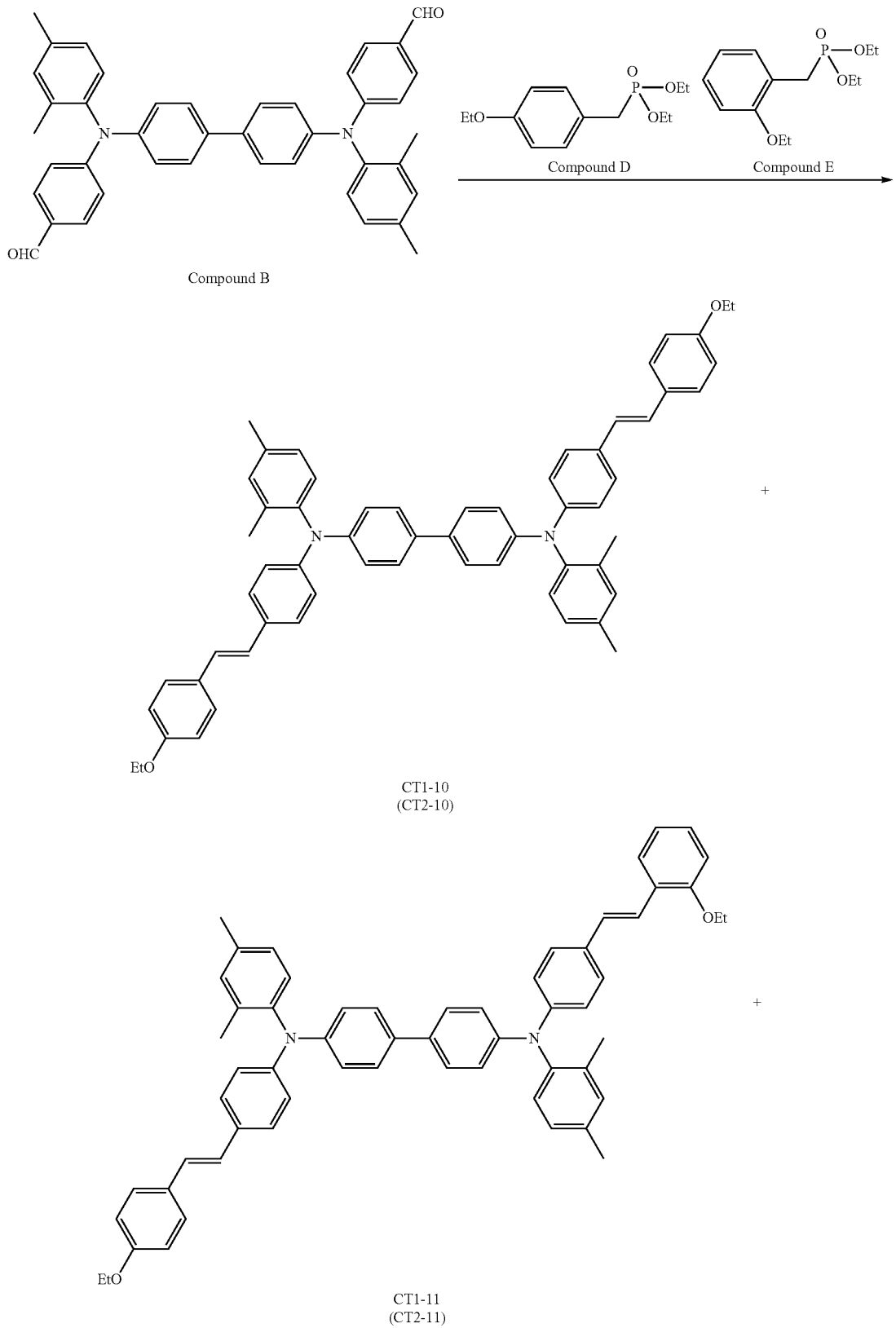

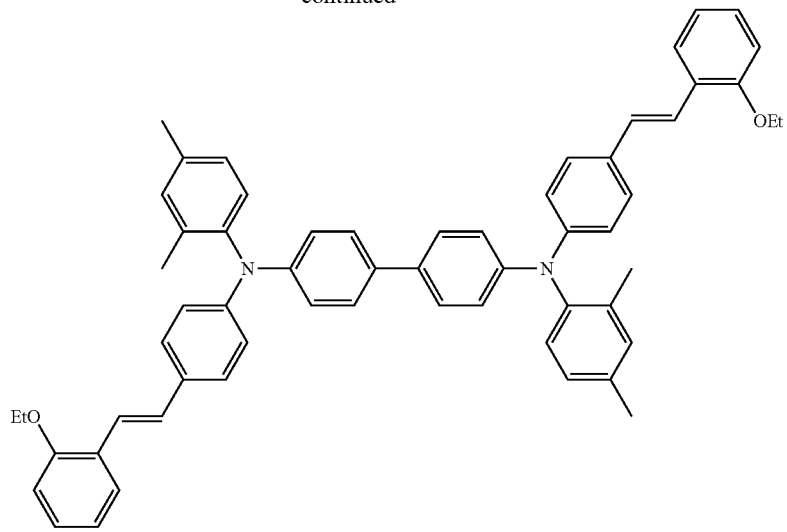

CT1-12
(CT2-12)

Production Example 3: Example Compound CT1-7

Figure 5:
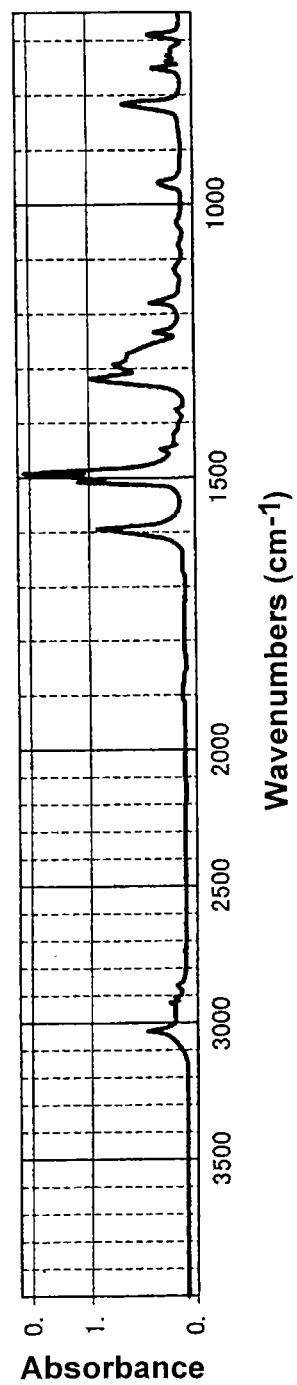
FIG. 5 is an IR chart of example compound CT1-7 obtained in Production Example 3.

The same procedure as in Production Example 1 was conducted, except that the phosphoric ester compound C used in Production Example 1 was replaced with 3.8 g of the following phosphoric ester compound F and the procedure was conducted in accordance with the following scheme 1-2. Thus, CT1-7, which was the target charge transport substance, was obtained in an amount of 4.0 g (yield, 71.3%). The IR chart obtained by examining the obtained charge transport substance CT1-7 with "Protege 460", manufactured by Nicolet, is shown in FIG. 5.

(Scheme 1-2)

[Chem. 23]

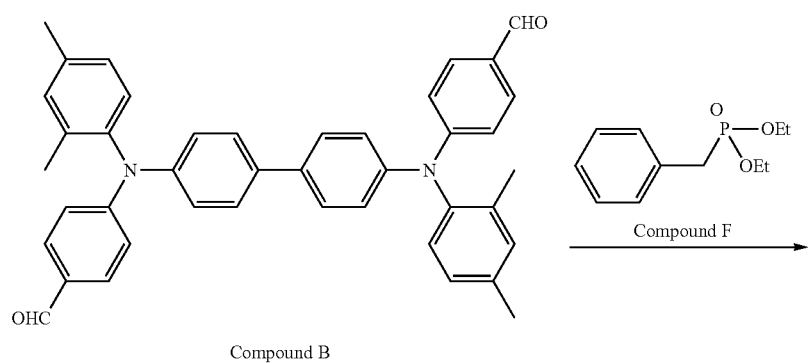

Compound B

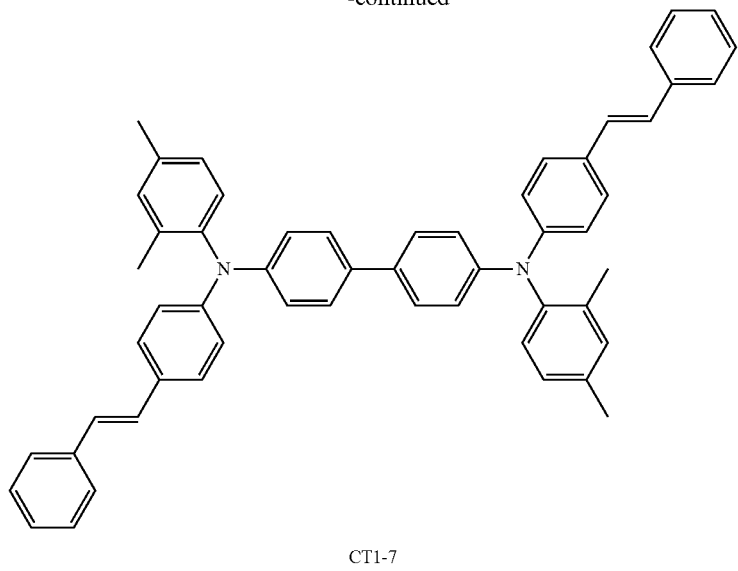

CT1-7

Production Example 4: Example Compound CT1-37

Figure 6:
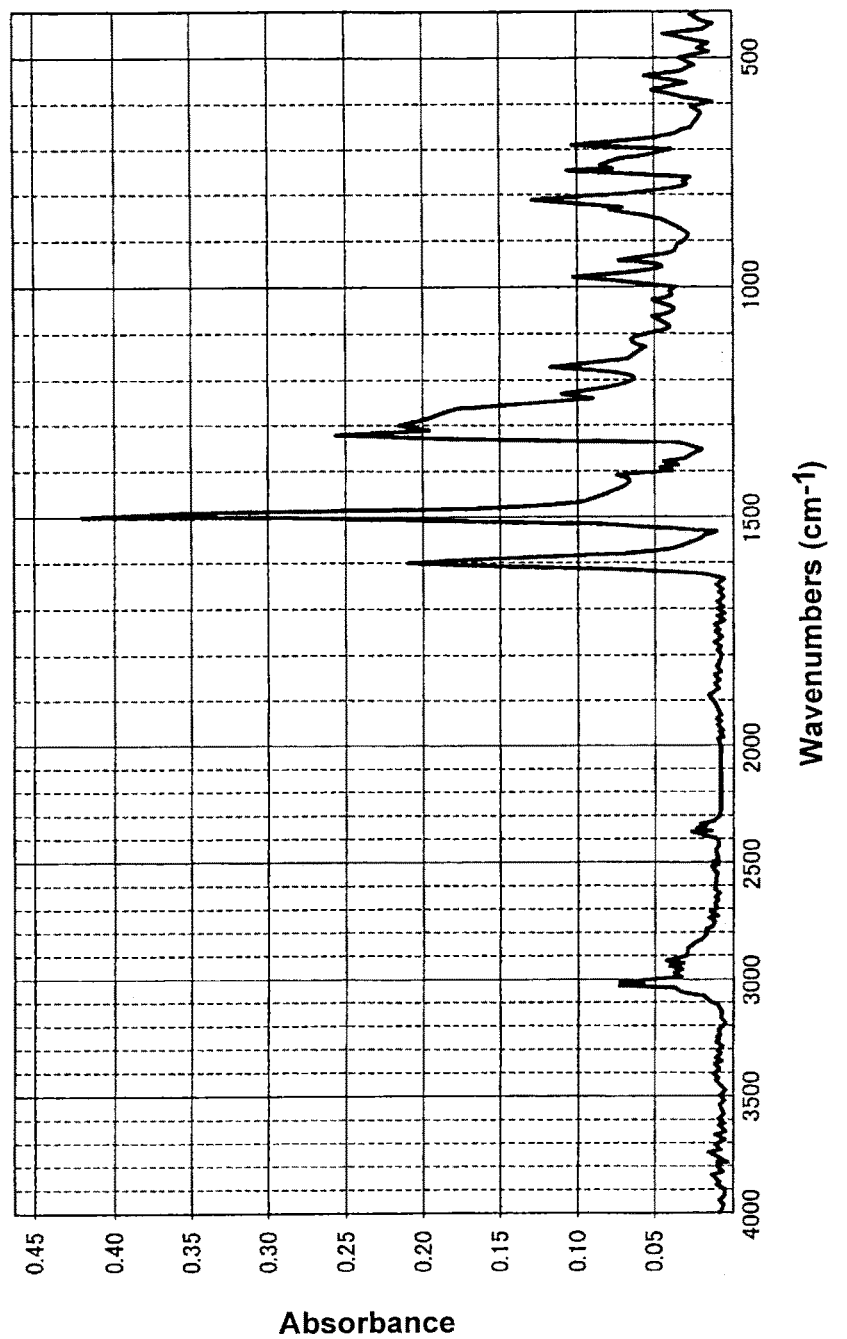
FIG. 6 is an IR chart of example compound CT1-37 obtained in Production Example 4.

To 100 mL of THF was added 6.0 g of the formyl compound B. The compound was dissolved in the THF. After the dissolution, 9.2 g of cinnamyltriphenylphosphonium chloride (compound G) was added thereto in accordance with the following scheme 1-3, and the solution was cooled to 0° C. or lower. After the cooling, 4.8 g of a 28% methanol solution of sodium methoxide was added thereto, and this mixture was stirred at 0° C. or lower for 30 minutes and reacted thereby. After completion of the reaction, the liquid reaction mixture was poured into water, and this mixture was extracted with toluene. Thereafter, the organic layer was concentrated, and the resultant residue was purified by silica gel chromatography. Thus, charge transport substance CT1-37, which was the target substance, was obtained in an amount of 6.3 g (yield, 78.6%). The IR chart obtained by examining the obtained charge transport substance CT1-37 with "Protege 460", manufactured by Nicolet, is shown in FIG. 6.

(Scheme 1-3)

[Chem. 24]

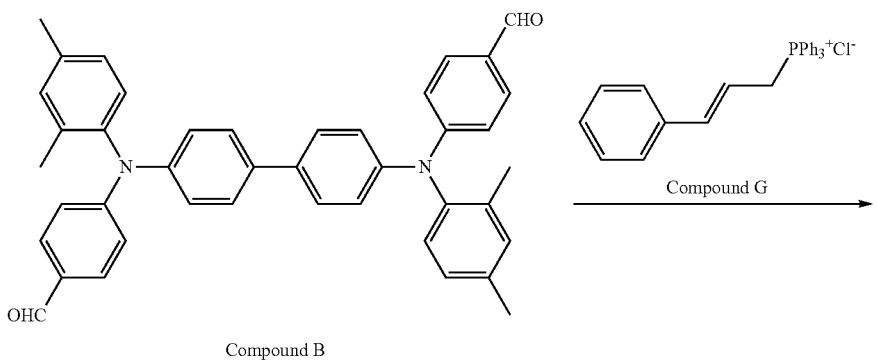

Compound B

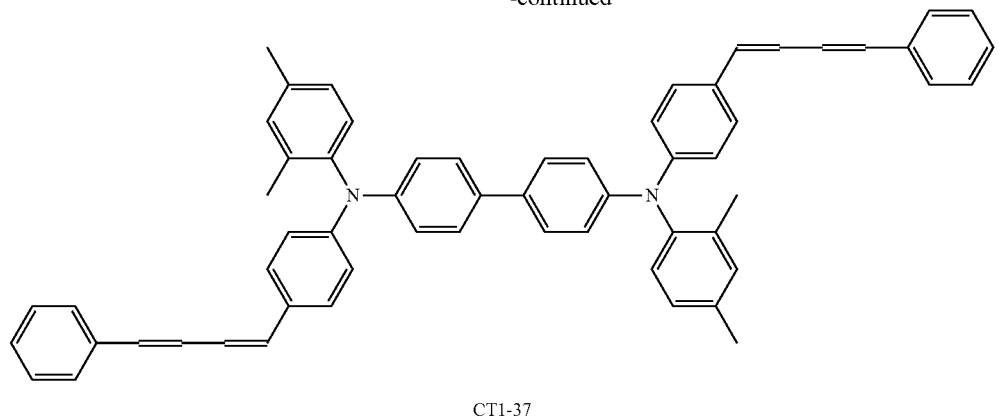
CT1-37
Production Example 5: Positional-Isomer Mixture Composed of Example Compounds CT2-7, CT2-8, and CT2-9
A positional-isomer mixture composed of example compounds CT2-7, CT2-8, and CT2-9 was produced in accordance with the following scheme 2. Detailed conditions are shown below.
(Scheme 2)
[Chem. 25]
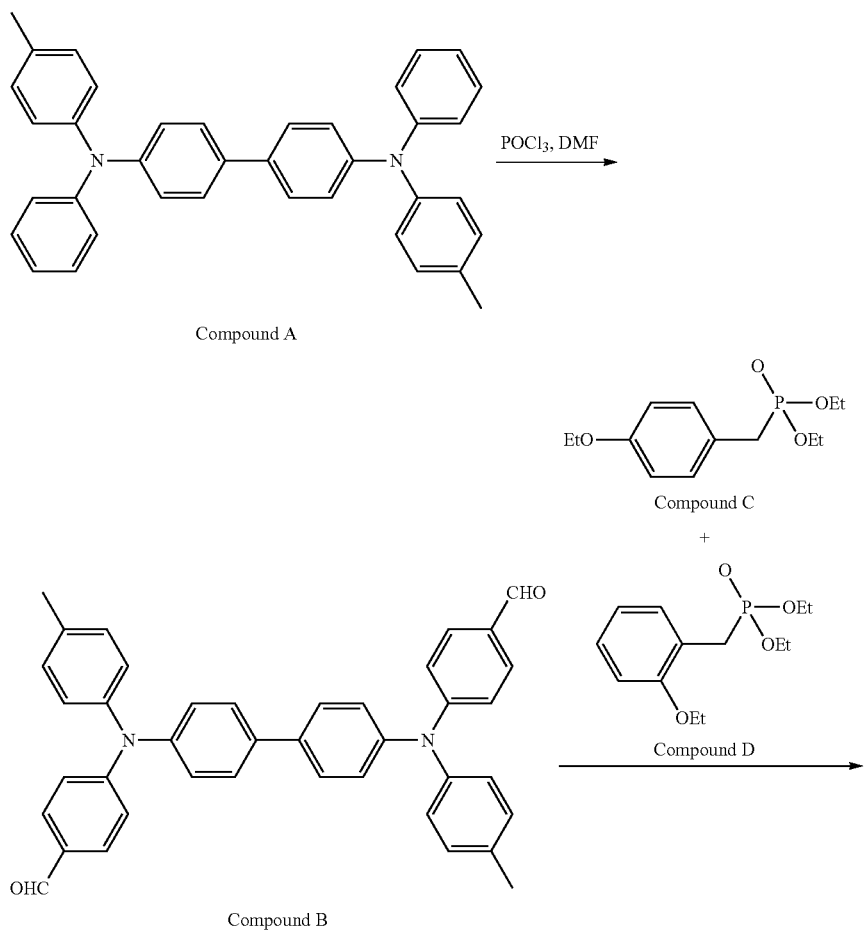

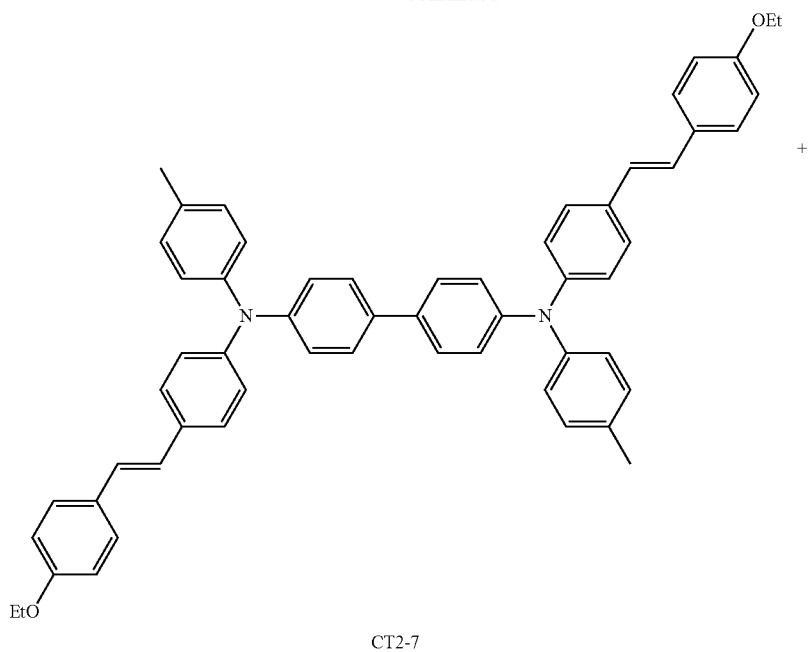
CT2-7
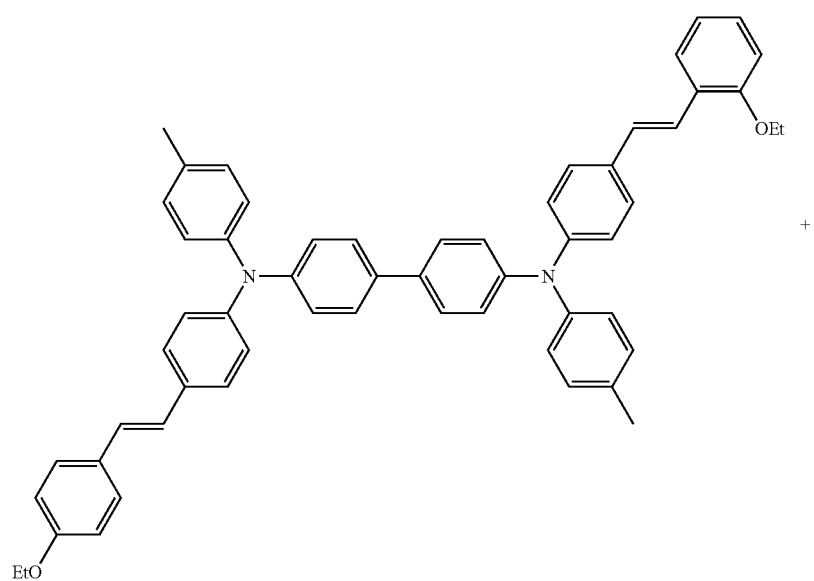
CT2-8

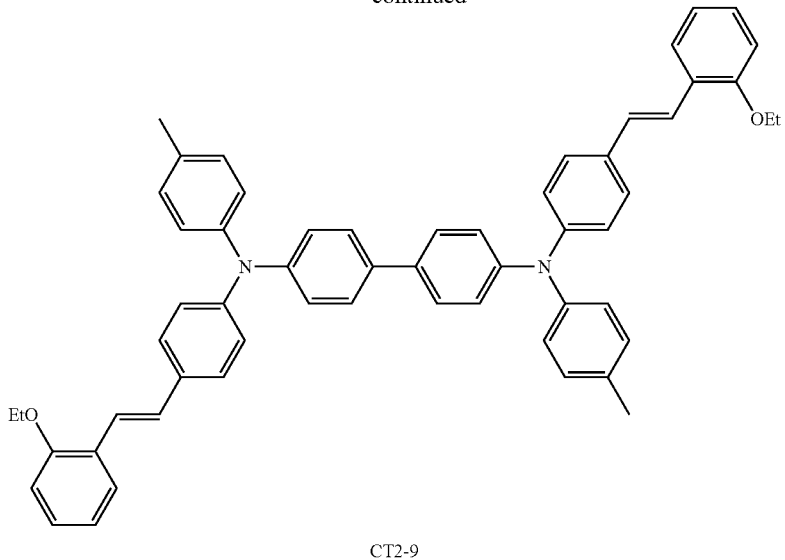

CT2-9

Five grams of compound A, which is a tetraphenylbenzidine derivative, was added to 50 mL of DMF, and this mixture was heated to 60° C. After the heating, 4.4 g of phosphorus oxychloride was added dropwise thereto at 70° C. or lower. After completion of the dropwise addition, the resultant mixture was reacted for 4 hours at a temperature in the range of 65-75° C. After completion of the reaction, the liquid reaction mixture was cooled to room temperature and poured into a liquid mixture of 100 mL of water and 100 mL of toluene to conduct hydrolysis. After the hydrolysis, the organic layer was taken out, washed with an aqueous sodium hydroxide solution and water until the organic layer became neutral, and then concentrated. The resultant residue was purified by silica gel chromatography. Thus, compound B, which is a tetraphenylbenzidine derivative having formyl groups, was obtained in an amount of 4.6 g (yield, 83.0%).

Figure 7:
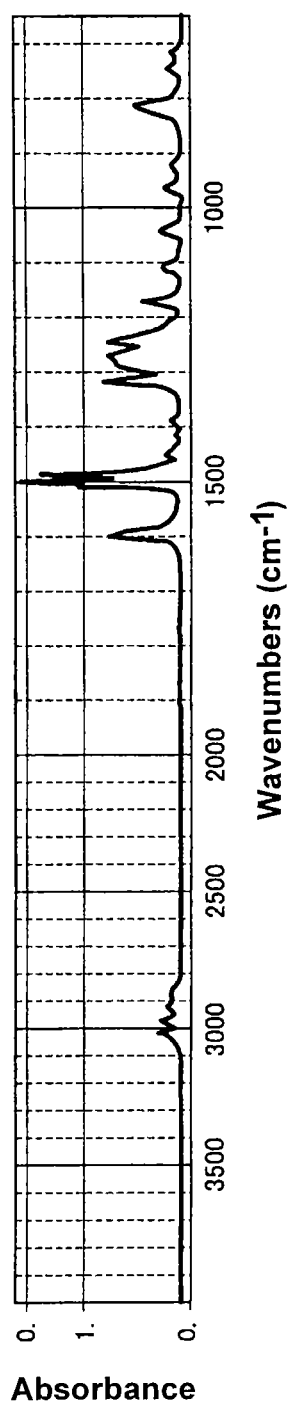
FIG. 7 is an IR chart of example compounds CT2-7 to CT2-9 obtained in Production Example 5.

To 100 mL of THF were added 4.6 g of the formyl compound B and 4.8 g of a positional-isomer mixture composed of compound C and compound D, which are phosphoric ester derivatives, (compound C/compound D=68/32). These compounds were dissolved in the THF. After the dissolution, 2.2 g of t-butoxypotassium was added thereto, and this mixture was stirred at room temperature for 30 minutes and reacted thereby. After completion of the reaction, the liquid reaction mixture was poured into water, and this mixture was extracted with toluene. Thereafter, the organic layer was concentrated, and the resultant residue was purified by silica gel chromatography. Thus, a positional-isomer mixture composed of charge transport substances CT2-7, CT2-8, and CT2-9, which were the target substances, was obtained in an amount of 5.4 g (yield, 83.1%). The composition of the positional-isomer mixture obtained was determined by examining the mixture by $^1$H-NMR (nuclear magnetic resonance) spectroscopy (composition: CT2-7/CT2-8/CT2-9=47/43/10). The IR chart obtained by examining the obtained positional-isomer mixture with "Protege 460", manufactured by Nicolet, is shown in FIG. 7.

Production Example 6: Positional-Isomer Mixture Composed of Example Compounds CT2-13, CT2-14, and CT2-15

A positional-isomer mixture composed of example compounds CT2-13, CT2-14, and CT2-15 was produced in accordance with the following scheme 3. Detailed conditions are shown below.

(Scheme 3)

[Chem. 26]

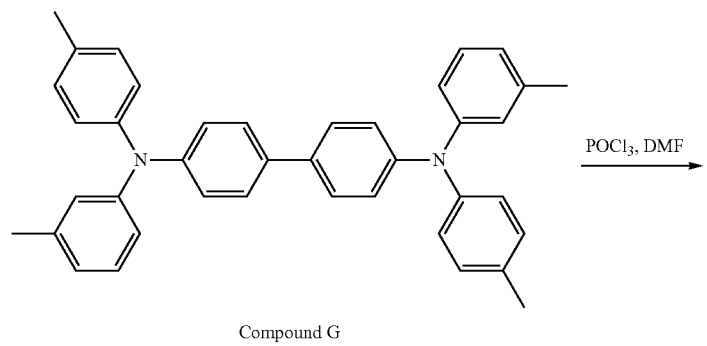

Compound G

-continued
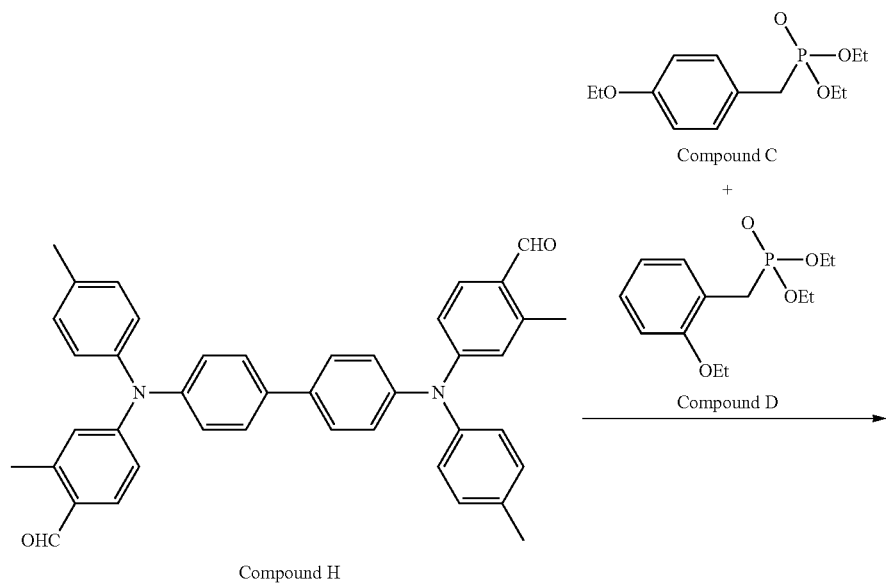
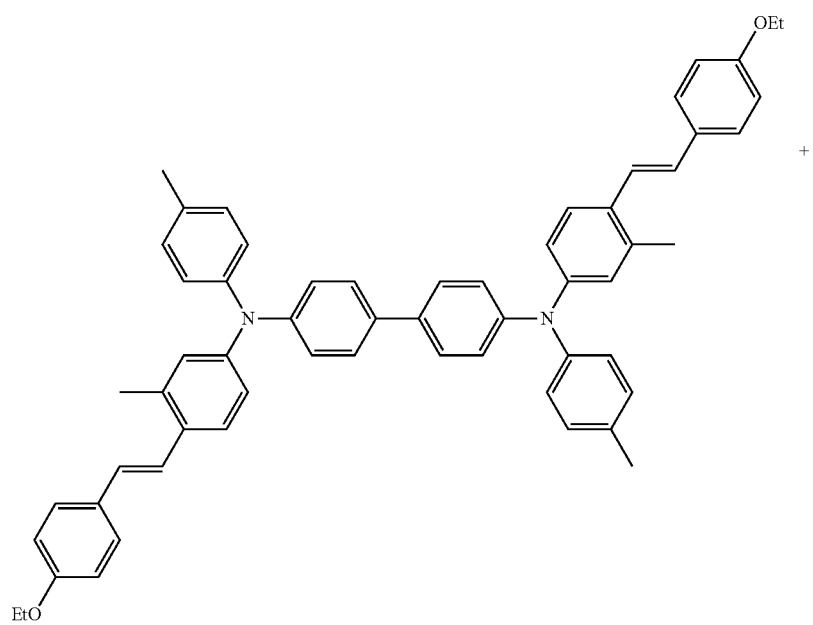
CT2-13

-continued

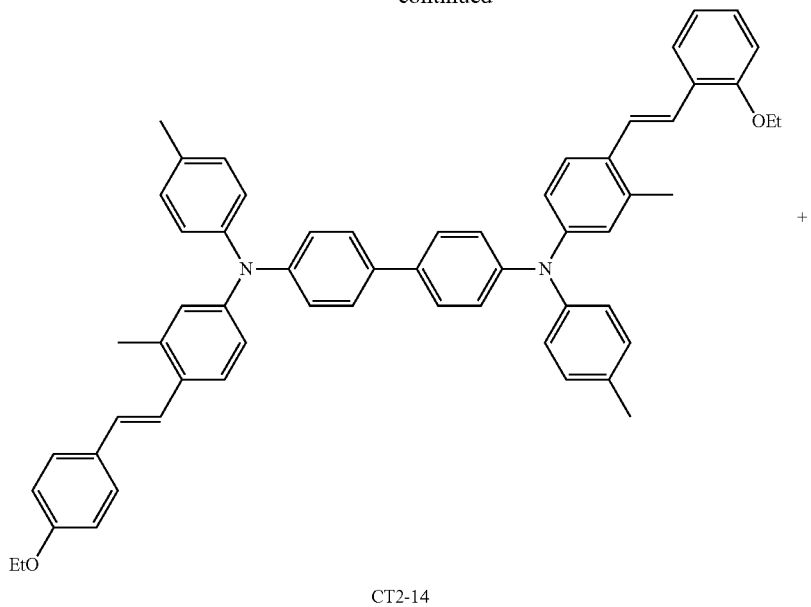

CT2-14

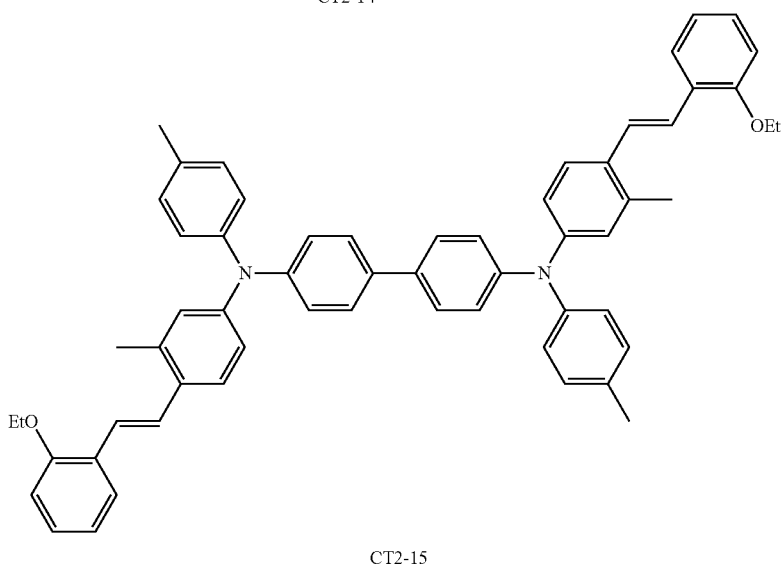

CT2-15

Ten grams of compound G, which is a tetraphenylbenzidine derivative, was added to 130 mL of DMF, and this mixture was heated to 60° C. After the heating, 20.7 g of phosphorus oxychloride was added dropwise thereto at 75° C. or lower. After completion of the dropwise addition, the resultant mixture was reacted for 12 hours at a temperature in the range of 70-75° C. After completion of the reaction, the liquid reaction mixture was cooled to room temperature and poured into a liquid mixture of 250 mL of water and 250 mL of toluene to conduct hydrolysis. After the hydrolysis, the organic layer was taken out, washed with an aqueous sodium hydroxide solution and water until the organic layer became neutral, and then concentrated. The resultant residue was purified by silica gel chromatography. Thus, compound H, which is a tetraphenylbenzidine derivative having formyl groups, was obtained in an amount of 8.5 g (yield, 77.0%).

Figure 8:
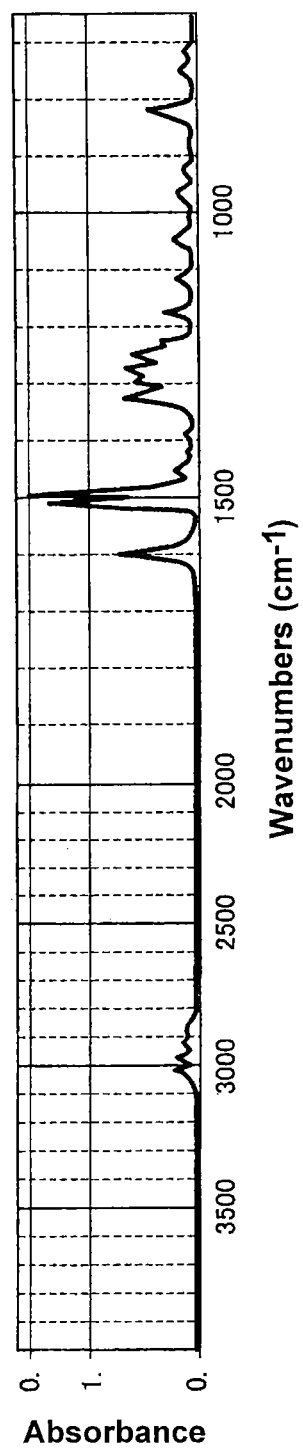
FIG. 8 is an IR chart of example compounds CT2-13 to CT2-15 obtained in Production Example 6.

To 100 mL of THF were added 4.5 g of the formyl compound H and 4.5 g of a positional-isomer mixture composed of compound C and compound D, which are phosphoric ester derivatives, (compound C/compound D=71/29). These compounds were dissolved in the THF. After the dissolution, 2.0 g of t-butoxypotassium was added thereto, and this mixture was stirred at room temperature for 30 minutes and reacted thereby. After completion of the reaction, the liquid reaction mixture was poured into water, and this mixture was extracted with toluene. Thereafter, the organic layer was concentrated, and the resultant residue was purified by silica gel chromatography. Thus, a positional-isomer mixture composed of charge transport substances CT2-13, CT2-14, and CT2-15, which were the target substances, was obtained in an amount of 5.5 g (yield, 87.7%). The composition of the positional-isomer mixture obtained was determined by examining the mixture by 1H-NMR (nuclear magnetic resonance) spectroscopy (composition: CT2-13/CT2-14/CT2-15=51/41/8). The IR chart obtained by examining the obtained positional-isomer mixture with "Protege 460", manufactured by Nicolet, is shown in FIG. 8.

<Production and Evaluation of Electrophotographic Photoreceptors Containing Charge Transport Substances According to First Aspect of the Invention>

Examples 1 to 8 and Comparative Examples 1 to 15: Evaluation of Electrophotographic Photoreceptors <Method for Producing Electrophotographic Photoreceptor>

A conductive support obtained by forming a vapor-deposited aluminum film (thickness, 70 nm) on a surface of a biaxially stretched poly(ethylene terephthalate) resin film (thickness, 75 μm) was used. The following dispersion for undercoat layer formation was applied to the vapor-deposited layer of the support with a bar coater in a thickness of 1.25 μm in terms of dry thickness, and the dispersion applied was dried to form an undercoat layer.

Rutile-form titanium oxide having an average primary-particle diameter of 40 nm ("TTO55N", manufactured by Ishihara Sangyo Kaisha, Ltd.) and 3% by mass, per 100% by mass the titanium oxide, of methyldimethoxysilane ("TSL 8117", manufactured by Toshiba Silicone Co., Ltd.) were introduced into a high-speed flow type mixing kneader ("SMG 300", manufactured by Kawata MFG. Co., Ltd.). The ingredients were mixed at a high rotational peripheral speed of 34.5 m/sec to obtain surface-treated titanium oxide. This surface-treated titanium oxide was dispersed in methanol/1-propanol with a ball mill to thereby obtain a dispersion slurry of the hydrophobized titanium oxide. This dispersion slurry and a methanol/1-propanol/toluene mixed solvent were stirred and mixed, with heating, together with pellets of a copolyamide having a composition in which the ε-caprolactam [compound represented by the following formula (A)]/bis(4-amino-3-methylcyclohexyl)methane [compound represented by the following formula (B)]/hexamethylenediamine [compound represented by the following formula (C)]/decamethylenedicarboxylic acid [compound represented by the following formula (D)]/octadecamethylenedicarboxylic acid [compound represented by the following formula (E)] molar ratio was 75%/9.5%/3%/9.5%/3%. After the polyamide pellets were dissolved, this mixture was subjected to an ultrasonic dispersion treatment. Thus, a dispersion for undercoat layer formation which had a methanol/1-propanol/toluene ratio of 7/1/2 by mass, contained the hydrophobized titanium oxide and the copolyamide in a mass ratio of 3/1, and had a solid concentration of 18.0% was obtained.

[Chem. 27]

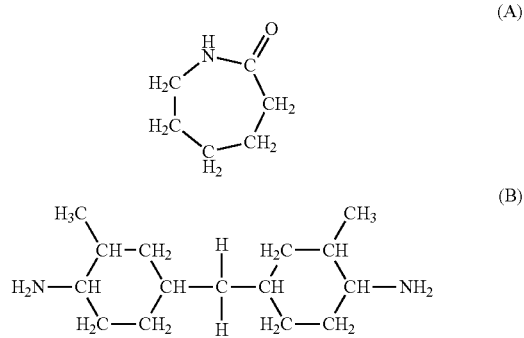

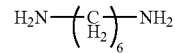

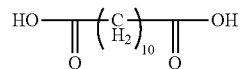

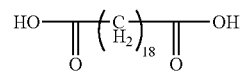

(Formation of Charge Generation Layer)

Figure 2:
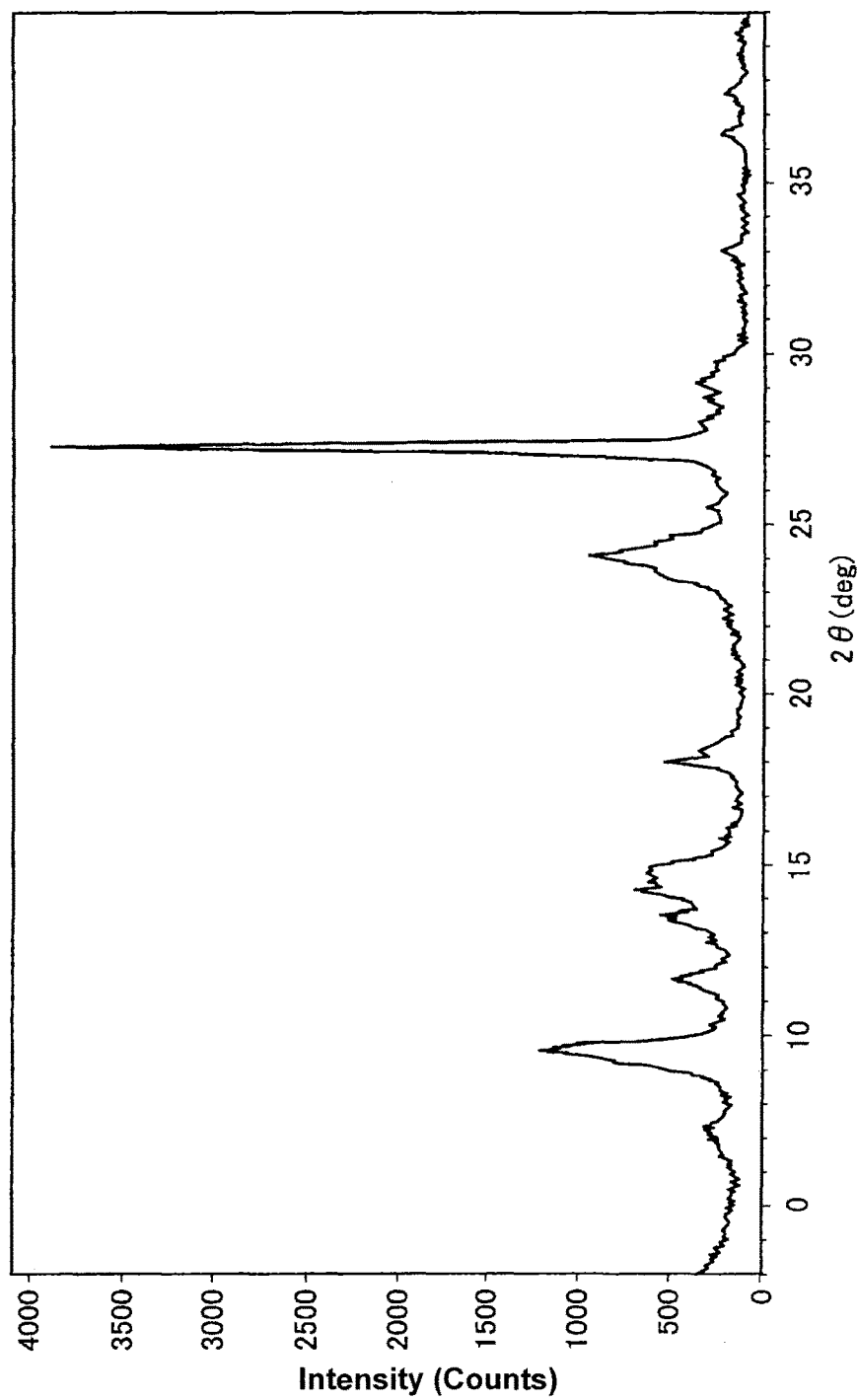
FIG. 2 is an X-ray diffraction pattern of the oxytitanium phthalocyanine used in the Examples.

As a charge generation substance were used oxytitanium phthalocyanine crystals (which, when examined with a CuKα characteristic X-ray line, gave an X-ray diffraction spectrum that showed a main diffraction peak at a Bragg angle (2θ±0.2°) of 27.2°, as shown in FIG. 2). The oxytitanium phthalocyanine crystals were used in an amount of 20 parts by mass and were mixed with 280 parts by mass of 1,2-dimethoxyethane. This mixture was subjected to a pulverization/dispersion treatment in which the crystals were pulverized with a grinding sand mill for 1 hour. Thus, a fine dispersion was obtained. Meanwhile, 10 parts by mass of poly(vinyl butyral) (trade name "Denka Butyral" #6000C, manufactured by Denki Kagaku Kogyo K.K.) was dissolved in 253 parts by mass of 1,2-dimethoxyethane and 85 parts by mass of 4-methoxy-4-methyl-2-pentanone to prepare a binder solution.

The fine dispersion obtained by the pulverization/dispersion treatment described above was mixed with the binder solution and 230 parts by mass of 1,2-dimethoxyethane to prepare a coating fluid for charge generation layer formation. This coating fluid for charge generation layer formation was applied on the undercoat layer of the conductive support with a bar coater in a thickness of 0.4 μm in terms of dry thickness, and the coating fluid applied was dried to form a charge generation layer.

(Formation of Charge Transport Layer)

As a binder resin was used a polycarbonate resin (Mv=30, 500) that was made up of 51% by mole repeating units (units represented by the following formula (PA)) for which 2,2-bis(4-hydroxy-3-methylphenyl)propane had been used as the aromatic diol ingredient and 49% by mole repeating units (units represented by the following formula (PB)) for which 1,1-bis(4-hydroxyphenyl)-1-phenylethane had been used as the aromatic diol ingredient, as shown below, and that had an end structure derived from p-t-butylphenol. Fifty parts by mass of the charge transport substance described below in detail, 100 parts by mass of the binder resin, 8 parts by mass of the antioxidant having the structure of the following formula (AOX1), and 0.03 parts by mass of a silicone oil as a leveling agent were dissolved in 640 parts by mass of a tetrahydrofuran/toluene (mass ratio, 8/2) mixed solvent to prepare a coating fluid for charge transport layer formation.

[Chem. 28]

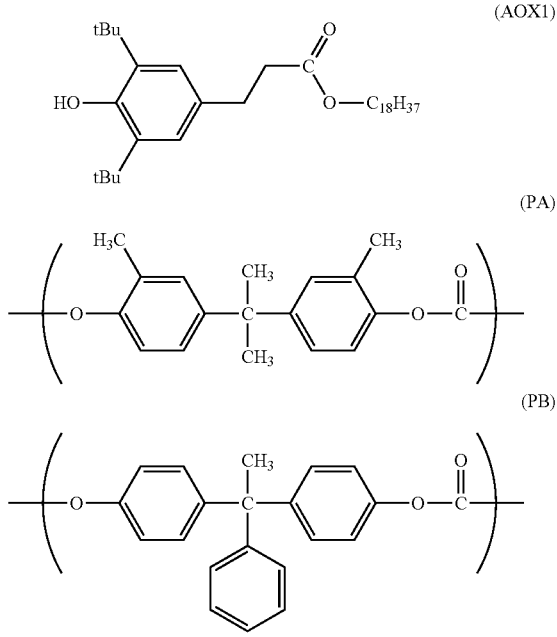

(AOX1)

(PA)

(PB)

The coating fluid for charge transport layer formation thus obtained was applied on the charge generation layer in a thickness of 25 μm in terms of dry thickness. Thus, an electrophotographic photoreceptor having a multilayer type photosensitive layer was obtained.

Through the steps described above, electrophotographic photoreceptors of Examples 1 to 4 and Comparative Examples 1 to 9 (photoreceptor numbers: photoreceptors A to D and photoreceptors RA to RI), which had a multilayer type photosensitive layer, were each produced. In each of Comparative Examples 7 to 9, however, the charge transport substance had not dissolved completely in the stage of preparing the coating fluid for charge transport layer formation and, hence, an even charge transport layer was unable to be formed and a photoreceptor was unable to be produced. Details of the charge transport substance used in each electrophotographic photoreceptor are as follows.

Photoreceptor A (Example 1)

The CT1-8 produced in Production Example 1 was used as a charge transport substance.

[Chem. 29]

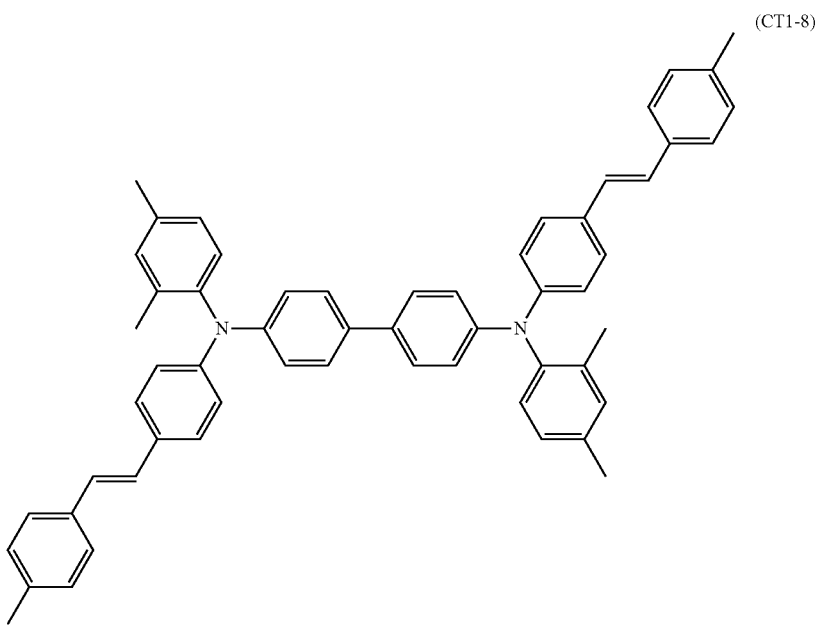

(CT1-8)

Photoreceptor B (Example 2)
The positional-isomer mixture composed of CT1-10, CT1-11, and CT1-12 which was produced in Production Example 2 was used as a charge transport substance. (Composition of the positional-isomer mixture: CT-10/CT1-11/CT1-12=54/39/7)
[Chem. 30]
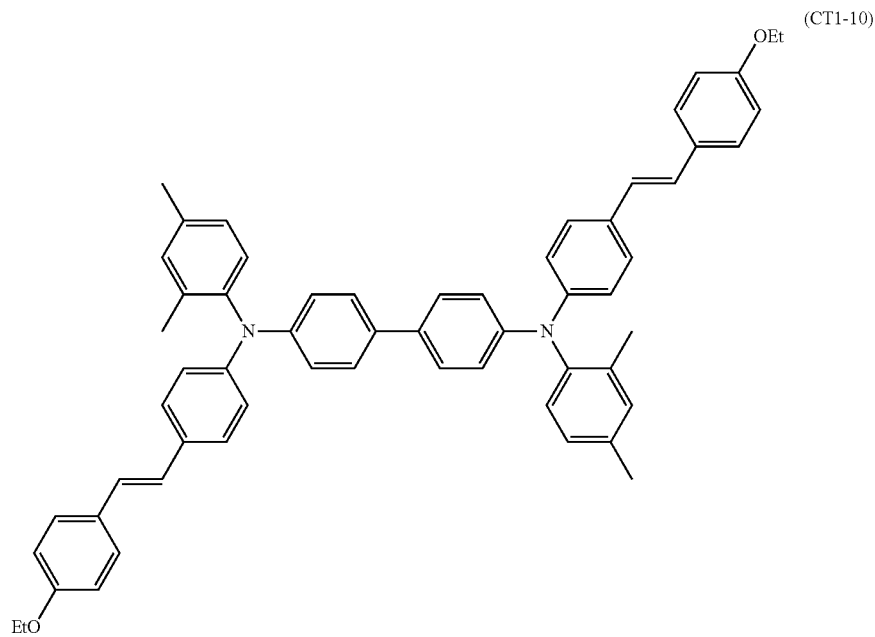
(CT1-10)
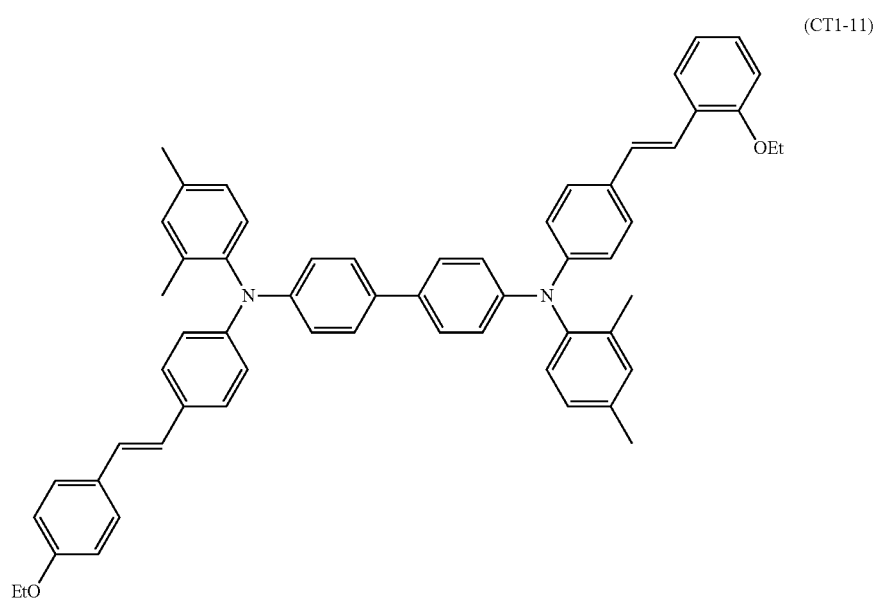
(CT1-11)

-continued
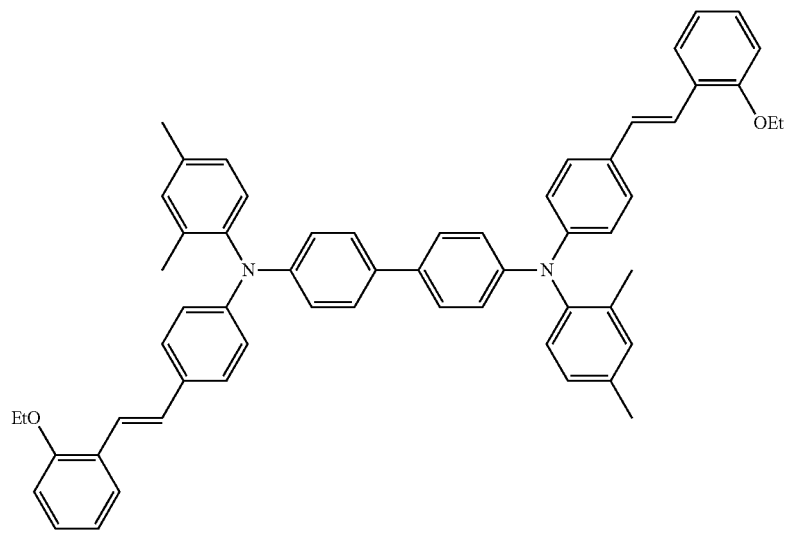
(CT1-12)
Photoreceptor C (Example 3)
The CT1-7 produced in Production Example 3 was used as a charge transport substance.
[Chem. 31]
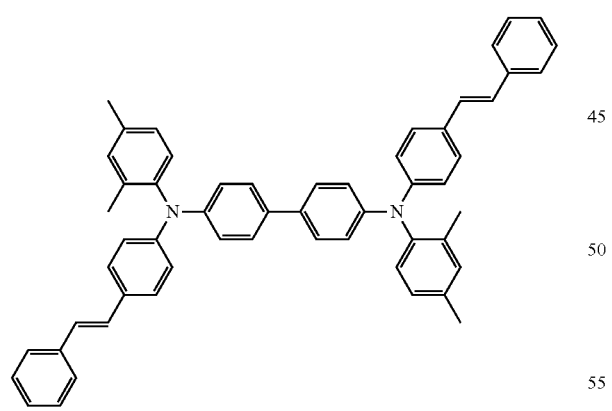
(CT1-7)
Photoreceptor D (Example 4)
The CT1-37 produced in Production Example 4 was used as a charge transport substance.

[Chem. 32]

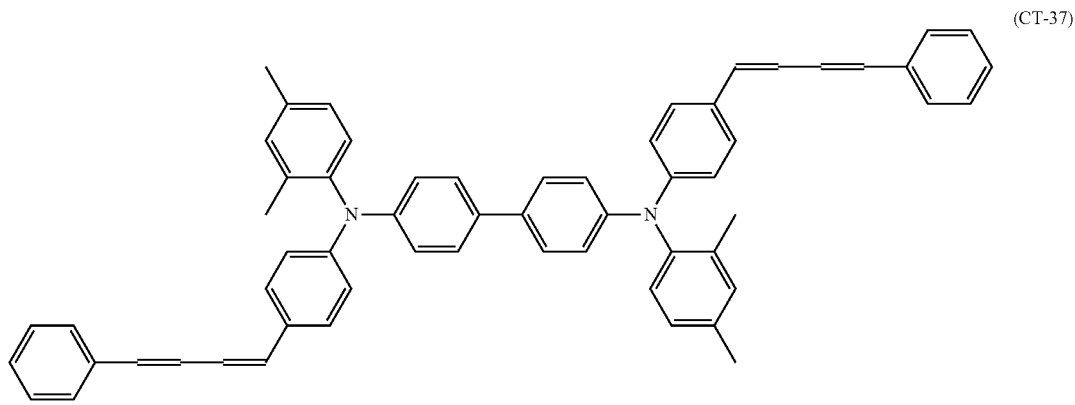

(CT-37)

Photoreceptor RA (Comparative Example 1)

The charge transport substance of the following structural formula (RC1) was used. (Synthesized on the basis of the Example 1 of JP-A-2006-8670)

[Chem. 33]

[Chem. 34]

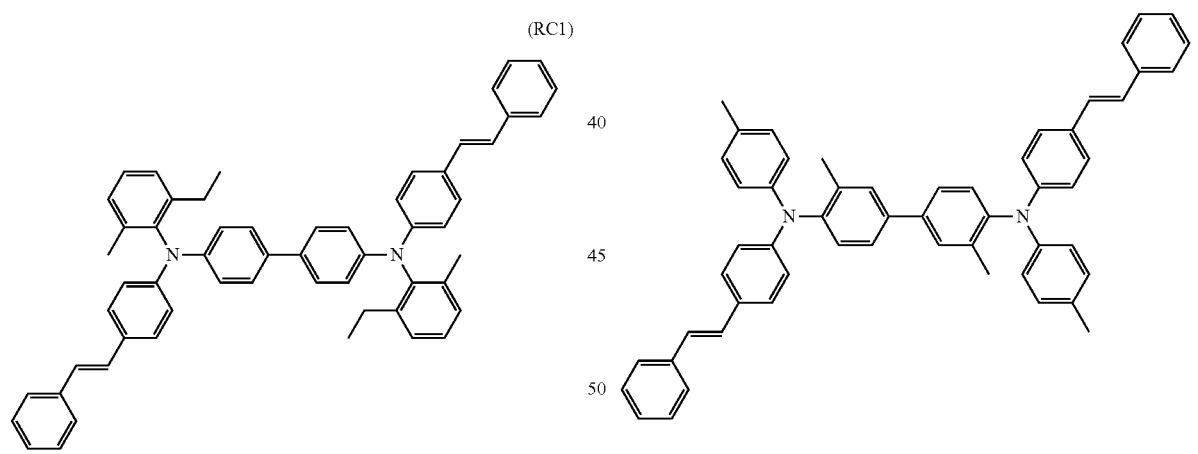

Photoreceptor RB (Comparative Example 2)

The charge transport substance of the following structural formula (RC2) was used. (Synthesized on the basis of the Production Example 1 of JP-A-7-36203)

Photoreceptor RC (Comparative Example 3)

The charge transport substance of the following structural formula (RC3) was used. (Synthesized on the basis of the Example 1 of JP-A-2002-80432)

[Chem. 35]

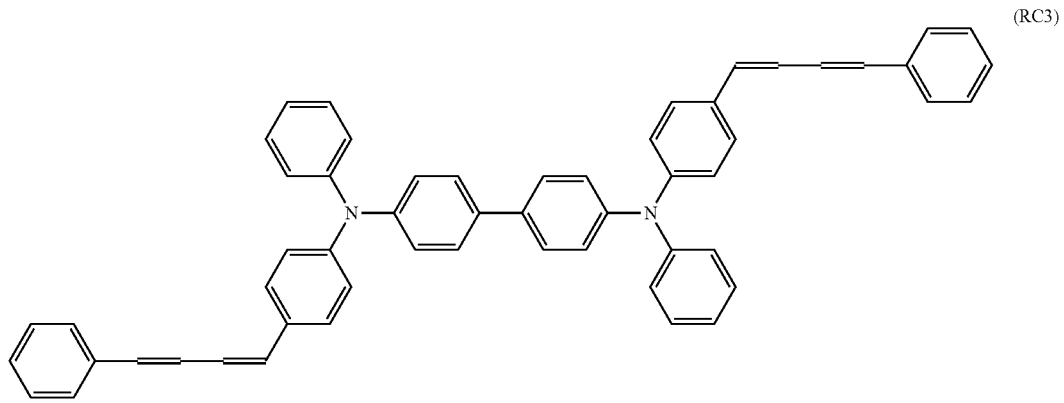
(RC3)

Photoreceptor RD (Comparative Example 4)

The charge transport substance of the following structural formula (RC4) was used.

[Chem. 36]

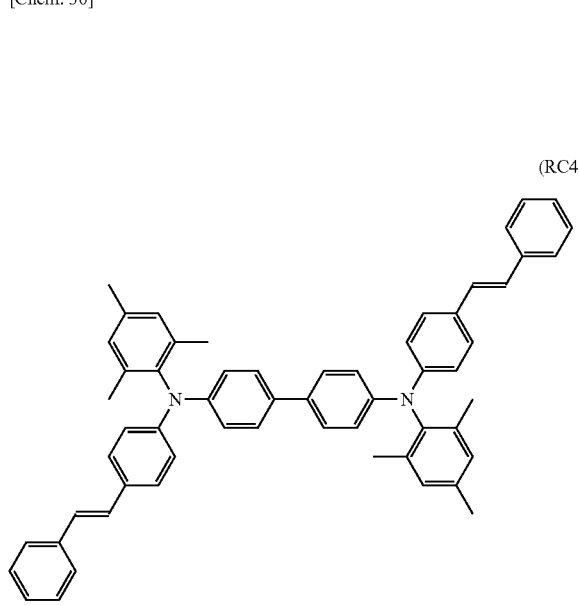
(RC4)

Photoreceptor RE (Comparative Example 5)

The charge transport substance of the following structural formula (RC5) was used. (Synthesized on the basis of the Synthesis Example 4 of JP-A-2008-83105)

[Chem. 37]

(RC5)

Photoreceptor RF (Comparative Example 6)

The charge transport substance of the following structural formula (RC6) was used.

[Chem. 38]

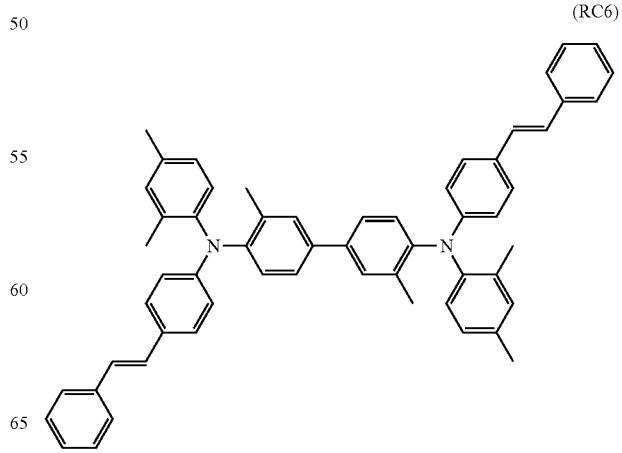
(RC6)

Photoreceptor RG (Comparative Example 7)

The charge transport substance of the following structural formula (RC7) was used.

[Chem. 39]

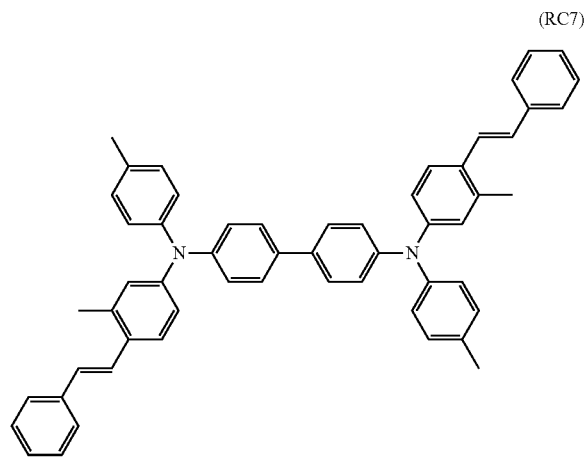
(RC7)

[Chem. 41]

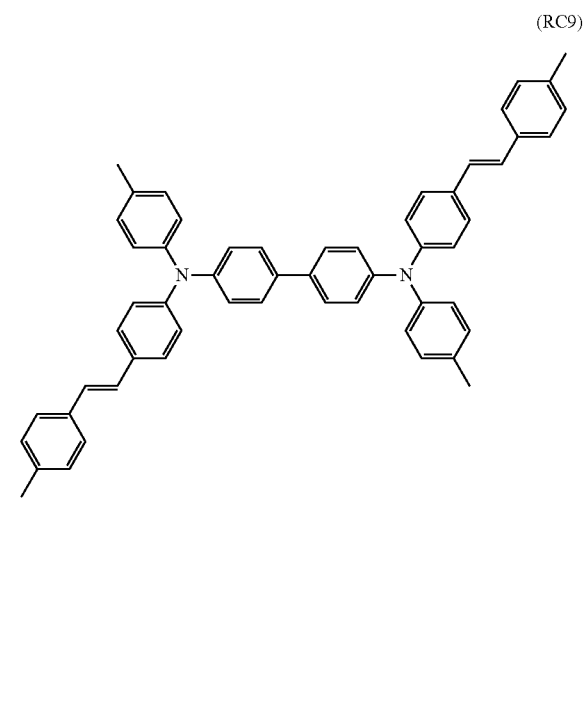
(RC9)

Photoreceptor RH (Comparative Example 8)

The charge transport substance of the following structural formula (RC8) was used.

[Chem. 40]

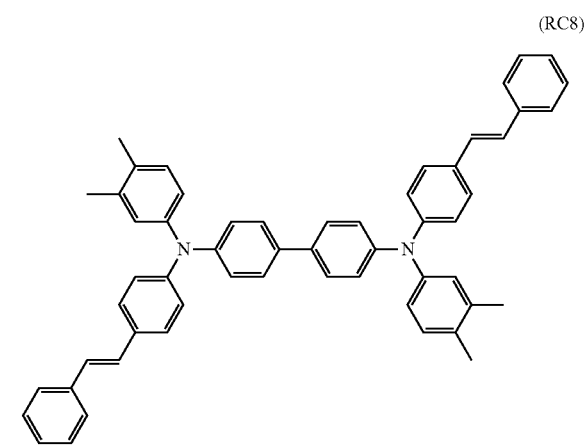
(RC8)

Photoreceptor RI (Comparative Example 9)

The charge transport substance of the following structural formula (RC9) was used.

<Evaluation of Electrophotographic Photoreceptors>

The electrophotographic photoreceptors of Examples 1 to 4 and Comparative Examples 1 to 6 were each mounted on an apparatus for electrophotographic-property evaluation produced in accordance with the standards of The Society of Electrophotography of Japan (described in The Society of Electrophotography of Japan, ed., *Zoku Denshi Shashin Gijutsu No Kiso To Ōyō*, Corona Publishing Co., Ltd., pp. 404-405), and a cycle composed of charging, exposure, potential measurement, and erase was conducted in the following manner to thereby evaluate the electrical properties thereof.

Under the conditions of a temperature of 25° C. and a humidity of 50%, the photoreceptor was charged to an initial surface potential of −700 V, and 780-nm monochromatic light obtained by passing the light of a halogen lamp through an interference filter was irradiated upon the photoreceptor. The irradiation energy required for the surface potential to become −350 V (half-decay exposure energy) was measured as sensitivity (unit: µJ/cm$^2$). Furthermore, each photoreceptor was charged to an initial surface potential of −700 V and subsequently exposed to light at an irradiation energy of 0.6 µJ/cm$^2$, and the resultant surface potential (unit: −V) was measured and taken as residual potential. Moreover, each photoreceptor charged to an initial surface potential of −700 V was allowed to stand in the dark for 5 seconds, and then examined for surface potential; the difference between these surface potential values was taken as dark decay (unit: V).

The results of the measurements are shown in Table 1.

TABLE 1

|  |  | Charge transport substance | Sensitivity ($\mu J/cm^2$) | Residual potential (−V) | Dark decay (V) |
|---|---|---|---|---|---|
| Example 1 | photoreceptor A | CT1-8 | 0.076 | 5 | 22 |
| Example 2 | photoreceptor B | CT1-10, 11, 12 | 0.077 | 9 | 18 |
| Example 3 | photoreceptor C | CT1-7 | 0.078 | 22 | 14 |
| Example 4 | photoreceptor D | CT1-37 | 0.076 | 24 | 14 |
| Comparative Example 1 | photoreceptor RA | RC1 | 0.078 | 46 | 20 |
| Comparative Example 2 | photoreceptor RB | RC2 | 0.079 | 38 | 21 |
| Comparative Example 3 | photoreceptor RC | RC3 | 0.079 | 33 | 17 |
| Comparative Example 4 | photoreceptor RD | RC4 | 0.078 | 43 | 15 |
| Comparative Example 5 | photoreceptor RE | RC5 | 0.078 | 23 | 20 |
| Comparative Example 6 | photoreceptor RF | RC6 | 0.076 | 32 | 22 |
| Comparative Example 7 | photoreceptor RG | RC7 | charge transport layer was unable to be formed due to poor solubility of the charge transport substance | | |
| Comparative Example 8 | photoreceptor RH | RC8 | charge transport layer was unable to be formed due to poor solubility of the charge transport substance | | |
| Comparative Example 9 | photoreceptor RI | RC9 | charge transport layer was unable to be formed due to poor solubility of the charge transport substance | | |

<Evaluation of Ozone Resistance>

A method for ozone exposure test is shown below. EPA 8200, manufactured by Kawaguchi Electric Co., Ltd., was used, and the photoreceptors obtained in Example 3 and Comparative Example 5 were each charged by causing a current of 25 µA to flow through the corotron charging device. The value of charge of each photoreceptor in this state was expressed by V1. Thereafter, these photoreceptors were exposed to ozone with a concentration of 150-200 ppm for 3-5 hours per day over a period of 2 days, and the photoreceptors were each similarly examined for the value of charge; this value was expressed by V2. In Table 2 is shown the retention of charge (V2/V1×100) (%) through the ozone exposure.

TABLE 2

|  |  | Charge transport substance | Retention of charge (%) |
|---|---|---|---|
| Example 3 | photoreceptor C | CT1-7 | 98% |
| Comparative Example 5 | photoreceptor RE | RC5 | 85% |

It can be seen from the results given in Table 1 and Table 2 that the charge transport substances according to the first aspect of the invention have high solubility in the coating-fluid solvent used for charge transport layer formation and show satisfactory film-forming properties, and that when the charge transport substances which are within the scope of the invention are used, it is possible to provide high-performance photoreceptors which have high sensitivity, show a low residual potential, and have higher resistance to ozone exposure as compared with the known photoreceptor showing the same residual potential.

Electrophotographic photoreceptors of Examples 5 to 8 and Comparative Examples 10 to 15 (photoreceptor numbers: photoreceptors E to H and photoreceptors RJ to RO), which had a multilayer type photosensitive layer, were each produced through the same steps as for photoreceptor A, except for the following modifications.

Photoreceptor E (Example 5)

The same procedure as in Example 1 was conducted, except that the binder resin of the coating fluid for charge transport layer formation shown above in <Method for Producing Electrophotographic Photoreceptor> was replaced with the polyarylate resin (Mv=40,500) having the following structural formula (PC). Thus, photoreceptor E was produced.

[Chem. 42]

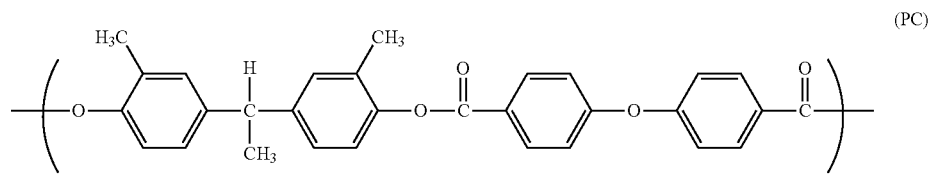

(PC)

Photoreceptor F (Example 6)

The same procedure as in Example 2 was conducted, except that the binder resin of the coating fluid for charge transport layer formation shown above in <Method for Producing Electrophotographic Photoreceptor> was replaced with the polyarylate resin (Mv=40,500) having the structural formula (PC). Thus, photoreceptor F was produced.

Photoreceptor G (Example 7)

The same procedure as in Example 3 was conducted, except that the binder resin of the coating fluid for charge transport layer formation shown above in <Method for Producing Electrophotographic Photoreceptor> was replaced with the polyarylate resin (Mv=40,500) having the structural formula (PC). Thus, photoreceptor G was produced.

Photoreceptor H (Example 8)

The same procedure as in Example 4 was conducted, except that the binder resin of the coating fluid for charge transport layer formation shown above in <Method for Producing Electrophotographic Photoreceptor> was replaced with the polyarylate resin (Mv=40,500) having the structural formula (PC). Thus, photoreceptor H was produced.

Photoreceptor RJ (Comparative Example 10)

The same procedure as in Comparative Example 1 was conducted, except that the binder resin of the coating fluid for charge transport layer formation shown above in <Method for Producing Electrophotographic Photoreceptor> was replaced with the polyarylate resin (Mv=40,500) having the structural formula (PC). Thus, photoreceptor RJ was produced.

Photoreceptor RK (Comparative Example 11)

The same procedure as in Comparative Example 2 was conducted, except that the binder resin of the coating fluid for charge transport layer formation shown above in <Method for Producing Electrophotographic Photoreceptor> was replaced with the polyarylate resin (Mv=40,500) having the structural formula (PC). Thus, photoreceptor RK was produced.

Photoreceptor RL (Comparative Example 12)

The same procedure as in Comparative Example 3 was conducted, except that the binder resin of the coating fluid for charge transport layer formation shown above in <Method for Producing Electrophotographic Photoreceptor> was replaced with the polyarylate resin (Mv=40,500) having the structural formula (PC). Thus, photoreceptor RL was produced.

Photoreceptor RM (Comparative Example 13)

The same procedure as in Comparative Example 4 was conducted, except that the binder resin of the coating fluid for charge transport layer formation shown above in <Method for Producing Electrophotographic Photoreceptor> was replaced with the polyarylate resin (Mv=40,500) having the structural formula (PC). Thus, photoreceptor RM was produced.

Photoreceptor RN (Comparative Example 14)

The same procedure as in Comparative Example 4 was conducted, except that the binder resin of the coating fluid for charge transport layer formation shown above in <Method for Producing Electrophotographic Photoreceptor> was replaced with the polyarylate resin (Mv=40,500) having the structural formula (PC). Thus, photoreceptor RN was produced.

Photoreceptor RO (Comparative Example 15)

The same procedure as in <Method for Producing Electrophotographic Photoreceptor> was conducted, except that when the coating fluid for charge transport layer formation in <Method for Producing Electrophotographic Photoreceptor> was produced, the compound of the following formula (RC10) was used as a charge transport substance and the binder resin was replaced with the polyarylate resin (Mv=40,500) having structural formula (PC). Thus, photoreceptor RO was produced.

[Chem. 43]

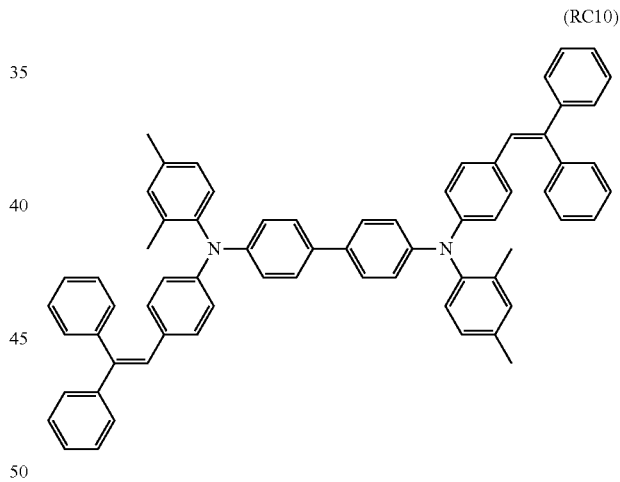

(RC10)

The electrophotographic photoreceptors of Examples 5 to 8 and Comparative Examples 10 to 15 were evaluated in accordance with <Evaluation of Electrophotographic Photoreceptors>. The results thereof are shown in Table 3.

TABLE 3

| | | Charge transport substance | Sensitivity ($\mu J/cm^2$) | Residual potential (-V) | Dark decay (V) |
|---|---|---|---|---|---|
| Example 5 | photoreceptor E | CT1-8 | 0.088 | 38 | 27 |
| Example 6 | photoreceptor F | CT1-10, 11, 12 | 0.091 | 29 | 25 |
| Example 7 | photoreceptor G | CT1-7 | 0.09 | 65 | 22 |

TABLE 3-continued

|  |  | Charge transport substance | Sensitivity (μJ/cm²) | Residual potential (-V) | Dark decay (V) |
|---|---|---|---|---|---|
| Example 8 | photoreceptor H | CT1-37 | 0.091 | 59 | 19 |
| Comparative Example 10 | photoreceptor RJ | RC1 | 0.094 | 114 | 32 |
| Comparative Example 11 | photoreceptor RK | RC2 | 0.093 | 171 | 34 |
| Comparative Example 12 | photoreceptor RL | RC3 | 0.096 | 117 | 33 |
| Comparative Example 13 | photoreceptor RM | RC4 | 0.089 | 78 | 28 |
| Comparative Example 14 | photoreceptor RN | RC6 | 0.092 | 158 | 36 |
| Comparative Example 15 | photoreceptor RO | RC10 | 0.084 | 76 | 25 |

It has become obvious from the results given in Table 3 that when the charge transport substances according to the first aspect of the invention are used, it is possible to provide high-performance photoreceptors which have high sensitivity and show a low residual potential, irrespective of the binder resin used in the charge transport layers.

<Production and Evaluation of Electrophotographic Photoreceptors Containing Charge Transport Substances According to Second Aspect of the Invention>

Examples 9 to 14 and Comparative Examples 16 to 26: Evaluation of Electrophotographic Photoreceptors <Method for Producing Electrophotographic Photoreceptors>

Electrophotographic photoreceptors of Examples 9 to 11 and Comparative Examples 16 to 22 (photoreceptor numbers: photoreceptors I to K and photoreceptors QA to QG), which had a multilayer type photosensitive layer, were each produced through the same steps as in the production of the electrophotographic photoreceptors containing charge transport substances according to the first aspect of the invention. In each of Comparative Examples 20 to 22, however, the charge transport substance had not dissolved completely in the stage of preparing the coating fluid for charge transport layer formation and, hence, a photoreceptor was unable to be produced. Details of the charge transport substance used in each electrophotographic photoreceptor are as follows.

Photoreceptor I (Example 9)

A mixture of positional isomers of the following structural formulae (CT2-7) to (CT2-9) was used as a charge transport substance. (Composition of the positional-isomer mixture: CT2-7/CT2-8/CT2-9=47/43/10)

[Chem. 44]

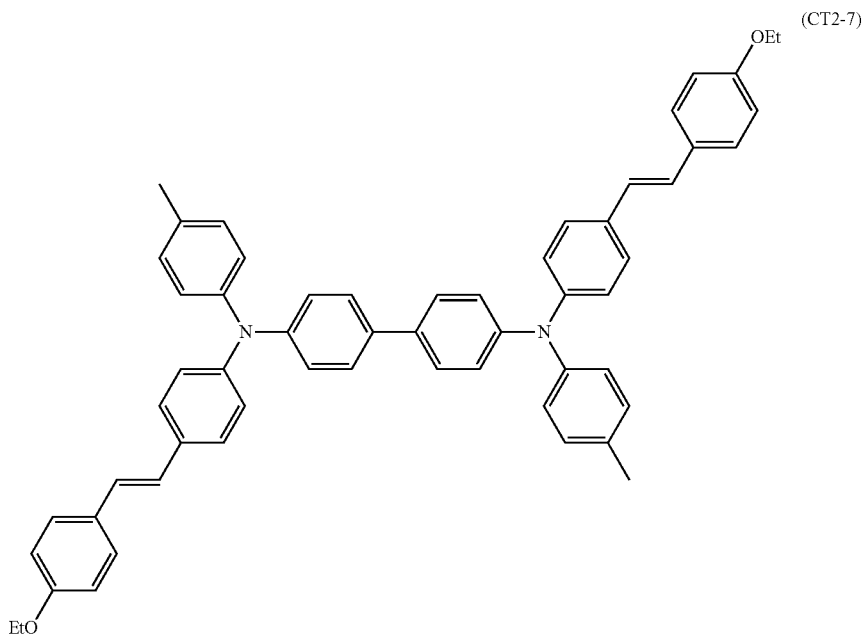

(CT2-7)

(CT2-8)
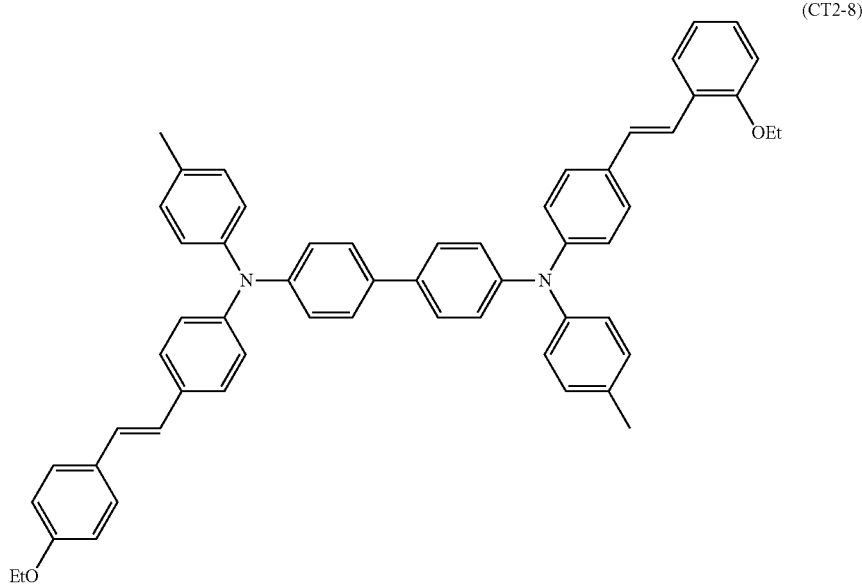
(CT2-9)
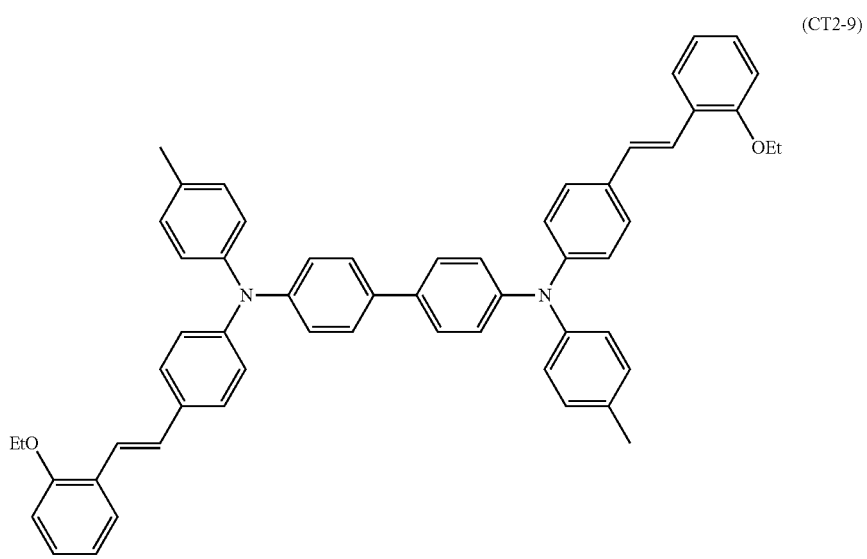
Photoreceptor J (Example 10)
A mixture of positional isomers of the following structural formulae (CT2-10) to (CT2-12) was used as a charge transport substance. (Composition of the positional-isomer mixture: CT2-10/CT2-11/CT2-12=54/39/7)

[Chem. 45]
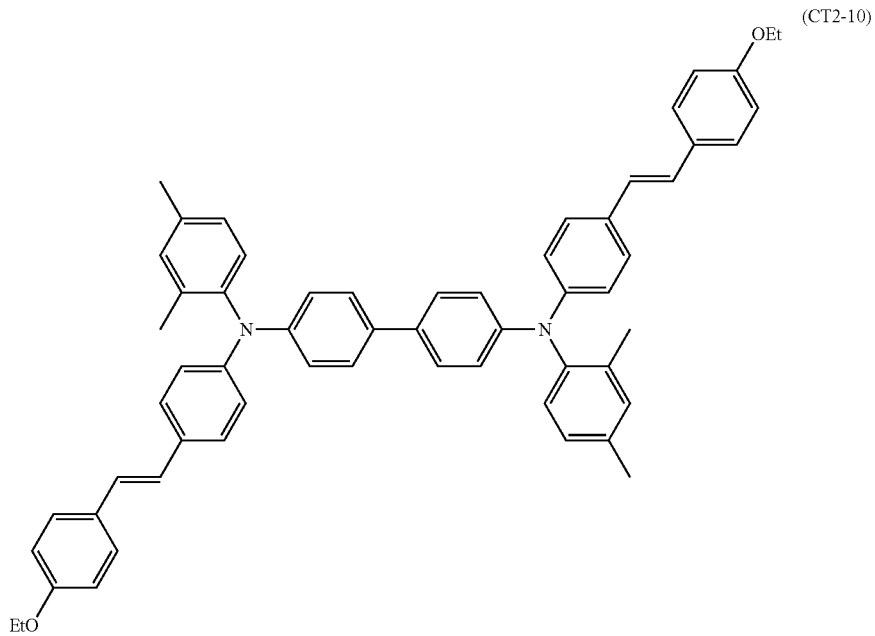
(CT2-10)
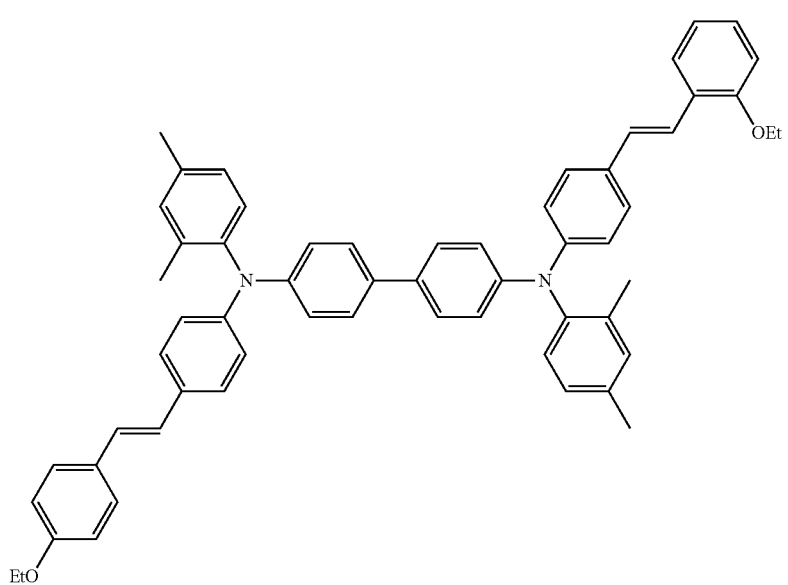
(CT2-11)

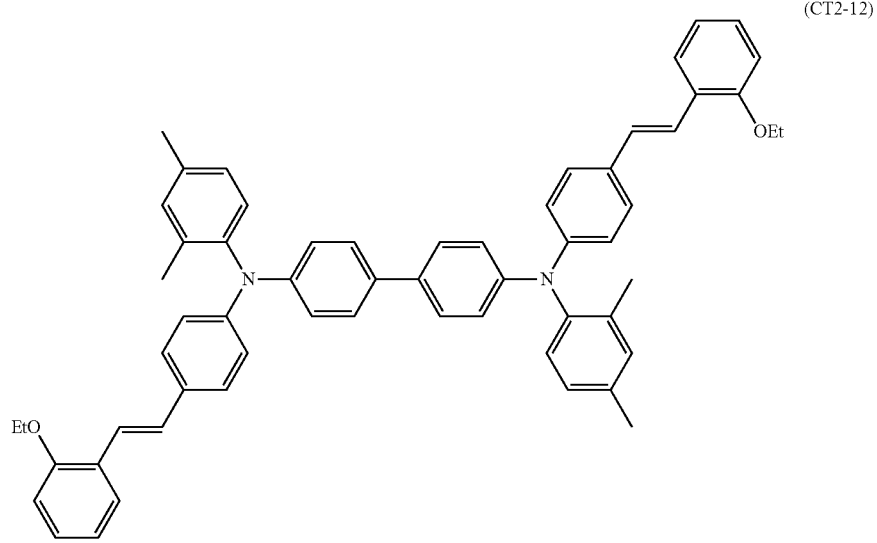 [SMILES: CCOc1ccccc1/C=C/c1ccc(N(c2ccc(-c3ccc(N(c4ccc(/C=C/c5ccccc5OCC)cc4)c4ccc(C)cc4C)cc3)cc2)c2ccc(C)cc2C)cc1]
(CT2-12)
Photoreceptor K (Example 11)
A mixture of positional isomers of the following structural formulae (CT2-13) to (CT2-15) was used as a charge transport substance. (Composition of the positional-isomer mixture: CT2-13/CT2-14/CT2-15=51/41/8)
[Chem. 46]
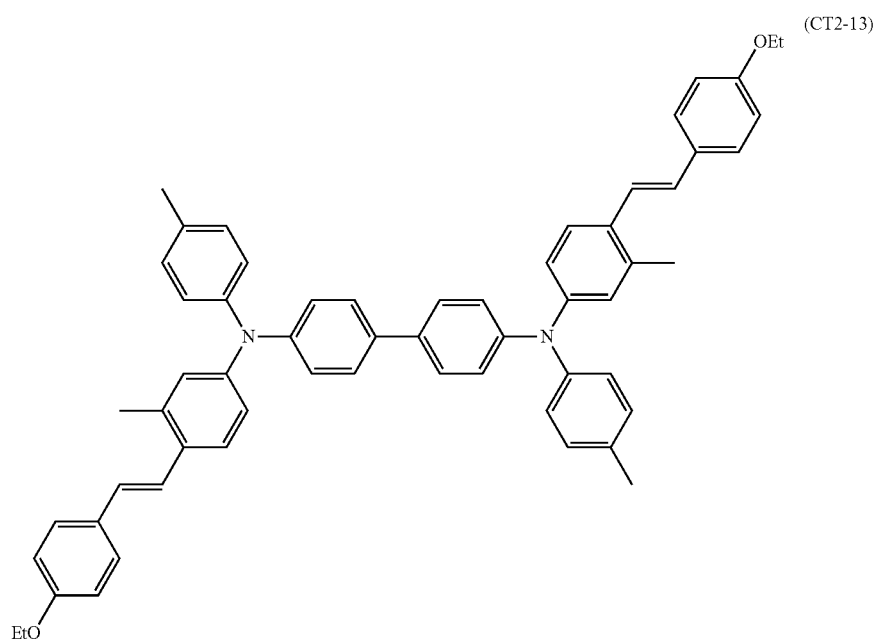
(CT2-13)

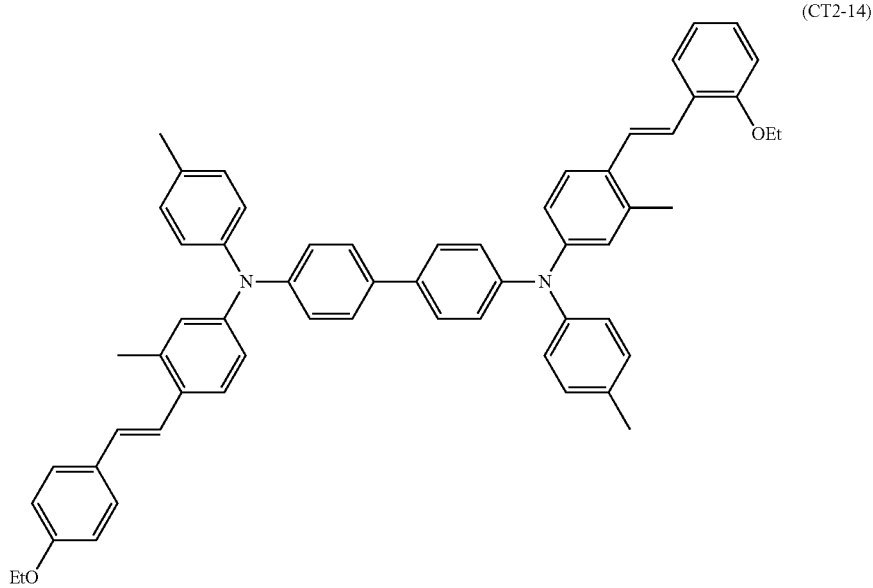
(CT2-14)
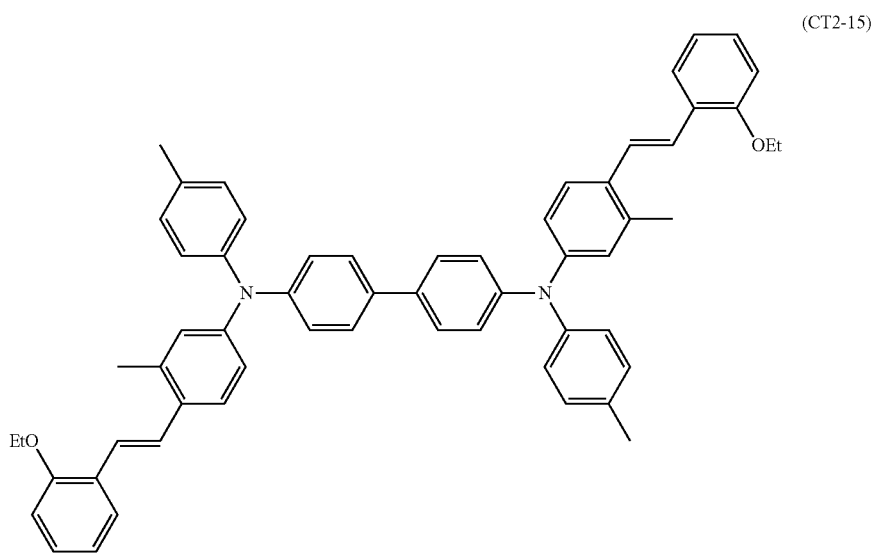 [SMILES: CCOc1ccccc1/C=C/c1ccc(N(c2ccc(C)cc2)c2ccc(-c3ccc(N(c4ccc(C)cc4)c4ccc(/C=C/c5ccccc5OCC)c(C)c4)cc3)cc2)cc1C]
(CT2-15)

Photoreceptor QA (Comparative Example 16)

The charge transport substance of the following structural formula (D) was used. (Synthesized on the basis of the Example 1 of JP-A-2006-8670)

[Chem. 47]

[Chem. 48]

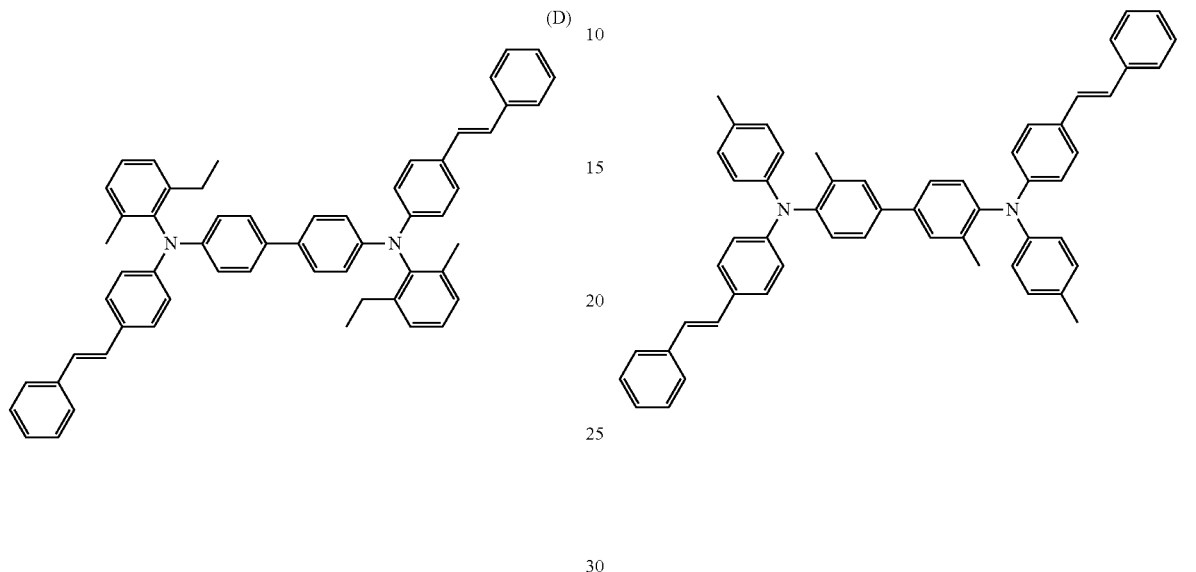

Photoreceptor QB (Comparative Example 17)

The charge transport substance of the following structural formula (E) was used. (Synthesized on the basis of the Production Example 1 of JP-A-7-36203)

Photoreceptor QC (Comparative Example 18)

The charge transport substance of the following structural formula (F) was used. (Synthesized on the basis of the Example 1 of JP-A-2002-80432)

[Chem. 49]

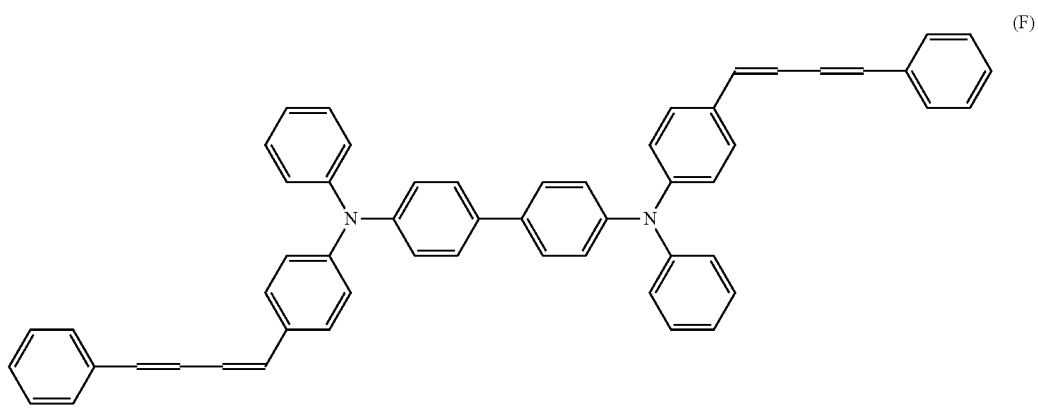

Photoreceptor QD (Comparative Example 19)

The charge transport substance of the following structural formula (G) was used. (Synthesized on the basis of the Synthesis Example 4 of JP-A-2008-83105)

[Chem. 50]

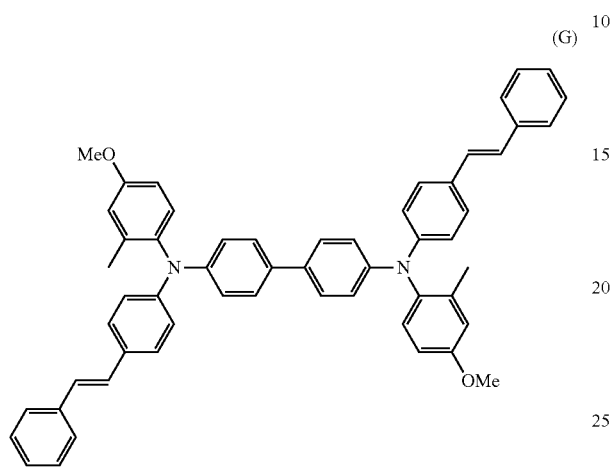

(G)

Photoreceptor QE (Comparative Example 20)

The charge transport substance of the following structural formula (H) was used.

[Chem. 51]

(H)

Photoreceptor QF (Comparative Example 21)

The charge transport substance of the following structural formula (1) was used.

[Chem. 52]

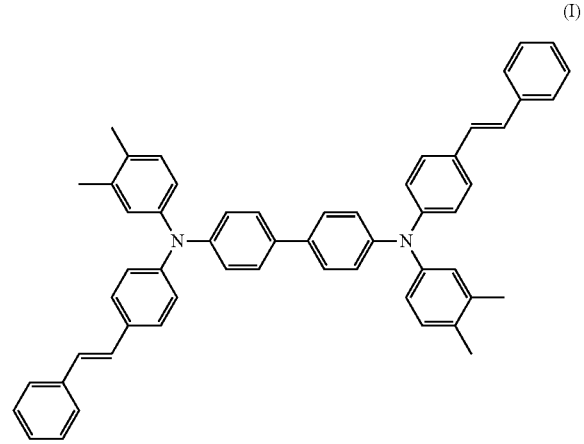

(I)

Photoreceptor QG (Comparative Example 22)

The charge transport substance of the following structural formula (J) was used.

[Chem. 53]

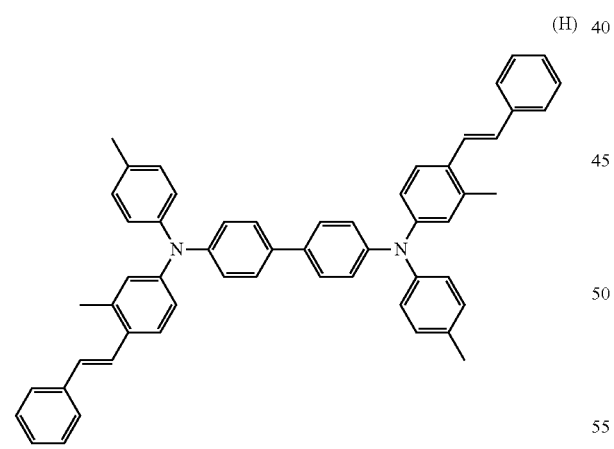

(J)

<Evaluation of Electrophotographic Photoreceptors>

The electrophotographic photoreceptors of Examples 9 to 11 and Comparative Examples 16 to 19 were each mounted on an apparatus for electrophotographic-property evaluation produced in accordance with the standards of The Society of Electrophotography of Japan (described in The Society of Electrophotography of Japan, ed., *Zoku Denshi Shashin Gijutsu No Kiso To Ōyō*, Corona Publishing Co., Ltd., pp. 404-405), and a cycle composed of charging, exposure, potential measurement, and erase was conducted in the following manner to thereby evaluate the electrical properties thereof.

Under the conditions of a temperature of 25° C. and a humidity of 50%, the photoreceptor was charged to an initial surface potential of −700 V, and 780-nm monochromatic light obtained by passing the light of a halogen lamp through an interference filter was irradiated upon the photoreceptor. The irradiation energy required for the surface potential to become −350 V (half-decay exposure energy) was measured as sensitivity (unit: µJ/cm$^2$). Furthermore, each photoreceptor was charged to an initial surface potential of −700 V and subsequently exposed to light at an irradiation energy of 0.6 μJ/cm², and the resultant surface potential (unit: −V) was measured and taken as residual potential. Moreover, each photoreceptor charged to an initial surface potential of −700 V was allowed to stand in the dark for 5 seconds, and then examined for surface potential; the difference between these surface potential values was taken as dark decay (unit: V).

The results of the measurements are shown in Table 4.

TABLE 4

| | | Charge transport substance | Sensitivity (μJ/cm²) | Residual potential (−V) | Dark decay (V) |
|---|---|---|---|---|---|
| Example 9 | photoreceptor I | CT2-7 to 9 | 0.081 | 13 | 18 |
| Example 10 | photoreceptor J | CT2-10 to 12 | 0.077 | 9 | 18 |
| Example 11 | photoreceptor K | CT2-13 to 15 | 0.081 | 13 | 16 |
| Comparative Example 16 | photoreceptor QA | D | 0.078 | 46 | 20 |
| Comparative Example 17 | photoreceptor QB | E | 0.079 | 38 | 21 |
| Comparative Example 18 | photoreceptor QC | F | 0.079 | 33 | 17 |
| Comparative Example 19 | photoreceptor QD | G | 0.078 | 23 | 20 |
| Comparative Example 20 | photoreceptor QE | H | charge transport layer was unable to be formed due to poor solubility of the charge transport substance | | |
| Comparative Example 21 | photoreceptor QF | I | charge transport layer was unable to be formed due to poor solubility of the charge transport substance | | |
| Comparative Example 22 | photoreceptor QG | J | charge transport layer was unable to be formed due to poor solubility of the charge transport substance | | |

It can be seen from the results given in Table 4 that the charge transport substances according to the second aspect of the invention have exceedingly high solubility in the coating-fluid solvent used for charge transport layer formation and show satisfactory film-forming properties, and that when the charge transport substances which are within the scope of the invention are used, it is possible to provide high-performance photoreceptors which have high sensitivity, are reduced in dark decay, and show satisfactory charging properties and a low residual potential.

Electrophotographic photoreceptors of Examples 12 to 14 and Comparative Examples 23 to 26 (photoreceptor numbers: photoreceptors L to N and photoreceptors QH to QK), which had a multilayer type photosensitive layer, were each produced through the same steps as for photoreceptor I, except for the following modifications.

Photoreceptor L (Example 12)

The same procedure as in Example 9 was conducted, except that the binder resin of the coating fluid for charge transport layer formation shown above in <Method for Producing Electrophotographic Photoreceptor> was replaced with the polyarylate resin (Mv=40,500) having the following structural formula (PC). Thus, photoreceptor L was produced.

[Chem. 54]

Photoreceptor M (Example 13)

The same procedure as in Example 10 was conducted, except that the binder resin of the coating fluid for charge transport layer formation shown above in <Method for Producing Electrophotographic Photoreceptor> was replaced with the polyarylate resin (Mv=40,500) having the structural formula (PC). Thus, photoreceptor M was produced.

Photoreceptor N (Example 14)

The same procedure as in Example 11 was conducted, except that the binder resin of the coating fluid for charge transport layer formation shown above in <Method for Producing Electrophotographic Photoreceptor> was replaced with the polyarylate resin (Mv=40,500) having the structural formula (PC). Thus, photoreceptor N was produced.

Photoreceptor QH (Comparative Example 23)

The same procedure as in Comparative Example 16 was conducted, except that the binder resin of the coating fluid for charge transport layer formation shown above in <Method for Producing Electrophotographic Photoreceptor> was replaced with the polyarylate resin (Mv=40,500) having the structural formula (PC). Thus, photoreceptor QH was produced.

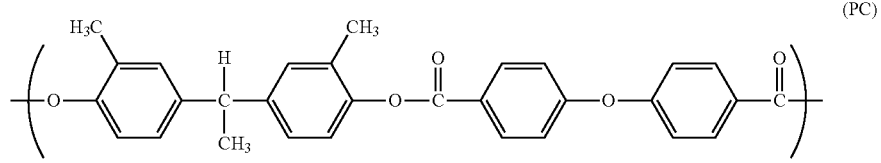

(PC)

Photoreceptor QI (Comparative Example 24)

The same procedure as in Comparative Example 17 was conducted, except that the binder resin of the coating fluid for charge transport layer formation shown above in <Method for Producing Electrophotographic Photoreceptor> was replaced with the polyarylate resin (Mv=40,500) having the structural formula (PC). Thus, photoreceptor QI was produced.

Photoreceptor QJ (Comparative Example 25)

The same procedure as in Comparative Example 18 was conducted, except that the binder resin of the coating fluid for charge transport layer formation shown above in <Method for Producing Electrophotographic Photoreceptor> was replaced with the polyarylate resin (Mv=40,500) having the structural formula (PC). Thus, photoreceptor QJ was produced.

Photoreceptor QK (Comparative Example 26)

The same procedure as in Comparative Example 19 was conducted, except that the binder resin of the coating fluid for charge transport layer formation shown above in <Method for Producing Electrophotographic Photoreceptor> was replaced with the polyarylate resin (Mv=40,500) having the structural formula (PC). Thus, photoreceptor QK was produced.

The electrophotographic photoreceptors of Examples 12 to 14 and Comparative Examples 23 to 26 were evaluated in accordance with <Evaluation of Electrophotographic Photoreceptors>. The results thereof are shown in Table 5.

TABLE 5

| | | Charge transport substance | Sensitivity ($\mu J/cm^2$) | Residual potential (−V) | Dark decay (V) |
|---|---|---|---|---|---|
| Example 12 | photoreceptor L | CT2-7 to 9 | 0.093 | 38 | 23 |
| Example 13 | photoreceptor M | CT2-10 to 12 | 0.091 | 29 | 25 |
| Example 14 | photoreceptor N | CT2-13 to 15 | 0.09 | 39 | 20 |
| Comparative Example 23 | photoreceptor QH | D | 0.094 | 114 | 32 |
| Comparative Example 24 | photoreceptor QI | E | 0.093 | 171 | 34 |
| Comparative Example 25 | photoreceptor QJ | F | 0.096 | 117 | 33 |
| Comparative Example 26 | photoreceptor QK | G | 0.092 | 90 | 31 |

It has become obvious from the results given in Table 5 that when the charge transport substances according to the second aspect of the invention are used, it is possible to provide high-performance photoreceptors which have high sensitivity, are reduced in dark decay, and show satisfactory charging properties and a low residual potential, irrespective of the binder resin used in the charge transport layers.

While the invention has been described in detail and with reference to specific embodiments thereof, it will be apparent to one skilled in the art that various changes and modifications can be made therein without departing from the spirit and scope thereof. This application is based on a Japanese patent application filed on Mar. 4, 2011 (Application No. 2011-047684) and a Japanese patent application filed on Mar. 4, 2011 (Application No. 2011-047685), the contents thereof being incorporated herein by reference.

INDUSTRIAL APPLICABILITY

The charge transport substances of the invention are suitable for use in the technical fields where charge transport materials for organic electroluminescence, for electrophotographic photoreceptors, for organic solar cells, etc. are used.

DESCRIPTION OF THE REFERENCE NUMERALS AND SIGNS

1 Electrophotographic photoreceptor (photoreceptor)
2 Charging device (charging roller; charging part)
3 Exposure device (exposure part)
4 Developing device (developing part)
5 Transfer device
6 Cleaner
7 Fixing device
41 Developing vessel
42 Agitator
43 Feed roller
44 Developing roller
45 Control member
71 Upper fixing member (fixing roller)
72 Lower fixing member (fixing roller)
73 Heater
T Toner
P Recording paper (paper, medium)

The invention claimed is:

1. An electrophotographic photoreceptor comprising:
a conductive support; and
at least a photosensitive layer formed over the support, wherein the photosensitive layer comprises:
a positional-isomer mixture consisting of isomers each represented by formula (2); and
oxytitanium phthalocyanine having a crystal form which, when examined by X-ray powder diffractometry using a CuKα characteristic X-ray line, gives a spectrum which shows diffraction peaks at Bragg angles (2θ±0.2°) of at least 24.1° and 27.2:

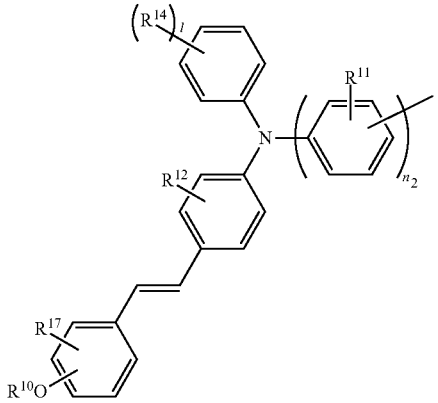

Formula (2)

-continued

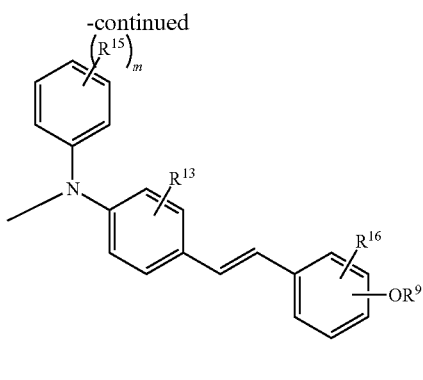

wherein $R^9$ and $R^{10}$ each independently represent an alkyl group, and $R^{11}$ to $R^{17}$ each independently represent a hydrogen atom, an alkyl group, an aryl group, or an alkoxy group, and $n_2$ represents an integer of 2-5, and 1 and m each independently represent an integer of 1-5, and wherein the isomers are two or more positional isomers selected from the group consisting of:

an isomer in which a substitution position of —$OR^9$ is the ortho position and a substitution position of —$OR^{10}$ is the ortho position, with respect to the styryl group in formula (2);

an isomer in which a substitution position of —$OR^9$ is the ortho position and a substitution position of —$OR^{10}$ is the para position, with respect to the styryl group in formula (2); and an isomer in which a substitution position of —$OR^9$ is the para position and a substitution position of —$OR^{10}$ is the para position, with respect to the styryl group in formula (2).

2. An electrophotographic photoreceptor cartridge comprising:

the electrophotographic photoreceptor according to claim 1; and at least one device selected from the group consisting of a charging device which charges the electrophotographic photoreceptor, an exposure device which exposes the charged electrophotographic photoreceptor to light to form an electrostatic latent image, and a developing device which develops the electrostatic latent image formed on the electrophotographic photoreceptor.

3. An image-forming apparatus comprising:

the electrophotographic photoreceptor according to claim 1;

a charging device which charges the electrophotographic photoreceptor;

an exposure device which exposes the charged electrophotographic photoreceptor to light to form an electrostatic latent image; and a developing device which develops the electrostatic latent image formed on the electrophotographic photoreceptor.

4. A charge transport substance represented by formula CT1-8:

5. An electrophotographic photoreceptor, comprising:

a conductive support; and at least a photosensitive layer formed over the support, wherein the photosensitive layer comprises a charge transport substance is-represented by formula CT1-8:

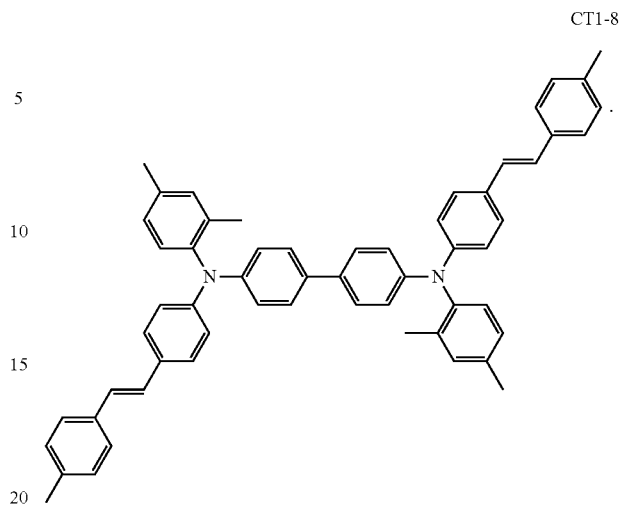

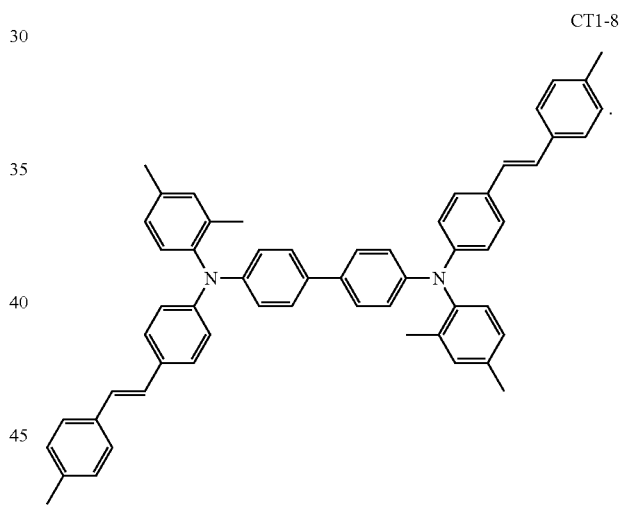

6. The electrophotographic photoreceptor according to claim 1, wherein in the formula (2), $R^9$ and $R^{10}$ each independently represent an alkyl group having 1-2 carbon atoms.

7. The electrophotographic photoreceptor according to claim 1, wherein in the formula (2), $R^{11}$ to $R^{13}$ each independently represent a hydrogen atom.

8. The electrophotographic photoreceptor according to claim 1, wherein in the formula (2), $R^{14}$ and $R^{15}$ each independently represent an alkyl group having 1-2 carbon atoms.

9. The electrophotographic photoreceptor according to claim 1, wherein in the formula (2), $R^{16}$ and $R^{17}$ each independently represent a hydrogen atom.

10. The electrophotographic photoreceptor according to claim 1, wherein in the formula (2), $n_2$ is 2.

11. The electrophotographic photoreceptor according to claim 1, wherein the positional-isomer mixture consists of:

the isomer in which the substitution position of —OR$^9$ is the ortho position and the substitution position of —OR$^{10}$ is the ortho position, with respect to the styryl group in formula (2);

the isomer in which the substitution position of —OR$^9$ is the ortho position and the substitution position of —OR$^{10}$ is the para position, with respect to the styryl group in formula (2); and the isomer in which the substitution position of —OR$^9$ is the para position and the substitution position of —OR$^{10}$ is the para position, with respect to the styryl group in formula (2).

\* \* \* \* \*